US012809893B2

(12) United States Patent
Cantu et al.

(10) Patent No.: US 12,809,893 B2
(45) Date of Patent: Nov. 24, 2026

(54) INTERACTIVE PHYSIOLOGICAL MONITORING SYSTEMS

(71) Applicant: Whoop, Inc., Boston, MA (US)

(72) Inventors: Viviano Cantu, Boston, MA (US); Nicholas John Cipollo, Charlestown, MA (US); Justin Tyler Coon, Boston, MA (US); Alexander Keyser White, San Francisco, CA (US); Laurent Ducharme Rivard, Needham, MA (US); Jaime Waydo, Saratoga, CA (US)

(73) Assignee: Whoop, Inc., Boston, MA (US)

( * ) Notice: Subject to any disclaimer, the term of this patent is extended or adjusted under 35 U.S.C. 154(b) by 226 days.

(21) Appl. No.: 18/779,546

(22) Filed: Jul. 22, 2024

(65) Prior Publication Data

US 2025/0028746 A1 Jan. 23, 2025

Related U.S. Application Data

(63) Continuation of application No. PCT/US2024/038851, filed on Jul. 19, 2024.

(Continued)

(51) Int. Cl.

*G06F 40/40* (2020.01)
*G06F 16/332* (2019.01)

(Continued)

(52) U.S. Cl.

CPC ...... *G06F 16/3329* (2019.01); *G06F 16/3328* (2019.01); *A61B 5/6831* (2013.01); *A61B 2560/045* (2013.01); *A61B 2560/0462* (2013.01)

(58) Field of Classification Search

CPC ... G06F 16/3329; G06F 16/3328; G10L 15/22

See application file for complete search history.

(56) References Cited

U.S. PATENT DOCUMENTS

| | | | |
|---|---|---|---|
| 2002/0124295 A1 | 9/2002 | Fenwick et al. |
| 2010/0292599 A1 | 11/2010 | Oleson et al. |

(Continued)

FOREIGN PATENT DOCUMENTS

| | | |
|---|---|---|
| EP | 3332698 | 6/2018 |
| WO | WO-2014188171 | 11/2014 |

(Continued)

OTHER PUBLICATIONS

Mason, Ashley E. et al., "Detection of COVID-19 using multimodal data from a wearable device: results from the first TemPredict Study", Scientific Reports, (2022) 12:3463, https://doi.org/10.1038/s41598-022-07314-0 NPL-332 Mar. 2, 2022 , 15 Pages.

(Continued)

*Primary Examiner* — Mark Villena

(74) *Attorney, Agent, or Firm* — Strategic Patents, P.C.

(57) ABSTRACT

A user question can be classified into topics and mapped to appropriate static and/or dynamic content related to the user and/or question. This data can then be collectively provided to a large language model in order to generate a suitable response, which may include, for example, summarization, rephrasing, analysis, and the like, as well as executable code for dynamically presenting content of the response to the user and/or functionally adapting a user platform according to the response.

21 Claims, 16 Drawing Sheets

Related U.S. Application Data

(60) Provisional application No. 63/624,921, filed on Jan. 25, 2024, provisional application No. 63/587,319, filed on Oct. 2, 2023, provisional application No. 63/515,026, filed on Jul. 21, 2023.

(51) Int. Cl.
*G06F 16/3329* (2025.01)
*A61B 5/00* (2006.01)

(56) References Cited

U.S. PATENT DOCUMENTS

| | | | |
|---|---|---|---|
| 2014/0180019 | A1 | 6/2014 | Martinez et al. |
| 2016/0135743 | A1 | 5/2016 | Cobbett et al. |
| 2016/0266606 | A1 | 9/2016 | Ricci |
| 2018/0220962 | A1 | 8/2018 | Palley et al. |
| 2018/0242654 | A1 | 8/2018 | Marikkar et al. |
| 2019/0110748 | A1 | 4/2019 | Cho et al. |
| 2019/0159680 | A1 | 5/2019 | Tanaka et al. |
| 2021/0011887 | A1* | 1/2021 | Visser ................. G06F 16/1805 |
| 2021/0401314 | A1 | 12/2021 | Pho et al. |
| 2021/0401378 | A1 | 12/2021 | Pho et al. |
| 2021/0407684 | A1 | 12/2021 | Pho et al. |
| 2022/0409187 | A1 | 12/2022 | Pho et al. |
| 2024/0412029 | A1* | 12/2024 | Yang ....................... G06F 40/30 |
| 2024/0419246 | A1* | 12/2024 | Ullrich .................... G06F 3/015 |
| 2025/0200014 | A1* | 6/2025 | Abbo ................ G06F 16/24522 |

FOREIGN PATENT DOCUMENTS

| | | |
|---|---|---|
| WO | WO-2015134654 | 9/2015 |
| WO | WO-2019168475 | 9/2019 |
| WO | WO-2019213114 | 11/2019 |
| WO | WO-2025024317 | 1/2025 |

OTHER PUBLICATIONS

Smarr, Benjamin L. et al., "Feasibility of continuous fever monitoring using wearable devices", Scientific Reports | (2020) 10:21640, https://doi.org/10.1038/s41598-020-78355-6 NPL-333 Dec. 14, 2020 , 11 Pages.

ISA/EP, , "PCT Application No. PCT/US24/38851 International Search Report and Written Opinion mailed Jan. 17, 2025", , 18 pages.

Poesia, Gabriel et al., "Synchromesh: Reliable Code Generation From Pre-Trained Language Models", ARXIV.org, Cornell University Library, 201 Olin Library Cornell University Ithaca, NY 14853, Jan. 26, 2022 Jan. 26, 2022 , 19 pages.

Liu, Xin et al., "Large Language Models are Few-Shot Health Learners", ARXIV.org, Cornell University Library, 201 Olin Library Cornell University Ithaca, NY 14853, May 24, 2023 May 24, 2023 , 13 pages.

Jin, Matthew et al., "InferFix: End-to-End Program Repair with LLMs over Retrieval-Augmented Prompts", ARXIV.org, Cornell University Library, 201 Olin Library Cornell University Ithaca, NY 14853, Mar. 13, 2023 Mar. 13, 2023 , 11 pages.

ISA/EP, , "PCT Application No. PCT/US24/38851 Invitation to pay addition fee/ partial search mailed Nov. 12, 2024", , 11 pages.

Wipo, , "PCT Application No. PCT/US24/38851 International Preliminary Report on Patentability mailed Feb. 5, 2026", , 13 pages.

* cited by examiner

INTERACTIVE PHYSIOLOGICAL MONITORING SYSTEMS

RELATED APPLICATIONS

This application is a bypass continuation of Int'l Pat. App. No. PCT/US24/38851 filed on Jul. 19, 2024, which claims priority to U.S. Prov. Pat. App. No. 63/515,026 filed on Jul. 21, 2023, U.S. Prov. Pat. App. No. 63/587,319 filed on Oct. 2, 2023, and U.S. Prov. Pat. App. No. 63/624,921 filed on Jan. 25, 2024. The entire content of each of the foregoing applications is hereby incorporated by reference.

TECHNICAL FIELD

The present disclosure generally relates to physiological monitoring systems, and more specifically to generating context-specific responses to a query received from a user of a physiological monitoring system.

BACKGROUND

Physiological monitoring systems can provide a user with a rich vein of physiological data and analysis, where a user can monitor metrics such as sleep performance, activity, strain, and recovery, as well as use this information to make informed decisions based on the data and/or metrics. However, with the increasing complexity of such systems, it can be difficult for a user to access and analyze data of interest.

There remains a need for improved access to complex, data-rich systems such as a continuous physiological monitoring system.

SUMMARY

A user question can be classified into topics and mapped to appropriate static and/or dynamic content related to the user and/or question. This data can then be collectively provided to a large language model in order to generate a suitable response, which may include, for example, summarization, rephrasing, analysis, and the like, as well as executable code for dynamically presenting content of the response to the user and/or functionally adapting a user platform according to the response.

According to one aspect of the present disclosure there is provided a method including: receiving physiological data for a user from a physiological monitoring system, the physiological monitoring system including a physiological monitor worn by the user and providing the physiological data; obtaining a message received from the user, where the message includes a natural language request associated with the physiological data received for the user; generating a prompt for a large language model (LLM), the prompt including: a context block based on the message received from the user; a request for a code block encoding a response to the request based on the context block; a language schema for code within the code block, the language schema defining at least a syntax, functions, and operators for a programming language used to express the code block; and an object schema, the object schema specifying programming objects available for use in the code block. The method may also include: transmitting the prompt to the LLM; obtaining, from the LLM, an output containing the code block, where the code block is configured for execution by one or more components of the physiological monitoring system to generate one or more component specific representations of the response; and processing, by a first component of the physiological monitoring system, the code block thereby generating a first component specific representation of the response for the first component of the physiological monitoring system. Other embodiments of this aspect include corresponding computer systems, apparatus, and computer programs recorded on one or more computer storage devices, each configured to perform the actions of the methods.

According to another aspect of the present disclosure there is provided a computer program product comprising computer executable code embodied in a non-transitory computer readable medium that, when executing on one or more computing devices, performs the steps of: receiving physiological data for a user from a system, the system including a physiological monitor worn by the user and the physiological monitor providing the physiological data; receiving a message from the user, where the message includes a question from the user in a natural language form; creating one or more prompts for use with large language models, the one or more prompts including: a request for a code block that encodes a response to the question and is processable by one or more components of the system to generate one or more component specific representations of the response; a language schema for code within the code block, the language schema defining at least a syntax, functions, and operators for a programming language used to express the code block; an object schema, the object schema specifying programming objects available for use in the code block; and a context block relating to user-specific data. The computer program product may further include code that, when executed on one or more computing devices, performs the steps of: transmitting the one or more prompts to one or more large language models; receiving the response containing the code block from the one or more large language models; and transmitting the code block that encodes the response to a component of the system for use in providing the response to the user.

According to another aspect of the present disclosure there is provided a system including: a physiological monitor used to acquire physiological data from a user; one or more computing devices associated with the user; and a query module, the query module executing on one or more processors and configured by non-transitory computer executable code to perform the steps of: receiving a message from the user, where the message includes a question from the user in a natural language form; creating one or more prompts for use with large language models, the one or more prompts including: a request for a code block that encodes a response to the question and is processable by the one or more computing devices to generate one or more component specific representations of the response; a language schema for code within the code block, the language schema defining at least a syntax, functions, and operators for a programming language used to express the code block; an object schema, the object schema specifying programming objects available for use in the code block; and a context block relating to user-specific data for the user based on the physiological data. The query module executing on one or more processors may be further configured by non-transitory computer executable code to perform the steps of: transmitting the one or more prompts to one or more large language models; and receiving the code block that encodes the response from one of the large language models.

According to another aspect of the present disclosure there is provided a method including: obtaining a portion of a natural language message received from a user of a system, where the portion of the natural language message relates to a request from the user; providing, to a first large language model (LLM), a prompt operable to cause the first LLM to output a code block that encodes a response to the request and is processable by one or more components of the system to generate one or more component specific representations of the response, where the prompt includes a predetermined instruction, a context block based on the portion of the natural language message, a language schema for code within the code block, and an object schema that defines objects usable within the code block, where the object schema is related to the request from the user; and obtaining the code block from the first LLM. Other embodiments of this aspect include corresponding computer systems, apparatus, and computer programs recorded on one or more computer storage devices, each configured to perform the actions of the methods.

According to another aspect of the present disclosure there is provided a device comprising one or more processors and a memory storing instructions that, when executed by the one or more processors, cause the device to perform the steps of: obtaining a portion of a natural language message received from a user of a system, where the portion of the natural language message relates to a request from the user; providing, to a first large language model (LLM), a prompt operable to cause the first LLM to output a code block that encodes a response to the request and is processable by one or more components of the system to generate one or more component specific representations of the response, where the prompt includes a predetermined instruction, a context block based on the portion of the natural language message, a language schema for code within the code block, and an object schema that defines objects usable within the code block, where the object schema is related to the request from the user; and obtaining the code block from the first LLM.

According to another aspect of the present disclosure there is provided a computer program product comprising computer executable code embodied in a non-transitory computer readable medium that, when executing on one or more computing devices, performs the steps of: obtaining a portion of a natural language message received from a user of a system, where the portion of the natural language message relates to a request from the user; configuring a large language model (LLM) to generate a code block that encodes a response to the request and is processable by one or more components of the system to generate one or more component specific representations of the response; and obtaining the code block from the LLM.

According to another aspect of the present disclosure there is provided a method including: obtaining a portion of a natural language message received from a user of a physiological monitoring system, where the portion of the natural language message relates to a request from the user; classifying the portion of the natural language message into one or more topics, where each of the one or more topics is associated with the request included in the portion of the natural language message; providing, to a first large language model (LLM), a prompt operable to cause the first LLM to output a code block that encodes a response to the request; obtaining the code block from the first LLM and subsequently evaluating the code block to obtain context data related to the one or more topics; generating a command including the context data and an instruction portion, where the instruction portion includes instructions for a second large language model (LLM) to perform a rephrasing task based on the context data; providing the command to the second LLM and subsequently obtaining a text-based response from the second LLM, where the text-based response includes a natural language representation of the context data; and causing a response based on the text-based response to be output to the user. Other embodiments of this aspect include corresponding computer systems, apparatus, and computer programs recorded on one or more computer storage devices, each configured to perform the actions of the methods.

According to another aspect of the present disclosure there is provided a computer program product comprising computer executable code embodied in a non-transitory computer readable medium that, when executing on one or more computing devices, performs the steps of: obtaining a message from a user of a physiological monitoring system, the message including a query associated with the physiological monitoring system; classifying the message into one or more topics, where each of the one or more topics is associated with the query included in the message; mapping, using one or more mapping functions, the one or more topics to a set of context specific data, where each of the one or more mapping functions obtains context specific data associated with a respective topic of the one or more topics, the context specific data including static data, and/or dynamic data associated with the physiological monitoring system; generating a command including a context portion based on the set of context specific data and an instruction portion, where the instruction portion includes instructions for a first large language model (LLM) to perform a rephrasing task based on the context portion; providing the command to the first LLM and subsequently obtaining a text-based response from the first LLM, where the text-based response includes a natural language representation of the context portion of the command; and causing a response based on the text-based response to be output to the user.

According to another aspect of the present disclosure there is provided a method including: obtaining a message from a user of a physiological monitoring system, the message including a query associated with the physiological monitoring system; classifying the message into one or more topics, where each of the one or more topics is associated with the query included in the message; mapping, using one or more mapping functions, the one or more topics to a set of context specific data, where each of the one or more mapping functions obtains context specific data associated with a respective topic of the one or more topics, the context specific data including static data, and/or dynamic data associated with the physiological monitoring system; generating a command including a context portion based on the set of context specific data and an instruction portion, where the instruction portion includes instructions for first a large language model (LLM) to perform a rephrasing task based on the context portion; providing the command to the first LLM and subsequently obtaining a text-based response from the first LLM, where the text-based response includes a natural language representation of the context portion; and causing a response based on the text-based response to be output to the user. Other embodiments of this aspect include corresponding computer systems, apparatus, and computer programs recorded on one or more computer storage devices, each configured to perform the actions of the methods.

According to another aspect of the present disclosure there is provided a system including: a wearable physiological monitor including one or more sensors, a first processor configured to obtain a physiological metric for a user based on a signal from the one or more sensors, and a communications interface for coupling with a remote resource; a server coupled in a communicating relationship with the wearable physiological monitor, the server including a second processor configured by computer executable code to: obtain a message from the user, where the message includes a query; classify the message into one or more topics, where each of the one or more topics is associated with the query included in the message; map, using one or more mapping functions, the one or more topics to a set of context specific data, where each of the one or more mapping functions obtains context specific data associated with a respective topic of the one or more topics, the context specific data including static data, and/or the physiological metric for the user; generate a command including a context portion based on the set of context specific data and an instruction portion, where the instruction portion includes instructions for a large language model (LLM) to perform a rephrasing task based on the context portion; and provide the command to the LLM and subsequently obtain a response from the LLM, where the response includes a natural language representation of the context portion. The system may also include a user interface configured to present the response to the user.

According to another aspect of the present disclosure there is provided a method including: obtaining a message from a user, the message including an ambiguous query; generating a structured query in a query language by providing one or more prompts to a large language model (LLM), where the one or more prompts include a predetermined instruction, the message from the user, and a schema for the query language; parsing the structured query to generate an abstract syntax tree (AST) representation of the structured query; evaluating the AST representation of the structured query to obtain context specific data related to one or more topics associated with the ambiguous query, where the context specific data is obtained using one or more mapping functions identified from evaluation of the AST representation of the structured query; and outputting the context specific data as a resolution to the ambiguous query. Other embodiments of this aspect include corresponding computer systems, apparatus, and computer programs recorded on one or more computer storage devices, each configured to perform the actions of the methods.

According to another aspect of the present disclosure there is provided a computer program product comprising computer executable code embodied in a non-transitory computer readable medium that, when executing on one or more computing devices, performs the steps of: obtaining a message from a user, the message including an ambiguous query; generating a structured query in a query language by providing one or more prompts to a large language model (LLM), where the one or more prompts include a predetermined instruction, the message from the user, and a schema for the query language; parsing the structured query to generate an abstract syntax tree (AST) representation of the structured query; evaluating the AST representation of the structured query to obtain context specific data related to one or more topics associated with the ambiguous query, where the context specific data is obtained using one or more mapping functions identified from evaluation of the AST representation of the structured query; and outputting the context specific data as a resolution to the ambiguous query.

According to another aspect of the present disclosure there is provided a device comprising one or more processors and a memory storing instructions that, when executed by the one or more processors, cause the device to perform the steps of: obtaining a message from a user, the message including an ambiguous query; generating a structured query in a query language by providing one or more prompts to a large language model (LLM), where the one or more prompts include a predetermined instruction, the message from the user, and a schema for the query language; parsing the structured query to generate an abstract syntax tree (AST) representation of the structured query; evaluating the AST representation of the structured query to obtain context specific data related to one or more topics associated with the ambiguous query, where the context specific data is obtained using one or more mapping functions identified from evaluation of the AST representation of the structured query; and outputting the context specific data as a resolution to the ambiguous query.

According to another aspect of the present disclosure there is provided a method for dynamically optimizing load on a large language model (LLM), the method including: identifying a prompt to be provided to an LLM for performing a task related to a physiological monitoring system; obtaining one or more load values indicative of a computational load on the LLM; generating a command including instructions for the LLM to generate an output according to an output length criterion, where the output length criterion is based on the one or more load values; and providing, to the LLM, the prompt and the command such that a subsequent output generated by the LLM satisfies the output length criterion. Other embodiments of this aspect include corresponding computer systems, apparatus, and computer programs recorded on one or more computer storage devices, each configured to perform the actions of the methods.

According to another aspect of the present disclosure there is provided a computer program product comprising computer executable code embodied in a non-transitory computer readable medium that, when executing on one or more computing devices, performs the steps of: identifying a prompt to be provided to an LLM for performing a task related to a physiological monitoring system; obtaining one or more load values indicative of a computational load on the LLM; generating a command including instructions for the LLM to generate an output according to an output length criterion, where the output length criterion is based on the one or more load values; and providing, to the LLM, the prompt and the command such that a subsequent output generated by the LLM satisfies the output length criterion.

According to another aspect of the present disclosure there is provided a device comprising one or more processors and a memory storing instructions that, when executed by the one or more processors, cause the device to perform the steps of: identifying a prompt to be provided to an LLM for performing a task related to a physiological monitoring system; obtaining one or more load values indicative of a computational load on the LLM; generating a command including instructions for the LLM to generate an output according to an output length criterion, where the output length criterion is based on the one or more load values; and providing, to the LLM, the prompt and the command such that a subsequent output generated by the LLM satisfies the output length criterion.

According to another aspect of the present disclosure there is provided a method for generating cross-component responses to user requests, the method including: obtaining a portion of a natural language message received from a user of a physiological monitoring system, where the portion of the natural language message relates to a request from the user in relation to one or more operations performed by the physiological monitoring system; providing, to a large language model (LLM), a prompt operable to cause the LLM to output a code block which encodes a response to the request and is processable by one or more components of the physiological monitoring system to generate one or more component specific representations of the response, where the prompt includes a predetermined instruction, the portion of the natural language message, a language schema for code within the code block, and an object schema related to the one or more operations performed by the physiological monitoring system; and obtaining the code block from the LLM. Other embodiments of this aspect include corresponding computer systems, apparatus, and computer programs recorded on one or more computer storage devices, each configured to perform the actions of the methods.

According to another aspect of the present disclosure there is provided a computer program product comprising computer executable code embodied in a non-transitory computer readable medium that, when executing on one or more computing devices, performs the steps of: obtaining a portion of a natural language message received from a user of a physiological monitoring system, where the portion of the natural language message relates to a request from the user in relation to one or more operations performed by the physiological monitoring system; providing, to a large language model (LLM), a prompt operable to cause the LLM to output a code block which encodes a response to the request and is processable by one or more components of the physiological monitoring system to generate one or more component specific representations of the response, where the prompt includes a predetermined instruction, the portion of the natural language message, a language schema for code within the code block, and an object schema related to the one or more operations performed by the physiological monitoring system; and obtaining the code block from the LLM.

According to another aspect of the present disclosure there is provided a device comprising one or more processors and a memory storing instructions that, when executed by the one or more processors, cause the device to perform the steps of: obtaining a portion of a natural language message received from a user of a physiological monitoring system, where the portion of the natural language message relates to a request from the user in relation to one or more operations performed by the physiological monitoring system; providing, to a large language model (LLM), a prompt operable to cause the LLM to output a code block which encodes a response to the request and is processable by one or more components of the physiological monitoring system to generate one or more component specific representations of the response, where the prompt includes a predetermined instruction, the portion of the natural language message, a language schema for code within the code block, and an object schema related to the one or more operations performed by the physiological monitoring system; and obtaining the code block from the LLM.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DESCRIPTION

Figure 1:
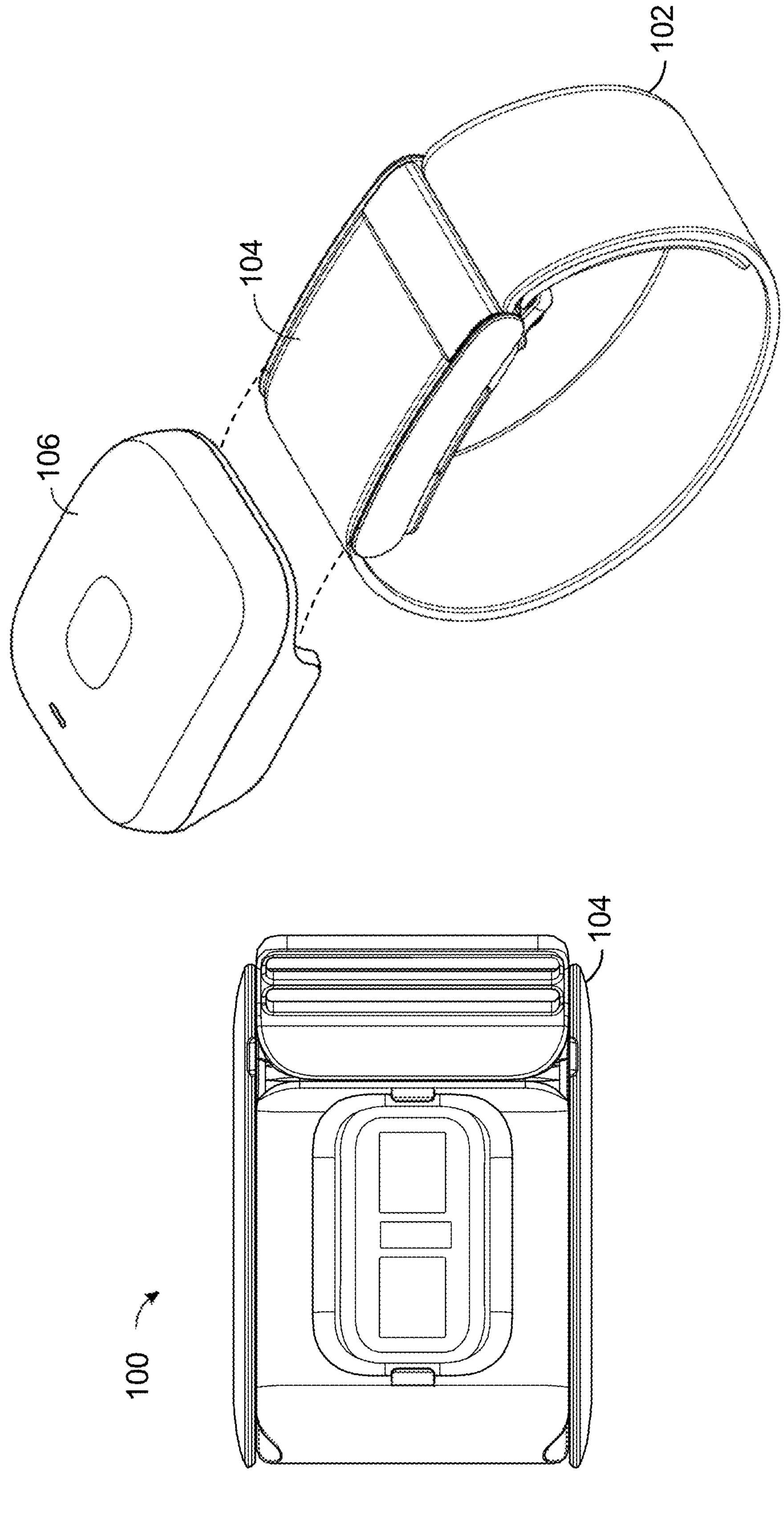
FIG. 1 shows a physiological monitoring device.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better describe the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms unless specifically stated to the contrary.

The term "user" as used herein, refers to any type of animal, human or non-human, whose physiological information may be monitored using an exemplary wearable physiological monitoring system.

The term "continuous," as used herein in connection with heart rate data, refers to the acquisition of heart rate data at a sufficient frequency to enable detection of individual heartbeats, and also refers to the collection of heart rate data over extended periods such as an hour, a day or more (including acquisition throughout the day and night). More generally with respect to physiological signals that might be monitored by a wearable device, "continuous" or "continuously" will be understood to mean continuously at a rate and duration suitable for the intended time-based processing, and physically at an inter-periodic rate (e.g., multiple times per heartbeat, respiration, and so forth) sufficient for resolving the desired physiological characteristics such as heart rate, heart rate variability, heart rate peak detection, pulse shape, and so forth. At the same time, continuous monitoring is not intended to exclude ordinary data acquisition interruptions such as temporary displacement of monitoring hardware due to sudden movements, changes in external lighting, loss of electrical power, physical manipulation and/or adjustment by a wearer, physical displacement of monitoring hardware due to external forces, and so forth. It will also be noted that heart rate data or a monitored heart rate, in this context, may more generally refer to raw sensor data such as optical intensity signals, or processed data therefrom such as heart rate data, signal peak data, heart rate variability data, or any other physiological or digital signal suitable for recovering heart rate information as contemplated herein. Furthermore, such heart rate data may generally be captured over some historical period that can be subsequently correlated to various other data or metrics related to, e.g., sleep states, recognized exercise activities, resting heart rate, maximum heart rate, and so forth.

The term "computer-readable medium," as used herein, refers to a non-transitory storage media such as storage hardware, storage devices, computer memory that may be accessed by a controller, a microcontroller, a microprocessor, a computational system, or the like, or any other module or component or module of a computational system to encode thereon computer-executable instructions, software programs, and/or other data. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), virtual or physical computer system memory, physical memory hardware such as random access memory (such as, DRAM, SRAM, EDO RAM), and so forth. Although not depicted, any of the devices or components described herein may include a computer-readable medium or other memory for storing program instructions, data, and the like.

FIG. 1 shows a physiological monitoring system. The system 100 may include a wearable monitor 104 that is configured for physiological monitoring. The system 100 may also include a removable and replaceable battery 106 for recharging the wearable monitor 104. The wearable monitor 104 may include a strap 102 or other retaining system(s) for securing the wearable monitor 104 in a position on a wearer's body for the acquisition of physiological data as described herein. For example, the strap 102 may include a slim elastic band formed of any suitable clastic material such as a rubber or a woven polymer fiber such as a woven polyester, polypropylene, nylon, spandex, and so forth. The strap 102 may be adjustable to accommodate different wrist sizes, and may include any latches, hasps, or the like to secure the wearable monitor 104 in an intended position for monitoring a physiological signal. While a wrist-worn device is depicted, it will be understood that the wearable monitor 104 may be configured for positioning in any suitable location on a user's body, based on the sensing modality and the nature of the signal to be acquired. For example, the wearable monitor 104 may be configured for use on a wrist, an ankle, a bicep, a chest, or any other suitable location(s), and the strap 102 may be, or may include, a waistband or other elastic band or the like within an article of clothing or accessory. The wearable monitor 104 may also or instead be structurally configured for placement on or within a garment, e.g., permanently or in a removable and replaceable manner. To that end, the wearable monitor 104 may be shaped and sized for placement within a pocket, slot, and/or other housing that is coupled to or embedded within a garment. In such configurations, the pocket or other retaining arrangement on the garment may include sensing windows or the like so that the wearable monitor 104 can operate while placed for use in the garment. U.S. Pat. No. 11,185,292 describes non-limiting example embodiments of suitable wearable monitors 104, and is incorporated herein by reference in its entirety.

The system 100 may include any hardware components, subsystems, and the like to support various functions of the wearable monitor 104 such as data collection, processing, display, and communications with external resources. For example, the system 100 may include hardware for a heart rate monitor using, e.g., photoplethysmography, electrocardiogram any other technique(s). The system 100 may be configured such that, when the wearable monitor 104 is placed for use about a wrist (or at some other body location), the system 100 initiates acquisition of physiological data from the wearer. In some embodiments, the pulse or heart rate may be acquired optically based on a light source (such as light emitting diodes (LEDs)) and optical detectors in the wearable monitor 104. The LEDs may be positioned to direct illumination toward the user's skin, and optical detectors such as photodiodes may be used to capture illumination intensity measurements indicative of illumination from the LEDs that is reflected and/or transmitted by the wearer's skin. In one embodiment, the physiological monitoring system (e.g., the wearable monitor and battery) takes a form other than that shown in FIG. 1. For example, the physiological monitoring system may be arranged and configured as a ring to be worn on a finger or thumb of a user, or as a bicep band, sock, or other accessory, apparel item, or the like.

The system 100 may be configured to record other physiological and/or biomechanical parameters including, but not limited to, skin temperature (using a thermometer), galvanic skin response (using a galvanic skin response sensor), motion (using one or more multi-axes accelerometers and/or gyroscope), blood pressure, and the like, as well environmental or contextual parameters such as ambient light, ambient temperature, humidity, time of day, and so forth. For example, the wearable monitor 104 may include sensors such as accelerometers and/or gyroscopes for motion detection, sensors for environmental temperature sensing, sensors to measure electrodermal activity (EDA), sensors to measure galvanic skin response (GSR) sensing, and so forth. The system 100 may also or instead include other systems or subsystems supporting addition functions of the wearable monitor 104. For example, the system 100 may include communications systems to support, e.g., near field communications, proximity sensing, Bluetooth communications, Wi-Fi communications, cellular communications, satellite communications, and so forth. The wearable monitor 104 may also or instead include components such as a Global Positioning System (GPS), a display and/or user interface, a clock and/or timer, and so forth.

The wearable monitor 104 may include one or more sources of battery power, such as a first battery within the wearable monitor 104 and a second battery 106 that is removable from and replaceable to the wearable monitor 104 in order to recharge the battery in the wearable monitor 104. Also or instead, the system 100 may include a plurality of wearable monitors 104 (and/or other physiological monitors) that can share battery power or provide power to one another. The system 100 may perform numerous functions related to continuous monitoring, such as automatically detecting when the user is asleep, awake, exercising, and so forth, and such detections may be performed locally at the wearable monitor 104 or at a remote service coupled in a communicating relationship with the wearable monitor 104 and receiving data therefrom. In general, the system 100 may support continuous, independent monitoring of a physiological signal such as a heart rate, and the underlying acquired data may be stored on the wearable monitor 104 for an extended period until it can be uploaded to a remote processing resource for more computationally complex analysis.

In one aspect, the wearable monitor may be a wrist-worn photoplethysmography device.

Figure 2:
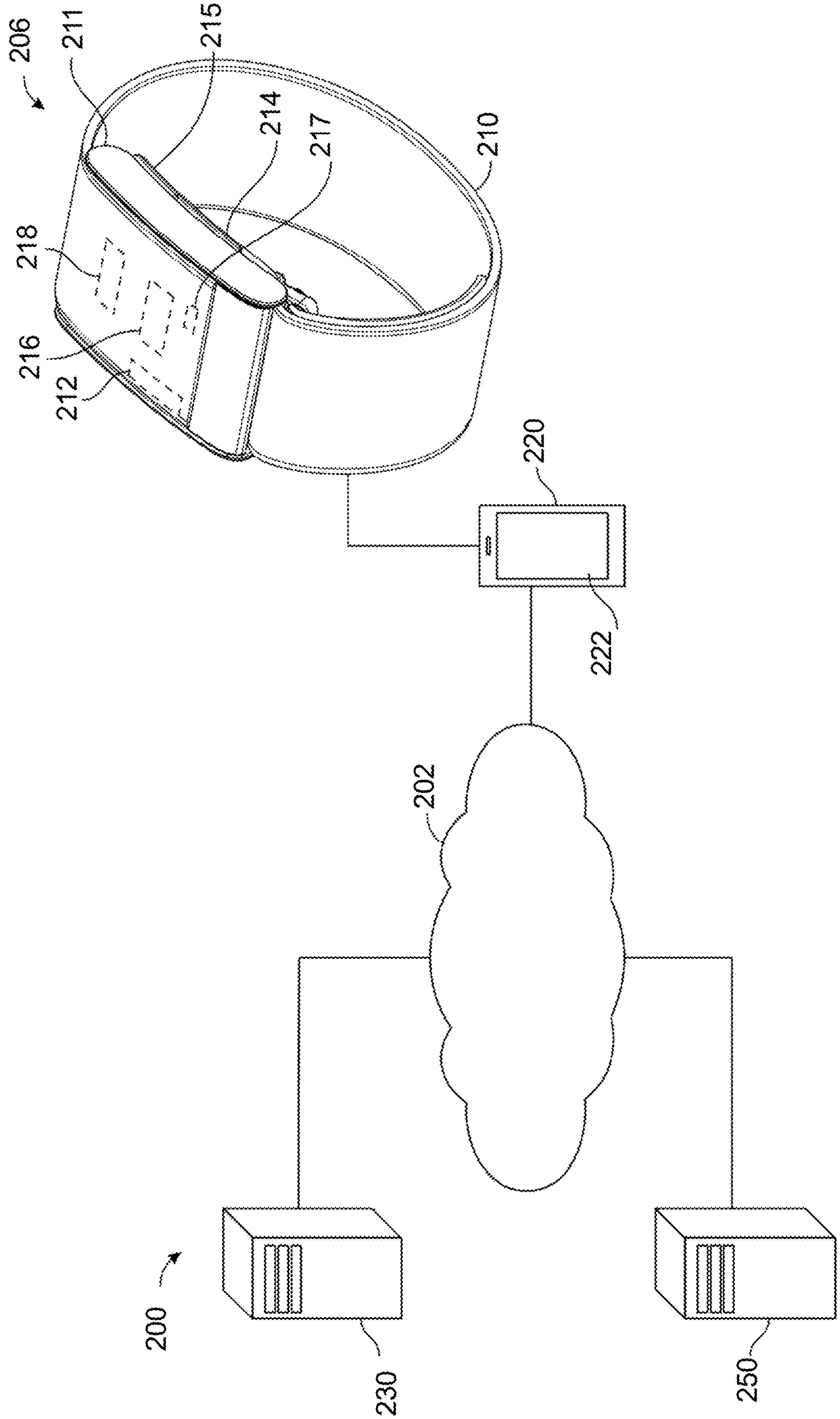
FIG. 2 illustrates a physiological monitoring system.

FIG. 2 illustrates a physiological monitoring system. More specifically, FIG. 2 illustrates a physiological monitoring system 200 that may be used with any of the methods or devices described herein. In general, the system 200 may include a physiological monitor 206, a user device 220, a remote server 230 with a remote data processing resource (such as any of the processors or processing resources described herein), and one or more other resources 250, all of which may be interconnected through a data network 202.

The data network 202 may be any of the data networks described herein. For example, the data network 202 may be any network(s) or internetwork(s) suitable for communicating data and information among participants in the system 200. This may include public networks such as the Internet, private networks, telecommunications networks such as the Public Switched Telephone Network or cellular networks using third generation (e.g., 3G or IMT-200), fourth generation (e.g., LTE (E-UTRA) or WiMAX-Advanced (IEEE 802.16m)), fifth generation (e.g., 5G), and/or other technologies, as well as any of a variety of corporate area or local area networks and other switches, routers, hubs, gateways, and the like that might be used to carry data among participants in the system 200. This may also include local or short-range communications infrastructure suitable, e.g., for coupling the physiological monitor 206 to the user device 220, or otherwise supporting communicating with local resources. By way of non-limiting examples, short range communications may include Wi-Fi communications, Bluetooth communications, infrared communications, near field communications, communications with RFID tags or readers, and so forth.

The physiological monitor 206 may, in general, be any physiological monitoring device or system, such as any of the wearable monitors or other monitoring devices or systems described herein. In one aspect, the physiological monitor 206 may be a wearable physiological monitor shaped and sized to be worn on a wrist or other body location. The physiological monitor 206 may include a wearable housing 211, a network interface 212, one or more sensors 214, one or more light sources 215, a processor 216, a haptic device 217 or other user input/output hardware, a memory 218, and a strap 210 for retaining the physiological monitor 206 in a desired location on a user. In one aspect, the physiological monitor 206 may be configured to acquire heart rate data and/or other physiological data from a wearer in an intermittent or substantially continuous manner. In another aspect, the physiological monitor 206 may be configured to support extended, continuous acquisition of physiological data, e.g., for several days, a week, or more.

The network interface 212 of the physiological monitor 206 may be configured to couple the physiological monitor 206 to one or more other components of the system 200 in a communicating relationship, either directly, e.g., through a cellular data connection or the like, or indirectly through a short range wireless communications channel coupling the physiological monitor 206 locally to a wireless access point, router, computer, laptop, tablet, cellular phone, or other device that can locally process data, and/or relay data from the physiological monitor 206 to the remote server 230 or other resource(s) 250 as necessary or helpful for acquiring and processing data from the physiological monitor 206.

The one or more sensors 214 may include any of the sensors described herein, or any other sensors or subsystems suitable for physiological monitoring or supporting functions. By way of example and not limitation, the one or more sensors 214 may include one or more of a light source, an optical sensor, an accelerometer, a gyroscope, a temperature sensor, a galvanic skin response sensor, a capacitive sensor, a resistive sensor, an environmental sensor (e.g., for measuring ambient temperature, humidity, lighting, and the like), a geolocation sensor, a Global Positioning System, a proximity sensor, an RFID tag reader, and RFID tag, a temporal sensor, an electrodermal activity sensor, and the like. The one or more sensors 214 may be disposed in the wearable housing 211, or otherwise positioned and configured for physiological monitoring or other functions described herein. In one aspect, the one or more sensors 214 include a light detector configured to provide light intensity data to the processor 216 (or to the remote server 230) for calculating a heart rate and a heart rate variability. The one or more sensors 214 may also or instead include an accelerometer, gyroscope, and the like configured to provide motion data to the processor 216, e.g., for detecting activities such as a sleep state, a resting state, a waking event, exercise, and/or other user activity. In an implementation, the one or more sensors 214 may include a sensor to measure a galvanic skin response of the user. The one or more sensors 214 may also or instead include electrodes or the like for capturing electronic signals, e.g., to obtain an electrocardiogram and/or other electrically derived physiological measurements.

The processor 216 and memory 218 may be any of the processors and memories described herein. In one aspect, the memory 218 may store physiological data obtained by monitoring a user with the one or more sensors 214, and or any other sensor data, program data, or other data useful for operation of the physiological monitor 206 or other components of the system 200. It will be understood that, while only the memory 218 on the physiological monitor is illustrated, any other device(s) or components of the system 200 may also or instead include a memory to store program instructions, raw data, processed data, user inputs, and so forth. In one aspect, the processor 216 of the physiological monitor 206 may be configured to obtain heart rate data from the user, such as heart rate data including or based on the raw data from the sensors 214. The processor 216 may also or instead be configured to determine, or assist in a determination of, a condition of the user related to, e.g., health, fitness, strain, recovery sleep, or any of the other conditions described herein.

The one or more light sources 215 may be coupled to the wearable housing 211 and controlled by the processor 216. At least one of the light sources 215 may be directed toward the skin of a user adjacent to the wearable housing 211. Light from the light source 215, or more generally, light at one or more wavelengths of the light source 215, may be detected by one or more of the sensors 214, and processed by the processor 216 as described herein.

The system 200 may further include a remote data processing resource executing on a remote server 230. The remote data processing resource may include any of the processors and related hardware described herein, and may be configured to receive data transmitted from the memory 218 of the physiological monitor 206, and to process the data to detect or infer physiological signals of interest such as heart rate, heart rate variability, respiratory rate, pulse oxygen, blood pressure, and so forth. The remote server 230 may also or instead evaluate a condition of the user such as a recovery state, sleep state, exercise activity, exercise type, sleep quality, daily activity strain, and any other health or fitness conditions that might be detected based on such data.

The system 200 may include one or more user devices 220, which may work together with the physiological monitor 206, e.g., to provide a display, or more generally, user input/output, for user data and analysis, and/or to provide a communications bridge from the network interface 212 of the physiological monitor 206 to the data network 202 and the remote server 230. For example, physiological monitor 206 may communicate locally with a user device 220, such as a smartphone of a user, via short-range communications, e.g., Bluetooth, or the like, for the exchange of data between the physiological monitor 206 and the user device 220, and the user device 220 may in turn communicate with the remote server 230 via the data network 202 in order to forward data from the physiological monitor 206 and to receive analysis and results from the remote server 230 for presentation to the user. In one aspect, the user device(s) 220 may support physiological monitoring by processing or pre-processing data from the physiological monitor 206 to support extraction of heart rate or heart rate variability data from raw data obtained by the physiological monitor 206. In another aspect, computationally intensive processing may advantageously be performed at the remote server 230, which may have greater memory capabilities and processing power than the physiological monitor 206 and/or the user device 220.

The user device 220 may include any suitable computing device(s) including, without limitation, a smartphone, a desktop computer, a laptop computer, a network computer, a tablet, a mobile device, a portable digital assistant, a cellular phone, a portable media or entertainment device, or any other computing devices described herein. The user device 220 may provide a user interface 222 for access to data and analysis by a user, and/or to support user control of operation of the physiological monitor 206. The user interface 222 may be maintained by one or more applications executing locally on the user device 220, or the user interface 222 may be remotely served and presented on the user device 220, e.g., from the remote server 230 or the one or more other resources 250.

In general, the remote server 230 may include data storage, a network interface, and/or other processing circuitry. The remote server 230 may process data from the physiological monitor 206 and perform physiological and/or health monitoring/analyses or any of the other analyses described herein, (e.g., analyzing sleep, determining strain, assessing recovery, and so on), and may host a user interface for remote access to this data, e.g., from the user device 220. The remote server 230 may include a web server or other programmatic front end that facilitates web-based access by the user devices 220 or the physiological monitor 206 to the capabilities of the remote server 230 or other components of the system 200.

The system 200 may include other resources 250, such as any resources that can be usefully employed in the devices, systems, and methods as described herein. For example, these other resources 250 may include other data networks, databases, processing resources, cloud data storage, data mining tools, computational tools, data monitoring tools, algorithms, and so forth. In another aspect, the other resources 250 may include one or more administrative or programmatic interfaces for human actors such as programmers, researchers, annotators, editors, analysts, coaches, and so forth, to interact with any of the foregoing. The other resources 250 may also or instead include any other software or hardware resources that may be usefully employed in the networked applications as contemplated herein. For example, the other resources 250 may include payment processing servers or platforms used to authorize payment for access, content, or option/feature purchases. In another aspect, the other resources 250 may include certificate servers or other security resources for third-party verification of identity, encryption or decryption of data, and so forth. In another aspect, the other resources 250 may include a desktop computer or the like co-located (e.g., on the same local area network with, or directly coupled to through a serial or USB cable) with a user device 220, wearable strap 210, or remote server 230. In this case, the other resources 250 may provide supplemental functions for components of the system 200 such as firmware upgrades, user interfaces, and storage and/or pre-processing of data from the physiological monitor 206 before transmission to the remote server 230.

The other resources 250 may also or instead include one or more web servers that provide web-based access to and from any of the other participants in the system 200. While depicted as a separate network entity, it will be readily appreciated that the other resources 250 (e.g., a web server) may also or instead be logically and/or physically associated with one of the other devices described herein, and may for example, include or provide a user interface 222 for web access to the remote server 230 or a database or other resource(s) to facilitate user interaction through the data network 202, e.g., from the physiological monitor 206 or the user device 220.

In another aspect, the other resources 250 may include fitness equipment or other fitness infrastructure. For example, a strength training machine may automatically record repetitions and/or added weight during repetitions, which may be wirelessly accessible by the physiological monitor 206 or some other user device 220. More generally, a gym may be configured to track user movement from machine to machine, and report activity from each machine in order to track various strength training activities in a workout. The other resources 250 may also or instead include other monitoring equipment or infrastructure. For example, the system 200 may include one or more cameras to track motion of free weights and/or the body position of the user during repetitions of a strength training activity or the like. Similarly, a user may wear, or have embedded in clothing, tracking fiducials such as visually distinguishable objects for image-based tracking, or radio beacons or the like for other tracking. In another aspect, weights may themselves be instrumented, e.g., with sensors to record and communicated detected motion, and/or beacons or the like to self-identify type, weight, and so forth, in order to facilitate automated detection and tracking of exercise activity with other connected devices.

One limitation on wearable sensors can be body placement. Devices are typically wrist-based, and may occupy a location that a user would prefer to reserve for other devices or jewelry, or that a user would prefer to leave unadorned for aesthetic or functional reasons. This location also places constraints on what measurements can be taken, and may also limit user activities. For example, a user may be prevented from wearing boxing gloves while wearing a sensing device on their wrist. To address this issues, physiological monitors may also or instead be embedded in clothing, which may be specifically adapted for physiological monitoring with the addition of communications interfaces, power supplies, device location sensors, environmental sensors, geolocation hardware, payment processing systems, and any other components to provide infrastructure and augmentation for wearable physiological monitors. Such "smart garments" offer additional space on a user's body for supporting monitoring hardware, and may further enable sensing techniques that cannot be achieved with single sensing devices. For example, embedding a plurality of physiological sensors or other electronic/communication devices in a shirt may allow electrocardiogram (ECG) based heart rate measurements to be gathered from a torso region of the wearer; wireless antennas to be placed above the upper portion of the thoracic spine to achieve desired communications signals; a contactless payment system to be embedded in a sleeve cuff for interactions with a payment terminal; and muscle oxygen saturation measurements to be gathered from muscles such as the pectoralis major, latissimus dorsi, biceps brachii, and other major muscle groups. This non-exhaustive list illustrates just some examples of technology that may be incorporated into a single garment.

Smart garments may also free up body surfaces for other devices. For example, if sensors in a wrist-worn device that provide heart rate monitoring and step counting can be instead embedded in a user's undergarments, the user may still receive the biometric information they desire, while also being able to wear jewelry or other accessories for suitable occasions.

The present disclosure generally includes smart garment systems and techniques. It will be understood that a "smart garment" as described herein generally includes a garment that incorporates infrastructure and devices to support, augment, or complement various physiological monitoring modes. Such a garment may include a wired, local communication bus for intra-garment hardware communications, a wireless communication system for intra-garment hardware communications, a wireless communication system for extra-garment communications and so forth. The garment may also or instead include a power supply, a power management system, processing hardware, data storage, and so forth, any of which may support enriched functions for the smart garment.

Figure 3:
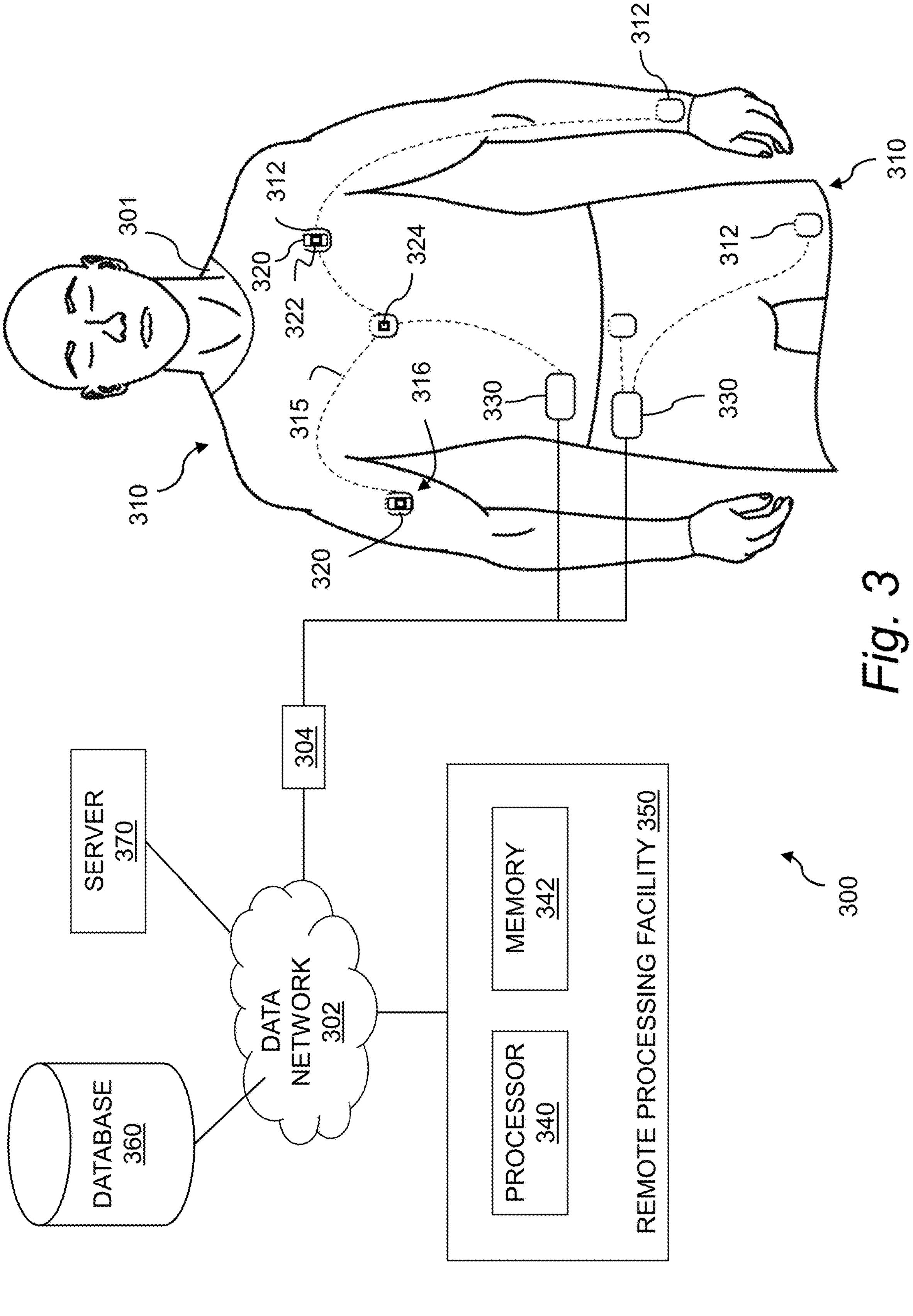
FIG. 3 shows a smart garment system.

FIG. 3 shows a smart garment system. In general, the system 300 may include a plurality of components—e.g., a garment 310, one or more modules 320, a controller 330, a processor 340, a memory 342, and so on—capable of communicating with one another over a data network 302. The garment 310 may be wearable by a user 301 and configured to communicate with a module 320 having a physiological sensor 322 that is structurally configured to sense a physiological parameter of the user 301. As discussed herein, the module 320 may be controllable by the controller 330 based at least in part on a location 316 where the module 320 is located on or within the garment 310. This position-based information may be derived from an interaction and/or communication between the module 320 and the garment 310 using various techniques. It will be understood that, while two controllers 330 are shown, the garment 310 may include a single inter-garment controller, or any number of separate controllers 330 in any number of garments 310 (e.g., one per garment, or one for all garments worn by a person, etc.), and/or controllers may be integrated into other modules 320.

For communication over the data network 302, the system 300 may include a network interface 304, which may be integrated into the garment 310, included in the controller 330, or in some other module or component of the system 300, or some combination of these. The network interface 304 may generally include any combination of hardware and software configured to wirelessly communicate data to remote resources. For example, the network interface 304 may use a local connection to a laptop, smart phone, or the like that couples, in turn, to a wide area network for accessing, e.g., web-based or other network-accessible resources. The network interface 304 may also or instead be configured to couple to a local access point such as a router or wireless access point for connecting to the data network 302. In another aspect, the network interface 304 may be a cellular communications data connection for direct, wireless connection to a cellular network or the like.

The data network 302 may generally include any communication network through which computer systems may exchange data. For example, the data network 302 may include, but is not limited to, the Internet, an intranet, a LAN (Local Area Network), a WAN (Wide Area Network), a MAN (Metropolitan Area Network), a wireless network, a cellular data network, an optical network, and the like. To exchange data via the data network 302, the system 300 and the data network 302 may use various methods, protocols, and standards including, but not limited to, token ring, Ethernet, wireless Ethernet, Bluetooth, TCP/IP, UDP, HTTP, FTP, SNMP, SMS, MMS, SS7, JSON, XML, REST, SOAP, CORBA, IIOP, RMI, DCOM and Web Services. To ensure data transfer is secure, the system 300 may transmit data via the data network 302 using a variety of security measures including, but not limited to, TSL, SSL and VPN. By way of example, some embodiments of the system 300 may be configured to stream information wirelessly to a social network, a data center, a cloud service, and so forth.

In some embodiments, data streamed from the system 300 to the data network 302 may be accessed by the user 301 (or other users) via a website. The network interface 304 may thus be configured such that data collected by the system 300 is streamed wirelessly to a remote processing facility 350, database 360, and/or server 370 for processing and access by the user. In some embodiments, data may be transmitted automatically, without user interactions, for example by storing data locally and transmitting the data over available local area network resources when a local access point such as a wireless access point or a relay device (such as a laptop, tablet, or smart phone) is available. In some embodiments, the system 300 may include a cellular system or other hardware for independently accessing network resources from the garment 310 without requiring local network connectivity.

In one example, the network interface 304 may be configured to stream data using Bluetooth or Bluetooth Low Energy technology, e.g., to a nearby device such as a cell phone or tablet for forwarding to other resources on the data network 302. In another example, the network interface 304 may be configured to stream data using a cellular data service, such as via a 3G, 4G, or 5G cellular network. It will be understood that the network interface 304 may include a computing device such as a mobile phone or the like. The network interface 304 may also or instead include or be included on another component of the system 300, or some combination of these. Where battery power or communications resources can advantageously be conserved, the system 300 may preferentially use local networking resources when available, and reserve cellular communications for situations where a data storage capacity of the garment 310 is reaching capacity. Thus, for example, the garment 310 may store data locally up to some predetermined threshold for local data storage, below which data is transmitted over local networks when available. The garment 310 may also transmit data to a central resource using a cellular data network only when local storage of data exceeds the predetermined threshold.

The garment 310 may include one or more of a shirt (or other top), shorts/pants (or other bottom), an undergarment (e.g., undershirt, underwear, brassiere, and so on), a sock or other footwear, a shoe, a facemask, a hat or helmet (or other head adornment), a compression sleeve, a sweatband, kinesiology tape or elastic therapeutic tape, a glove, and the like. More generally, the garment 310 may include any type(s) of wearable clothing or adornment suitable for wearing by a user and retaining one or more sensing modules as contemplated herein.

The garment 310 may include one or more designated areas 312 for positioning a module to sense a physiological parameter of the user 301 wearing the garment 310. One or more of the designated areas 312 may be specifically tailored for receiving a module 320 therein or thereon. For example, a designated area 312 may include a pocket structurally configured to receive a module 320 therein. Also or instead, a designated area 312 may include a first fastener configured to cooperate with a second fastener disposed on a module 320. One or more of the first fastener and the second fastener may include at least one of a hook-and-loop fastener, a button, a clamp, a clip, a snap, a projection, and a void.

The designated areas 312 may include at least one of a torso region, a spinal region, an extremity region (e.g., one or more of an arm region such as a sleeve, and a leg region such as a pant leg), a waistband region, a cuff region, and so on. Also or instead, one or more of the designated areas 312 may include at least a region adjacent to one or more muscle groups of the user 301—e.g., muscle groups including at least one of the pectoralis major, latissimus dorsi, biceps brachii, and so on.

By placing a pocket or the like in one of these designated areas 312, a position of a module 320 can be controlled, and where an RFID tag, sensor, or the like is used, the designated area 312 can specifically sense when a module 320 is positioned there for monitoring, and can communicate the detected location to any suitable control circuitry. In this manner, a garment 310 may facilitate the installation of modules 320 in many different, discrete locations, the placement of which can be controlled by the configuration of the garment 310, and the use of which can be automatically detected when corresponding control modules 320 are placed there for use. Also or instead, the garment 310 may facilitate the placing of the modules 320 over relatively large regions of the garment 310. For example, a garment 310 may include a relatively large region (in terms of surface area) where a module 320 can be affixed or otherwise secured, e.g., by loops, straps, buttons, sheets of hook-and-loop fasteners, and so forth.

In general, each designated area 312 may include a pocket such as any of those described above, or any other mounting fixture or combination of fixtures. Where a pocket is used, the pocket may be configured as describe above to preferentially urge a module 320 within the pocket toward the user's skin under normal pressure. Without limiting the generality of the foregoing, this may generally include an exterior layer of the pocket that is less elastic than an interior surface of the pocket so that when circumferential tension is applied (e.g., when the garment 310 is donned), the pocket preferentially urges a contact surface of the sensor inward toward the intended target surface with at least a predetermined normal force (when the garment 310 is properly sized for the user). In this respect, it will be understood that although some variation in normal force among users and garments is inevitable, typical tensions for comfortable use of properly fitted athletic wear are generally known, and adequate contact force to obtain a high quality physiological signal is generally known, and in any event readily observable in acquired data. As such, adequate circumferential tensions and resulting normal contact forces needed to promote good contact between sensing regions of the module 320 (such as LEDs, capacitive touch sensors, photodiodes, and the like) and the user's skin may readily be determined, and can advantageously facilitate the use of wrist-worn sensor housings such as those described above with one of the garments 310 described herein for off-wrist monitoring if/when desired.

In one aspect, the designated areas 312 may usefully be positioned where reinforcing clastic bands are typically provided on garments, e.g., around the mid-torso for a sports bra, around the waist on shorts or underwear, or on the sleeves of a t-shirt. In one aspect, the designated areas 312 may also usefully be positioned according to the intended physiological measurement, e.g., near major arteries suitable for heart rate detection using photoplethysmography. In one aspect, the garment 310 may usefully distribute these designated areas 312 (and supporting infrastructure such as wired connectors, location identification tags, and the like) at the intersection of regions where good physiological signals can be obtained and regions where adequate normal forces for good sensor contact can be generated by clothing. For example, this may include the ankles, the waist, the mid-torso, the biceps, the wrists, the forehead, and so on.

The garment 310 may also or instead incorporate other infrastructure 315 to cooperate with a module 320. For example, the garment infrastructure 315 may include wires or the like embedded in the garment 310 to facilitate wired data or power transfer between installed modules 320 and other system components (including other modules 320). The infrastructure 315 may also or instead include integrated features for, e.g., powering modules, supporting data communications among modules, and otherwise supporting operation of the system 300. The infrastructure may also or instead include location or identification tags or hardware, a power supply for powering modules 320 or other hardware, communications infrastructure as described herein, a wired intra-garment network, or supplemental components such as a processor, a Global Positioning System (GPS), a timing device, e.g., for synchronizing signals from multiple garments, a beacon for synchronizing signals among multiple modules 320, and so forth. More generally, any hardware, software, or combination of these suitable for augmenting operation of the garment 310 and a physiological monitoring system using the garment 310 may be incorporated as infrastructure 315 into the garment 310 as contemplated herein.

The modules 320 may generally be sized and shaped for placement on or within the one or more designated areas 312 of the garment 310. For example, in certain implementations, one or more of the modules 320 may be permanently affixed on or within the garment 310. In such instances, the modules 320 may be washable. Also or instead, in certain implementations, one or more of the modules 320 may be removable and replaceable relative to the garment 310. In such instances, the modules 320 need not be washable, although a module 320 may be designed to be washable and/or otherwise durable enough to withstand a prolonged period of engagement with a designated area 312 of the garment 310. A module 320 may be capable of being positioned in more than one of the designated areas 312 of the garment 310. That is, one or more of the plurality of modules 320 may be configured to sense data using a physiological sensor 322 in a plurality of designated areas 312 of the garment 310.

Removable and replaceable modules 320 may provide several advantages such as case of garment care (e.g., washing) and power management (e.g., removal for recharging). Furthermore, removability may facilitate replacement and/or repositioning of modules within the garment 310 for different sensing activities or other reconfigurations, replacement of damaged or defective modules 320, and so forth.

A module 320 may include one or more physiological sensors 322 and a communications interface 324 programmed to transmit data from at least one of the physiological sensors 322. For example, the physiological sensors 322 may include one or more of a heart rate monitor, an oxygen monitor (e.g., a pulse oximeter), a thermometer, an accelerometer, a gyroscope, a position sensor, a Global Positioning System, a clock, a galvanic skin response (GSR) sensor, or any other electrical, acoustic, optical, or other sensor or combination of sensors and the like useful for physiological monitoring, environmental monitoring, or other monitoring as described herein. In one aspect, the physiological sensors 322 may include a conductivity sensor or the like used for electromyography, electrocardiography, electroencephalography, or other physiological sensing based on electrical signals. The data received from the physiological sensors 322 may include at least one of heart rate data, muscle oxygen saturation data, temperature data, movement data, position/location data, environmental data, temporal data, and so on.

In one aspect, a module 320 may be configured for use on multiple body locations. For example, the module 320 may be one of the wrist-worn sensors described above. The module 320 may be adapted for use with a garment 310 in various ways. In one aspect, the module 320 may have relatively smooth, continuous exterior surfaces to facilitate sliding into and out of a pocket, such as any of the pockets described herein, or any other suitable retaining structure(s). In another aspect, an LED and/or sensor region may protrude from a surface of the module 320 sufficiently to extend beyond a restraining garment material and into a contact surface of a user. The module 320 may also include hardware to facilitate such uses. For example, a module 320 may usefully incorporate a contact sensor for detecting contact with a user. However, the exposed contact surfaces of the module 320 may be different when retained by a wrist strap (or other limb strap) than when retained by a garment pocket. To facilitate multiple retaining modes, the module 320 may usefully incorporate two or more contact sensors (such as capacitive sensors or other touch sensors, switches, or the like) at two different locations, each positioned to detect contact with a wearer in a different retaining mode. For example, a module 320 may include a capacitive sensor adjacent to an optical sensing system that contacts the user's skin when the module 320 is retained with a wrist strap. The module 320 may also or instead optically detect contact when the capacitive sensor is covered by a garment fabric or the like that prevents direct skin contact, or a second capacitive sensor may be placed within another region exposed by the garment 310 retaining system. In another aspect, the garment 310 may include a capacitive sensor that provides a signal to the module 320, or to some other system controller or the like, when a region of the garment near the module 320 is in contact with a user's skin.

In one aspect, the physiological sensors 322 may include a heart rate monitor or pulse sensor, e.g., where heart rate is optically detected from an artery, such as the radial artery. In one embodiment, the garment 310 may be configured such that a module 320 is positioned on a user's wrist, where a physiological sensor 322 of the module 320 is secured over the user's radial artery or other blood vessel. Secure connection and placement of a pulse sensor over the radial artery or other blood vessel facilitates measurement of heart rate, pulse oxygen, and the like. It will be understood that this configuration is provided by way of example only, and that other sensors, sensor positions, and monitoring techniques may also or instead be employed without departing from the scope of this disclosure.

In some embodiments, heart rate data may be acquired using an optical sensor coupled with one or more light emitting diodes (LEDs), all in contact with the user 301. To facilitate optical sensing, the garment 310 may be designed to maintain a physiological sensor 322 in secure, continual contact with the skin, and reduce interference of outside light with optical sensing by the physiological sensor 322.

Thus, certain embodiments include one or more physiological sensors 322 configured to provide continuous measurements of heart rate using photoplethysmography or the like. The physiological sensor 322 may include one or more light emitters for emitting light at one or more desired frequencies toward the user's skin, and one or more light detectors for received light reflected from the user's skin. The light detectors may include a photo-resistor, a phototransistor, a photodiode, and the like. A processor may process optical data from the light detector(s) to calculate a heart rate based on the measured, reflected light. The optical data may be combined with data from one or more motion sensors, e.g., accelerometers and/or gyroscopes, to minimize or eliminate noise in the heart rate signal caused by motion or other artifacts. The physiological sensor 322 may also or instead provide at least one of continuous motion detection, environmental temperature sensing, electrodermal activity (EDA) sensing, galvanic skin response (GSR) sensing, and the like.

The system 300 may include different types of modules 320. For example, a number of different modules 320 may each provide a particular function. Thus, the garment 310 may house one or more of a temperature module, a heart rate/PPG module, a muscle oxygen saturation module, a haptic module, a wireless communication module, or combinations thereof, any of which may be integrated into a single module 320 or deployed in separate modules 320 that can communicate with one another. Some measurements such as temperature, motion, optical heart rate detection, and the like, may have preferred or fixed locations, and pockets or fixtures within the garment 310 may be adapted to receive specific types of modules 320 at specific locations within the garment 310. For example, motion may preferentially be detected at or near extremities while heart rate data may preferentially be gathered near major arteries. In another aspect, some measurements such as temperature may be measured anywhere, but may preferably be measured at a single location in order to avoid certain calibration issues that might otherwise arise through arbitrary placement.

In another aspect, the system 300 may include two or more modules 320 placed at different locations and configured to perform differential signal analysis. For example, the rate of pulse travel and the degree of attenuation in a cardiac signal may be detected using two or more modules at two or more locations, e.g., at the bicep and wrist of a user, or at other locations similarly positioned along an artery. These multiple measurements support a differential analysis that permits useful inferences about heart strength, pliability of circulatory pathways, and other aspects of the cardiovascular system that may indicate cardiac age, cardiac health, cardiac conditions, and so forth. Similarly, muscle activity detection might be measured at different locations to facilitate a differential analysis for identifying activity types, determining muscular fitness, and so forth. More generally, multiple sensors can facilitate differential analysis. To facilitate this type of analysis with greater precision, the garment infrastructure may include a beacon or clock for synchronizing signals among multiple modules, particularly where data is temporarily stored locally at each module, or where the data is transmitted to a processor from different locations wirelessly where packet loss, latency, and the like may present challenges to real time processing.

The communications interface 324 may be any as described herein, for example including any of the features of the network interface 304 described above. The communications interface 324 may be a separate device that provides the ability for the modules 320 to communicate with one another and/or with other components of the system 300), or there may be a central module that communicates with other modules 320 (or with another component of the system 300). It will be understood that communications may usefully be secured using any suitable encryption technology in order to ensure privacy and security of user data. This may, for example, include encryption for local (wired or wireless) communications among the modules 320 and/or controller 330 within the garment 310. This may also or instead include encryption for remote communications to a server and other remote resources. In one aspect, the garment 310 and/or controller 330 may provide a cryptographic infrastructure for securing local communications, e.g., by managing public/private key pairs for use in asymmetric encryption, authentication, digital signatures, and so forth. The keys for this infrastructure may also or instead be managed by an external, trusted third party.

The controller 330 may be configured, e.g., by computer executable code or the like, to determine a location of the module 320. This may be based on contextual measurements such as accelerometer data from the module 320, which may be analyzed by a machine learning model or the like to infer a body position. In another aspect, this may be based on other signals from the module 320. For example, signals from sensors such as photodiodes, temperature sensors, resistors, capacitors, and the like may be used alone or in combination to infer a body position. In another aspect, the location may be determined based on a proximity of a module 320 to a proximity sensor, RFID tag, or the like at or near one of the designated areas 312 of the garment 310. Based on the location, the controller 330 may adapt operation of the module 320 for location-specific operation. This may include selecting filters, processing models, physiological signal detections, and the like. It will be understood that operations of the controller 330, which may be any controller, microcontroller, microprocessor, or other processing circuitry, or the like, may be performed in cooperation with another component of the system 300 such as the processor 340 described herein, one or more of the modules 320, or another computing device. It will also be understood that the controller 330 may be located on a local component of the system 300 (e.g., on the garment 310, in a module 320, and so on) or as part of a remote processing facility 350, or some combination of these. Thus, in an aspect, a controller 330 is included in at least one of the plurality of modules 320. And, in another aspect, the controller 330 is a separate component of the garment 310, and serves to integrate functions of the various modules 320 connected thereto. The controller 330 may also or instead be remote relative to each of the plurality of modules 320, or some combination of these.

Location detection (i.e., of the modules 320 and/or physiological sensors 322) may also usefully be recorded and used in a number of ways by a human user and/or by the system 300. For example, a detected location may be stored, along with the corresponding garment, so that a user can retrieve a placement history and replace the module 320 to a previous location for a particular garment as desired. In another aspect, the detected location may be used by the system 300 to analyze data and make garment specific recommendations. For example, the system 300 may evaluate the quality of a signal, e.g., using any conventional metrics such as signal-to-noise ratio, or using quality metrics more specific to physiological signals such as correlation to an expected signal or pulse shape, consistency with a rate or magnitude typical for a sensor, pulse-to-pulse consistency for a particular user, or any other measure of signal quality using statics, machine learning, digital signal processing techniques, or the like. A quality metric, however derived, may be used in turn to recommend specific placements of a module 320 on a garment 310 for a user, or to recommend a particular garment 310 for the user. Thus, for example, after acquiring data over a range of garments and activities, the system 300 may generate a user-actionable recommendation such as, "It appears that when you are jogging, the most accurate heart rate signals can be obtained when you are wearing an XL shirt model number xxxxxx. You may wish to wear this shirt for active workouts, and you may wish to purchase more of this type of shirt for regular use." As another example, the user-actionable recommendation may suggest: "It appears that one of your modules is not obtaining accurate temperature readings when located on your sleeve elastic band. You may wish to try a different location for this module, or to try a different garment." More generally, data quality may be measured for a number of different modules at different locations in different garments during different activities, and this data may be used to generate customized recommendations for a user on a per-garment and per-location basis. These recommendations may also be tailored to specific activity types where this data is accurately recorded by the system 300, either from user input, automatic detection, or some combination of these.

The controller 330 may be configured to control one or more of (i) sensing performed by a physiological sensor 322 of the module 320 and (ii) processing by the module 320 of the data received from a physiological sensor 322. That is, in certain aspects, the combination of sensors in the module 320 may vary based on where it is intended to be located on a garment 310. In another aspect, processing of data from a module 320 may vary based on where it is located on a garment 310. In this latter aspect, a processing resource such as the controller 330 or some other local or remote processing resource coupled to the module 320 may detect the location and adapt processing of data from the module 320 based on the location. This may, for example, include a selection of different models, algorithms, or parameters for processing sensed data.

In another aspect, this may include selecting from among a variety of different activity recognition models based on the detected location. For example, a variety of different activity recognition models may be developed such as machine learning models, lookup tables, analytical models, or the like, which may be applied to accelerometer data to detect an activity type. Other motion data such as gyroscope data may also or instead be used, and activity recognition processes may also be augmented by other potentially relevant data such as data from a barometer, magnetometer, GPS system, and so forth. This may generally discriminate, e.g., between being asleep, at rest, or in motion, or this may discriminate more finely among different types of athletic activity such as walking, running, biking, swimming, playing tennis, playing squash, and so forth. While useful models may be developed for detecting activities in this manner, the nature of the detection will depend upon where the accelerometers are located on a body. Thus, a processing resource may usefully identify location first using location detection systems (such as tags, electromechanical bus connections, etc.) built into the garment 310, and then use this detected location to select a suitable model for activity recognition. This technique may similarly be applied to calibration models, physiological signals processing models, and the like, or to otherwise adapt processing of signals from a module 320 based on the location of the module 320.

Determining the location of a module 320 may include receiving a sensed location for the module 320. The sensed location may be provided by a proximity detection circuit such as a near-field-communication (NFC) tag, an (active or passive) RFID tag, a capacitance sensor, a magnetic sensor, an electrical contact, a mechanical contact, and the like. Any corresponding hardware for such proximity detections may be disposed on the module 320 and the garment 310 for communication therebetween to detect location when appropriate. For example, in one aspect, an NFC tag may be disposed on or within the garment 310, and the module may include an NFC tag sensor that can detect the tag and read any location-specific information therefrom. Proximity detection may also or instead be performed using capacitively detected contact, electromagnetically detected proximity, mechanical contact, electrical coupling, and the like. In this manner, a garment 310 may provide information to an installed module 320 to inform the module 320, among other things, where the module 320 is located, or vice-versa.

Thus, communication between a module 320 and the garment 310 (or a processor of the garment 310) may be used to determine the location of a module 320 on the garment 310. Communication of location information may be enabled using active techniques, passive techniques, or a combination thereof. For example, a thin, flexible, cheap, washable NFC tag may be sewn into the garment 310 in various locations where a module 320 may be placed. When a module 320 is placed in the garment 310, the module 320 may query an adjacent NFC tag to determine its location. Furthermore, the NFC technique or other similar techniques may provide other information to the module 320, including details about the garment 310 such as the size, whether it is a gender specific piece, the manufacturer information, model or serial number of the garment, stock keeping unit (SKU), and more. Similarly, the tag may encode a unique identifier for the garment 310 that can be used to obtain other relevant information using an online resource. The module 320 may also or instead advertise information about itself to the garment 310 so that the garment 310 can synchronize processing with other modules 320, synchronize communication among modules 320, control or condition signals from the module 320, and so forth. The module 320 can then configure itself within the context of the current garment 310 and associated modules 320, and/or to perform certain types of monitoring or data processing.

Determining the location of a module 320 may also or instead be based, at least in part, on an interpretation of the data received from a physiological sensor 322 of the module 320. By way of example, movement of a module 320 as detected by a sensor may provide information that can be used to predict a position on or within the garment 310. Also or instead, the type of data that is being received from a module 320 may indicate where the module 320 is located on the garment 310. For example, locations may produce unique signatures of acceleration, gyroscope activity, capacitive data, optical data, temperature data, and the like, depending on where the module 320 is located, and this data may be fused and analyzed in any suitable manner to obtain a location prediction.

According to the foregoing, determining the location of a module 320 may also or instead include receiving explicit input from the user 301, which may identify one of the designated areas on the garment 310, or a general area of the body (e.g., left wrist, right ankle, and so forth). Because the location of the module 320 relative to the garment 310 may be determined from an analysis of a plurality of data sources, the system 300 may include a component (e.g., the processor 340) that is configured to reconcile one or more potential sources of location of information based on expected reliability, measured quality of data, express user input, and so forth. A prediction confidence may also usefully be generated in this context, which may be used, for example, to determine whether a user should be queried for more specific location information. More generally, any of the foregoing techniques may be used along or in combination, along with a failsafe measure the requests user input when location cannot confidently be predicted. Also or instead, a user may explicitly specify a prediction preemptively, or as an override to an automatically generated prediction.

Once determined using any of the techniques above, the location of a module 320 may be transmitted for storage and analysis to a remote processing facility 350, a database 360, or the like. That is, in addition to the module 320 using this information locally to configure itself for the location in which it is worn, the module 320 may communicate this information to other modules 320, peripherals, or the cloud. Processing this information in the cloud may help an organization determine if a module 320 has ever been installed on a garment 310, which locations are most used, and how modules 320 perform differently in different locations. These analytics may be useful for many purposes, and may, for example, be used to improve the design or use of modules 320 and garments 310, either for a population, for a user type, or for a particular user.

As stated above, the system 300 may further include a processor 340 and a memory 342. In general, the memory 342 may bear computer executable code configured to be executed by the processor 340 to perform processing of the data received from one or more modules 320. One or more of the processor 340 and the memory 342 may be located on a local component of the system 300 (e.g., the garment 310, a module 320, the controller 330, and the like) or as part of a remote processing facility 350 or the like as shown in the figure. Thus, in an aspect, one or more of the processor 340 and the memory 342 is included on at least one of the plurality of modules 320. In this manner, processing may be performed on a central module, or on each module 320 independently. In another aspect, one or more of the processor 340 and the memory 342 is remote relative to each of the plurality of modules 320. For example, processing may be performed on a connected peripheral device such as smart phone, laptop, local computer, or cloud resource.

The memory 342 may store one or more algorithms, models, and supporting data (e.g., parameters, calibration results, user selections, and so forth) and the like for transforming data received from a physiological sensor 322 of the module 320. In this manner, suitable models, algorithms, tuning parameters, and the like may be selected for use in transforming the data based on the location of the module 320 as determined by the controller 330 and/or processor 340 as described herein. By way of example, algorithms that convert data from an accelerometer in a module 320 into a count of a user's steps may be different depending on whether the module 320 is worn on the user's wrist or on the user's waist band. Similarly, the intensity of an LED and corresponding sensitivity of a photodetector may be different for a PPG device placed on the wrist or the thigh. Thus, the module 320 may self-configure for a location by controlling one or more of sensor types, sensor parameters, processing models, and so forth based on a detected location for the module 320.

Selection of an algorithm may also or instead include an analysis of one or more of the sensor data, metadata, and the like. By way of example, an algorithm may be selected at least in part based on metadata received from one of the module 320 and the garment 310. This metadata may be derived from communication between the module 320 and the garment 310—e.g., between a tag and tag reader for exchanging information therebetween. For example, the garment 310 may include, e.g., stored in a tag such as an NFC tag or other wirelessly readable data source, garment-specific metadata that is readable by or otherwise transmittable to one or more of the plurality of modules 320, the controller 330, and the processor 340. Such garment-specific metadata may include at least one of a type of garment 310, a size of the garment 310, garment dimensions, a gender configuration of the garment 310, a manufacturer, a model number, a serial number, a SKU, a material, fit information, and so on. In one aspect, this information may be provided with one or more of the location identification tags described herein. In another aspect, the garment 310 may include an additional tag at a suitable location (e.g., near or accessible to a processor or controller) that provides garment-specific information while other tags provide location-specific information.

The metadata may also or instead include at least one of a gender of the user 301, a weight of the user 301, a height of the user 301, an age of the user 301, metadata associated with the garment 310 (e.g., the garment size, type, material, etc.), and the like. The metadata may be derived, at least in part, from user-provided input, or otherwise from information derived from the user 301 such as a user's account information as a participant in the system 300. By way of example, a processing algorithm may be selected depending on the material of the garment 310 as communicated by its serial or model number in an identification tag, the physiology of the user 301 as implied by the garment size, and so on. The metadata may also or instead be used to verify the authenticity of the garment 310, and otherwise control access to the garment 310 and/or modules 320 coupled to the garment 310. In one aspect, metadata (e.g., size, material) may be encoded directly into the garment metadata. In another aspect, the garment 310 may publish a unique identifier that can be used to retrieve related information from a manufacturer or other data source. This latter approach advantageously permits correlation of garment-specific data with other user-specific data such as height, weight, body composition, and so forth.

Simply knowing a priori where a module 320 is positioned may allow for the use of algorithms that have been developed to perform optimally in that particular location. This can relieve a significant computational burden otherwise borne by the module 320 to analytically evaluate location based on available signals. Other information may also or instead be used to select an optimal algorithm. For example, based on the gender or dimensions of a garment, the algorithm may employ different models or different model parameters.

The processor 340 may be configured to assess the quality of the data received from a physiological sensor 322 of the module 320. For example, the processor 340 may be configured to provide, based on the quality of the data, a recommendation regarding at least one of the location of a module 320 and an aspect of the garment 310 (e.g., size, fit, material, and so on). For example, the processor 340 may be configured to detect when the garment does not properly fit the wearer for acquisition of physiological data, for example, by detecting when a module is moving (e.g., from accelerometer data) but data quality is poor or absent for a sensed physiological signal. In general, the garment 310 may store its own identifier and/or metadata, e.g., as described herein, or garment identification data may be stored in tags, e.g., at designated areas 312 of the garment 310. The processor 340 may be configured to use this garment identification information and/or metadata to provide a recommendation regarding a different garment 310 for the user 301, or for an adjustment to the current garment 310. For example, if a particular garment 310 seems to result in low-quality data, the user 301 could be encouraged to select an alternative size, or to make some other adjustment. Moreover, data on how many times a garment 310 is used may be gathered and used to inform business decisions, for example, which garments 310 provide the highest-quality data, and which garments 310 are most preferred by users 301.

The system 300 may further include a database 360, which may be located remotely and in communication with the system 300 via the data network 302. The database 360 may store data related to the system 300 such as any discussed herein—e.g., sensed data, processed data, transformed data, metadata, physiological signal processing models and algorithms, personal activity history, and the like. The system 300 may further include one or more servers 370 that host data, provide a user interface, process data, and so forth in order to facilitate use of the modules 320 and garments 310 as described herein.

It will be appreciated that the garment 310, modules 320, and accompanying garment infrastructure and remote networking/processing resources, may advantageously be used in combination to improve physiological monitoring and achieve modes of monitoring not previously available.

One or more of the devices and systems described herein may include circuitry for both wireless charging and wireless data transmission, e.g., where the corresponding circuits can operate independently from one another, and where the corresponding antennae are located proximal to one another (for instance, the circuitry for wireless charging and the circuitry for wireless data transmission may include separate coils disposed substantially along the same plane, or otherwise in relative close proximity in a device or system). In such aspects, one or more measures may be taken so that a wireless data transfer process does not interfere with a wireless power transfer process, more specifically by coupling the data circuitry into the electromagnetic field for the wireless power transfer in a manner that alters the resonant frequency or otherwise destructively interferes with power transfer, thereby decreasing efficiency when charging a device. For example, a switch may be included to disable circuitry for data transmission when certain wireless charging activity is present, thereby allowing for relatively unimpeded and efficient wireless charging of a device. The switch may also be operable to enable operation of data transmission circuitry when certain wireless charging activity is not present.

Thus, for example, in the context of a physiological monitor, such as any of those described herein, the physiological monitor may include both a wireless power receiver (or similar) and a wireless data tag reader (or similar). In general, these sub-systems may conform to one or more Near Field Communication (NFC) specifications for protocols and physical architectures, or any other standards suitable for wireless power and data transmission. The power circuitry may be used, e.g., to charge a battery on the physiological monitor so that the device can be recharged without physically connecting to a power source. The data circuitry may be used, e.g., as a wireless data tag reader or the like to read data from nearby data sources such as identification tags in user apparel and the like. In general, the physiological monitor may include separate circuitry (separate coils) for these wireless power and data systems, such as separate processing circuitry and/or separate antennae. The antennae may be disposed substantially along the same plane of the physiological monitor (e.g., with one coil disposed substantially inside or adjacent to the other). In one aspect, the antennae may be in parallel planes, however, it will be noted that distance tolerances for NFC standard devices are relatively small, and the physically housing for these antennae will preferably enforce an identical or substantially identical distance for both antennae in such architectures. In this context, the positions of the antennae may be as close to parallel as possible within reasonable manufacturing tolerances, or as close to parallel as possible when disposed on two different layers of a shared printed circuit board, or preferably, when disposed on a single layer of a shared printed circuit board. The physiological monitor may further include a switch (e.g., a radio frequency (RF) switch or the like) in-line with the coil for the wireless data tag reader to disable the wireless data tag reader when power is being received to mitigate any effects on the efficiency of the wireless power transfer process. In particular, the switch may be configured to open when power is being received, and may be configured to close when the physiological monitor is looking for data tag to read.

Figure 4:
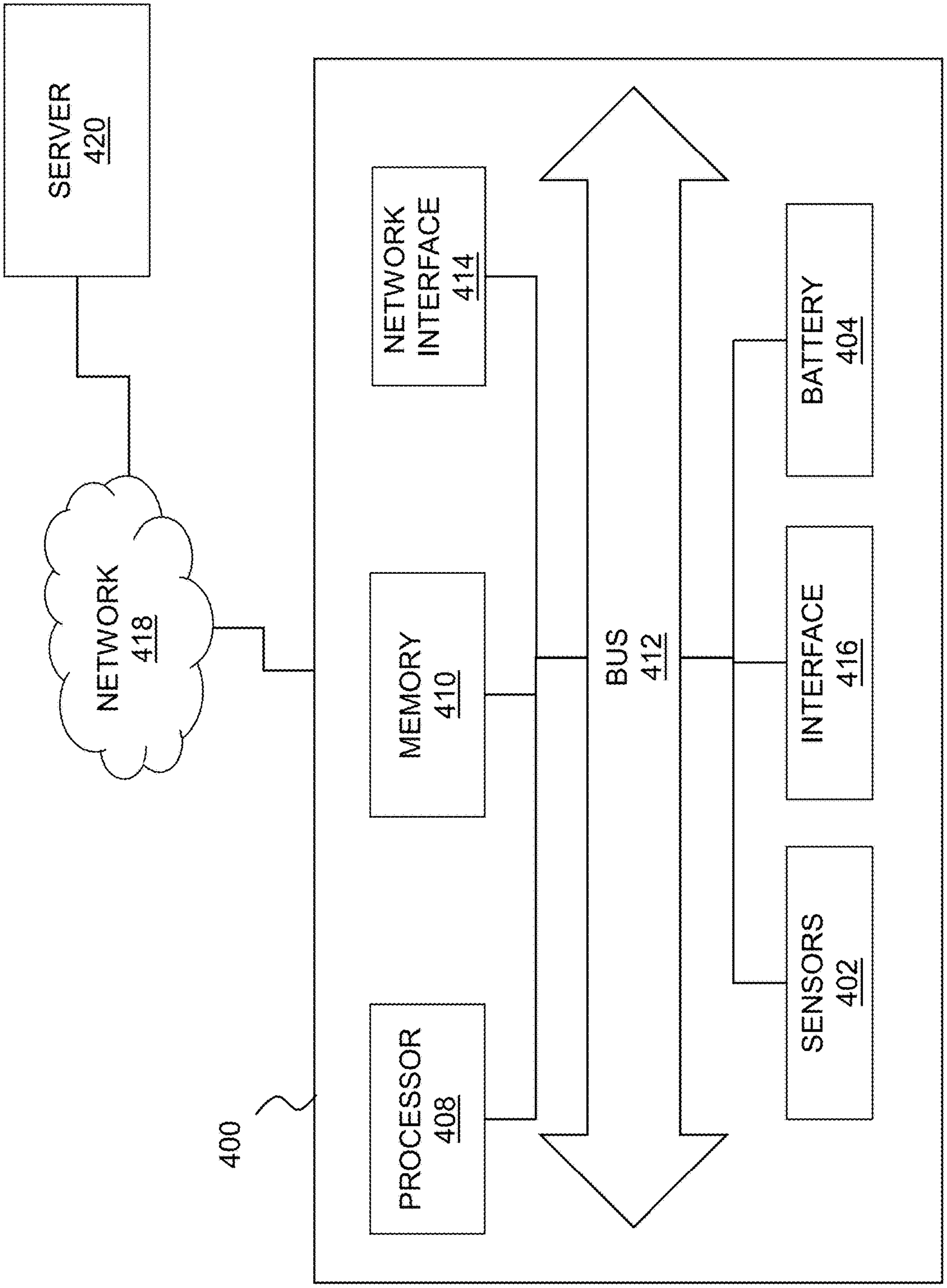
FIG. 4 is a block diagram of a computing device.

FIG. 4 is a block diagram of a computing device 400. The computing device 400 may, for example, be a device used for continuous physiological monitoring, or any other device supporting a physiological monitor in the systems and methods described herein. The device may also or instead be any of the local computing devices described herein, such as a desktop computer, laptop computer, smart phone, Internet-of-Things (IoT) device (e.g., smart home system, audio system, thermostat, connective television, exercise device, and so forth), or other local computing device that might be used by a user as a physiological monitoring device, or in combination with a physiological monitoring device. The device may also or instead be any of the remote computing resources described herein, such as a web server, a cloud database, a file server, an application server, or any other remote resource or the like. While described as a physical device, it will be understood that the exemplary computing device 400 may also or instead be realized as a virtual computing device such as a virtual machine executing a web server or other remote resource in a cloud computing platform. In general, the device 400 may include one or more sensors 402, a battery 404, storage, a processor 408, memory 410, a network interface 414, and a user interface 416, or virtual instances of one or more of the foregoing.

The sensors 402 may include any sensor or combination of sensors suitable for heart rate monitoring as contemplated herein, as well as sensors 402 for detecting calorie burn, position (e.g., through a Global Positioning System or the like), motion, activity and so forth. In one aspect, this may include optical sensing systems including LEDs or other light sources, along with photodiodes or other light sensors, that can be used in combination for photoplethysmography measurements of heart rate, pulse oximetry measurements, and other physiological monitoring.

The sensors 402 may also or instead include one or more sensors for activity measurement. In some embodiments, the system may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the wearable system may include a multi-axis accelerometer to measure motion and calculate distance. Motion sensors may be used, for example, to classify or categorize activity, such as walking, running, performing another sport, standing, sitting or lying down. The sensors 402 may, for example, include a thermometer for monitoring the user's body or skin temperature. In one embodiment, the sensors 402 may be used to recognize sleep based on a temperature drop, Galvanic Skin Response data, lack of movement or activity according to data collected by the accelerometer, reduced heart rate as measured by the heart rate monitor, and so forth. The body temperature, in conjunction with heart rate monitoring and motion, may be used, e.g., to interpret whether a user is sleeping or just resting, as well as how well an individual is sleeping. The body temperature, motion, and other sensed data may also be used to determine whether the user is exercising, and to categorize and/or analyze activities as described in greater detail below. In another aspect, the sensors 402 may include one or more contact sensors, such as a capacitive touch sensor or resistive touch sensor, for detecting placement of a physiological monitor for use on a user. More generally, the sensors 402 may include any sensor or combination of sensors suitable for monitoring geographic location, physiological state, exertion, movement, and so forth in any manner useful for physiological monitoring as contemplated herein.

The battery 404 may include one or more batteries configured to allow continuous wear and usage of the wearable system. In one embodiment, the wearable system may include two or more batteries, such as a removable battery that may be removed and recharged using a charger, along with an integral battery that maintains operation of the device 400 while the main battery charges. In another aspect, the battery 404 may include a wireless rechargeable battery that can be recharged using a short range or long range wireless recharging system.

The processor 408 may include any microprocessor, microcontroller, signal processor or other processor or combination of processors and other processing circuitry suitable for performing the processing steps described herein. In general, the processor 408 may be configured by computer executable code stored in the memory 410 to provide activity recognition and other physiological monitoring functions described herein.

In general the memory 410 may include one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, optical disks, USB flash drives), and the like. In one aspect, the memory 410 may include a computer system memory or random access memory, such as DRAM, SRAM, EDO RAM, and the like. The memory 410 may include other types of memory as well, or combinations thereof, as well as virtual instances of memory, e.g., where the device is a virtual device. In general, the memory 410 may store computer readable and computer-executable instructions or software for implementing methods and systems described herein. The memory 410 may also or instead store physiological data, user data, or other data useful for operation of a physiological monitor or other device described herein, such as data collected by sensors 402 during operation of the device 400.

The network interface 414 may be configured to wirelessly communicate data to a server 420, e.g., through an external network 418 such as any public network, private network, or other data network described herein, or any combination of the foregoing including, e.g., local area networks, the Internet, cellular data networks, and so forth. Where the device is a physiological monitoring device, the network interface 414 may be used, e.g., to transmit raw or processed sensor data stored on the device 400 to the server 420, as well as to receive updates, receive configuration information, and otherwise communicate with remote resources and the user to support operation of the device. More generally, the network interface 414 may include any interface configured to connect with one or more networks, for example, a Local Area Network (LAN), a Wide Area Network (WAN), the Internet, or a cellular data network through a variety of connections including, but not limited to, standard telephone lines, LAN or WAN links (for example, 802.11, T1, T3, 56 kb, X.25), broadband connections (for example, ISDN, Frame Relay, ATM), wireless connections, or some combination of any or all of the above. The network interface 412 may include a built-in network adapter, network interface card, PCMCIA network card, card bus network adapter, wireless network adapter, USB network adapter, modem or any other device suitable for interfacing the computing device 400 to any type of network capable of communication and performing the operations described herein.

The user interface 416 may include any components suitable for supporting interaction with a user. This may, for example, include a keypad, display, buzzer, speaker, light emitting diodes, and any other components for receiving input from, or providing output to, a user. In one aspect, the device 400 may be configured to receive tactile input, such as by responding to sequences of taps on a surface of the device to change operating states, display information and so forth. The user interface 416 may also or instead include a graphical user interface rendered on a display for graphical user interaction with programs executing on the processor 408 and other content rendered by a physical display of device 400.

An aspect of the invention is a system and method for allowing a user to intelligently query the physiological monitoring system in order to provide personalized, and readily understandable, responses. As described in detail below the system takes a user's input query and utilizes context-driven prompt engineering in order to generate a query which is supplied to a large language model (LLM). The output is provided as a natural language output which is therefore easy to understand for the user.

Figure 5:
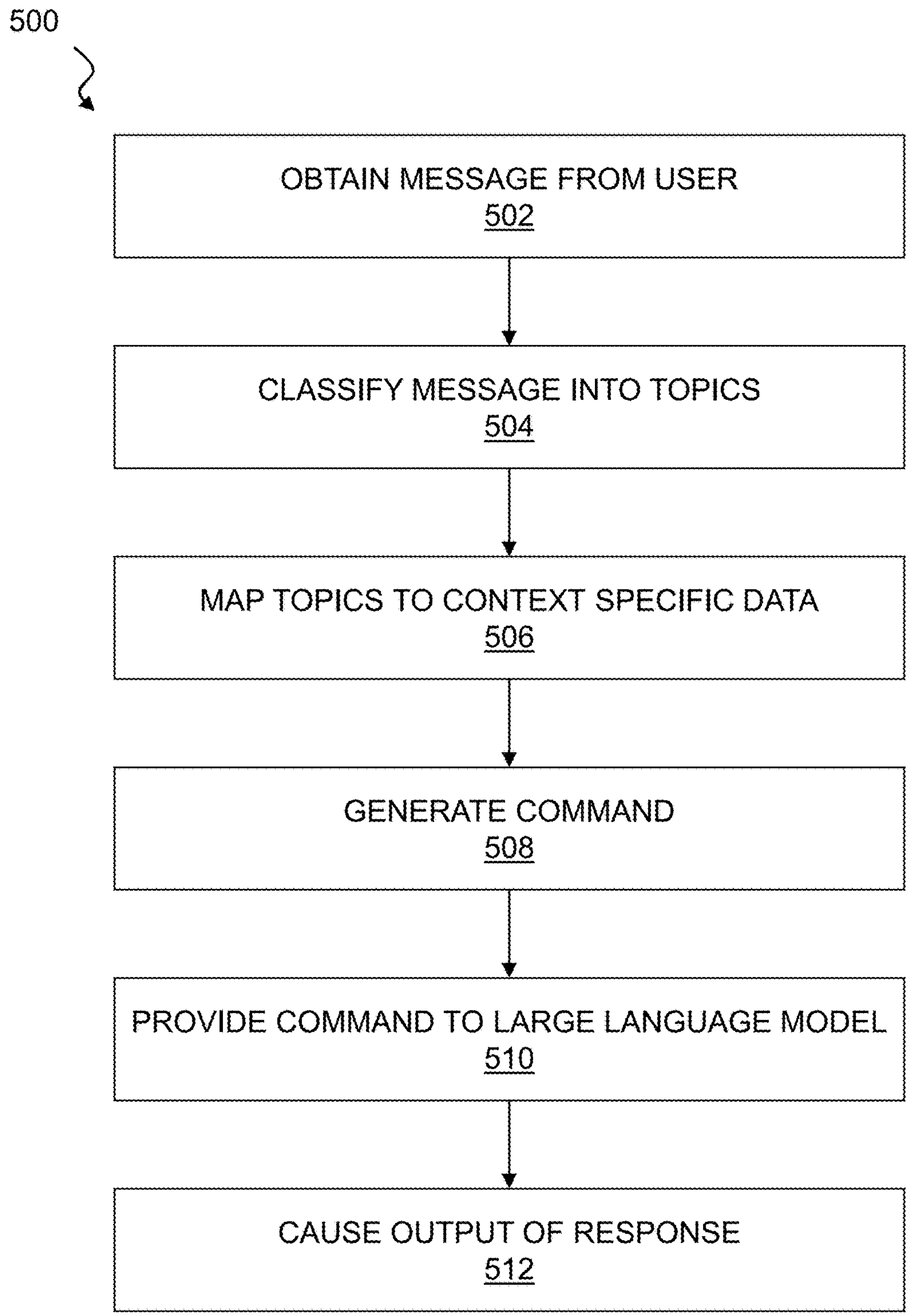
FIG. 5 shows a method for context-driven prompt engineering.

FIG. 5 is a flow chart illustrating a method 500 for context-driven prompt engineering to generate a natural language response to a user query. The method 500 may be used in cooperation with any of the devices, systems, and methods described herein, such as by a user device (e.g., a mobile device) that is communicatively coupled to a wearable, continuous physiological monitoring device and/or a remote server, such as the one or more user devices 220 that are communicatively coupled to the physiological monitor 206 in FIG. 2. In general, the method 500 generates a command for a large language model (LLM) or other inference engine or the like by dynamically incorporating context data relating to a user query into the command. Context data for to the user query may be generated from static and dynamic data sources related to the physiological monitoring system. This context data is used to generate a context portion of a command for the LLM. The command also includes an instruction portion that comprises instructions to direct the LLM to perform a rephrasing of the context data within the context portion. The LLM then produces a natural language rephrasing of the context portion that can be output to the user as a response to the user query.

Beneficially, the method 500 provides a mechanism for incorporating contextual data related to a physiological monitoring system into a response generated by a large language model without requiring the large language model (LLM) to be trained on, or have access to, large amounts of data related to the physiological monitoring system. In one aspect, limited context data may be selected and provided to the LLM along with specific instructions on how to use the context data. Additionally, portions of the data related to the physiological monitoring system may be personal data and dissemination of the data may be undesirable. Therefore, using the method 500, a personalized response to a user query may be generated without exposing personal and/or protected information related to the user to the LLM. For example, in another aspect, a query to the LLM may include instructions to provide a response with functional code that can retrieve context data, e.g., personal data or the like, when the response is rendered for a user. In another aspect, the method 500 efficiently identifies context data that may be relevant to a user's query thereby making more efficient use of the limited input that may be provided to an LLM. Moreover, the response obtained from the LLM may be augmented with one or more elements such as images, proprietary data, and/or interactive elements to provide a content rich response to the user. More generally, context data such as personal data or other user-specific data may usefully be integrated into a generative query-response system in a number of ways, such as by retrieving specific user data for formulation of a response to a particular LLM query, and/or by providing instructions to an LLM on how to generate a response with functional code that can incorporate user-specific context data when the response is presented to the user so that the LLM does not receive any personal data or the like.

As shown in step 502, the method 500 may include obtaining a message from a user of a physiological monitoring system. The message includes a query associated with the physiological monitoring system.

In one embodiment, the method 500 may include, prior to step 502, generating and displaying suggested questions for the user to pose in step 502. Upon the user opening a screen for providing messages (e.g., the screen used to obtain the message at step 502), the system may prompt an LLM to write suggested messages based on a pre-defined set of messages provided to the LLM. Additionally, or alternatively, the system may prompt the LLM to write suggested messages based on embeddings to identify clusters or types of messages that are most relevant or popular or engaging. Additionally, or alternatively, the system may prompt the LLM to write suggested messages based the content of the screen from which the user most immediately arrived, or had viewed within a predetermined time period (e.g. if the user was looking at a screen with sleep data, then the LLM would be prompted to suggest questions about sleep). Other techniques may also or instead be used to suggest questions, such as presenting a curated, predetermined list of question, or generating a list of questions based on popularity with a population of users.

The message may be provided by the user to an input area, such as a text box, of a user interface running on the user device. The user interface may be served by a locally-executing application (e.g., an application running on the one or more user devices 220 shown in FIG. 2) or may be remotely served and presented on the user device (e.g., the user interface is provided from the remote server 230 or the one or more other resources 250 and presented on the user device 220). The message received from the user may be provided as part of a conversational, or chat-based, service comprising a sequence of user messages and subsequent responses (e.g., generated by the method 500). The message may be a text-based message provided by the user directly inputting the query into the input area of the user interface. Alternatively, the message may be an audio input comprising a spoken version of the user's query, or an image and/or video input. In such alternative scenarios, the message is converted to a text-based message using an appropriate conversion service such as a speech-to-text service, an image understanding service, or an optical character recognition (OCR) service.

The query included within the message may be understood as corresponding to a request, or question, for which the user seeks a response. For example, the user may provide a message containing the query, "how did I sleep last night?". Alternatively, the message may include more than one query. For example, the user may provide a message asking, "how did I sleep last night? Was I awake at all?", which thus includes the queries "how did I sleep last night?" and "Was I awake at all?". The method 500 provides a natural language response to the query, or queries, based on context data related specifically to the user and topics identified as being related to the query, or queries.

In one embodiment, the message is checked against a content policy prior to the method 500 proceeding to step 504. The content policy may define that the message should not relate to, or contain, inappropriate, offensive, malicious, and/or dangerous content. If the message is deemed to satisfy the content policy, then the method 500 proceeds to step 504. If the message is deemed to violate the content policy (i.e., the message is deemed to relate to, or contain, inappropriate, offensive, malicious, and/or dangerous content) then the method 500 may terminate, and a response may be provided to the user to indicate that no response has been generated for the query. Here, the response provided to the user may take the form of a warning message, error message, or alert. The response may indicate what portions of the message were deemed to violate the content policy. The message may be checked against the content policy using any suitable classification or moderation approach. In one implementation, the message is checked against the content policy using known third-party moderation services such as the moderation endpoint provided by the OpenAI platform API.

As shown in step 504, the method 500 may include classifying the message into one or more topics. Each of the one or more topics is associated with the query included in the message.

As stated above, the method 500 provides a natural language response to the query received from the user by identifying topics to which the query relates, and then obtaining context data relevant to the identified topics. The topics are thus used to identify what contextual data is needed to provide a response to the user's message. Here, a topic may be understood as a high-level category, theme, or subject. For example, the previous question, "how well did I sleep last night?" may relate to topics such as "sleep", "sleep quality", and "last night".

In some embodiments, the message is classified into the one or more topics using a hierarchy of topic classifiers. The hierarchy of topic classifiers may comprise a top-level classifier for classifying the message into one or more top level topics. Here, the top-level topics correspond to a set of broad topics to which the user's message may relate. Examples may include, "exercise", "sleep", "training", "information", "health", etc. The hierarchy of topic classifiers may further comprise one or more second-level classifiers. Each second-level classifier classifies the message into one or more topics within an associated top-level topic. For example, a second-level classifier associated with the top-level topic "sleep" may further classify the message into second-level topics, "sleep quality", "sleep duration", and the like. The hierarchy of topic classifiers may further comprise one or more third-level classifiers, each associated with a second level topic. As such, each level within the hierarchy of topic classifiers may further refine the set of possible topics to obtain one or more topics that are most likely to correspond to the user's query. The skilled person will appreciate that any number of classification levels may be used to refine the list of possible topics.

An individual topic classifier associated with a topic (e.g., "sleep", "fitness", etc.) may be represented as a function that takes the message, or a representation thereof, as input and provides an indication that the message relates to the topic as output. The output may be a binary "true" or "false" value, or the output may be a real-valued number indicative of the probability or likelihood that the message relates to the topic. A topic classifier may be implemented in several different ways. For example, a string matching algorithm may be employed to determine if the message contains text related to the topic. Additionally, or alternatively, a fuzzy rule based approach may be used to determine a membership degree value that may be converted to a "true" or "false" value based on where the membership degree value exceeds a predetermined threshold. Here the predetermined threshold may be any suitable value such as 0.8, 0.9, 0.95, or the like. An example scheme for the rules of the fuzzy rule based approach may be rules of the form, "IF text contains the word [first word] THEN degree value is [first degree value] BUT IT ALSO the text contains the word [second word] THEN degree value is [second degree value]"). In a further example, an embedding approach is used by a topic classifier to determine whether a message relates to the topic of the topic classifier. Example embedding approaches include the word2vec model or the lda2vec model. More generally, any suitable machine learning classifier or other classification technique may also or instead be used to classify one or more topics associated with the user query.

In an alternative embodiment, the message is classified into the one or more topics using a large language model (LLM). The LLM returns the one or more topics from an input comprising the message and a plurality of predetermined topics. The plurality of predetermined topics comprises a list of topics for which one or more mapping functions are available (as described in more detail below). The plurality of predetermined topics may be periodically updated and/or amended. In this embodiment, a prompt for the LLM may be generated with a first portion containing instructions informing the LLM of the requested task, a second portion containing the message, and a third portion containing the plurality of predetermined topics. The first portion may be any suitable prompt instructing the LLM to identify possible topics that the user's message may be related to. For example, the first portion may comprise the prompt, "You are a topic classifier. I am going to provide you with a list of topics and a message. Your job is to tell me if the message relates to any of the topics within the list of topics. If the message does relate to any of the topics, you are to provide a list of those topics." The LLM will then return a subset of the predetermined topics that are deemed to be related to the query within the user message. The subset may be an empty set if the LLM determines that the query does not relate to any of the predetermined topics.

The LLM used to classify the message into one or more topics may be any suitably trained large language model. The LLM may be a proprietary LLM that is internally deployed within and/or for the physiological monitoring system (e.g., as part of the other resources 250 shown in the physiological monitoring system 200 of FIG. 2). Alternatively, the LLM may be offered as a service by a third party. In such implementations, the LLM is accessible via one or more application programming interface (API) endpoints. The message may be classified into one or more topics by providing the relevant command or prompt to the API endpoint and obtaining a response containing the one or more topics (or an indication that no topics were identified). Example third party services include GPT-3 provided by OpenAI, Bloom by BigScience, and Google Bard.

In a further embodiment, the message is classified into the one or more topics using a combination of the hierarchical topic classification approach and the LLM approach. For example, a top-level classifier may be used to classify the message into one or more top-level topics. Each top-level topic may comprise a list of second-level topics to which the message may relate. The list of second-level topics may then be provided, along with an instruction portion and the user's message, to the LLM. As such, the top-level classifier may be used to filter the plurality of predetermined topics into a smaller subset of topics thus improving the performance of the LLM by limiting the search space of topics.

If it is determined at step 504 that the message does not relate to any of a plurality of predetermined topics then this indicates that the user may have provided a query for which the method 500 is unable to produce a response. For example, the user may have asked for information to which no contextual data is available or may have asked a query that is entirely unrelated to the physiological monitoring system. If step 504 is unable to classify the message into one or more topics, then the method 500 may terminate, and a response provided to the user indicating that the query cannot be answered. In another aspect, the user may be prompted for clarification or elaboration of the content of the initial user message.

In one embodiment, a determination is made after step 504 to determine if the message from the user relates to an ambiguous or complex query. Here, an ambiguous or complex query is identified by identifying whether the message relates to one or more predetermined topics that are known to require further processing for the query to be answered accurately or correctly. For example, the message from the user may contain the ambiguous query "Do I sleep better in the winter or in the summer?" which is open ended and requires multiple data points to be answered. To help resolve such ambiguous or complex queries, the determination made after step 504 determines if the message from the user has a predetermined ambiguity level by determining if any of the one or more topics identified at step 504 relate to known, predetermined, ambiguous or complex topics. Here, the known, predetermined, ambiguous or complex topics are a list of topics that are known to relate to complex or ambiguous queries. Examples of such topics include "strain", "recovery", and the like. If it is determined that the message from the user has a predetermined ambiguity level (i.e., the at least one of the one or more topics are identified as being one of the known ambiguous or complex topics), then the process described in relation to FIG. 9 below is used to resolve the ambiguous or complex information by generating at least one topic that is represented as a structured query in a query language. As described in more detail below in relation to FIG. 9, the structured query is generated using a large language model (LLM) based on the message from the user and a schema for the query language.

As shown in step 506, the method 500 may include mapping, using one or more mapping functions, the one or more topics to a set of context specific data. Each of the one or more mapping functions obtains context specific data associated with a respective topic of the one or more topics, the context specific data comprising static data, and/or dynamic data associated with the physiological monitoring system.

Generally, each topic identified at step 504 is associated with one or more mapping functions that are configured to identify and/or retrieve or otherwise obtain contextual data relevant to the associated topic. A mapping function may take one or more parameters, or input parameters, as input and return contextual data as output. The contextual data may be static data—e.g., data obtained from articles, static files, and the like—or dynamic data—e.g., data that is directly related to the user or the activity of the user. For example, step 504 may identify the topic "get_heartrate" within the user's message as associated with a mapping function that obtains dynamic data associated with the user's heartrate over a previous period of time (e.g., 10 minutes, 60 minutes, 1 day, etc.). The topic "get_heartrate" may be associated with a further mapping function that obtains static data associated with the topic of heartrate from knowledge base articles. Here, knowledge base articles correspond to a library of articles, or documents, associated with the operation, support, and/or functionality of the physiological monitoring system (e.g., technical papers, blog posts, wiki entries, support articles, etc.). Within the context of the present disclosure, the term "static data" refers to context specific data that generally remains fixed unless manually edited. Put another way, static data does not change dynamically and is globally accessible (i.e., it is not restricted or limited to a single user). Examples of static data include documents or portions obtained from knowledge base articles, blog articles, online encyclopedias, user manuals, and the like. The term "dynamic data" refers to context data that is specific for the user and dynamically changes (e.g., due to the activity or actions of the user). As such, the dynamic data obtained by a mapping function may comprise one or more metrics associated with the user of the physiological monitoring system. Additionally, the term dynamic data may include data such as local environmental data (weather, pollen, UV index etc.), geography (location, terrain, roads or trail infrastructure), availability of local facilities (gym, pool etc.), local event listings (group run, sport competition, support or affinity group), matching data (service providers matched to user need, individuals with shared interests or needs etc.), and/or data about likely interests based on profile information (e.g. user regularly plays soccer and so may also like frisbee, user regularly meditates and so may also like a sensory deprivation activity etc.).

As stated above, static data returned by a mapping function refers to data that generally remains fixed unless manually edited. Examples of such data include knowledge base articles, blog articles, product data sheets, fixed data tables (e.g., conversion tables, lookup tables, and the like), and product help files. A mapping function may return such static data by performing a vector-based search, or semantic search, to identify a relevant document associated with the topic of the mapping function. A vector based search compares a vector embedding associated with the topic of the mapping function to a plurality of vector embeddings associated with a corresponding plurality of documents within a database of documents. A single mapping function that performs a vector-based search may be used by providing a topic as an input parameter to the mapping function. The mapping function may return one or more documents from the database of documents that are deemed to relate to the topic as output. Semantic searching may occur using known semantic searching methodologies.

In one embodiment, the vector-based search is implemented by first obtaining a database of documents containing contextual data, or information. Each document within the database of documents is then assigned a unique index and a document embedding for the document is obtained. To perform document level encoding, a word or sentence embedding may first be performed for each word or sentence within the document, and the average of all the word or sentence embeddings taken as an embedding for the document. Any suitable encoding technique may be used such as word2vec, GloVe, or suitable pre-trained deep neural networks such as a pre-trained BERT model. Each document within the database of documents is thus associated with a unique index and an associated embedding (i.e., a vector representation). To identify any documents that may be relevant to a topic, the topic is encoded using the same approach as used to perform document level encoding to generate a query vector (e.g., word2vec, GloVe, etc.), and then a similarity search is performed to determine the similarity between the query vector and one or more vectors obtained from the database of documents. Any suitable similarity metric can be used such as the dot product, cosine similarity, or the like. In one implementation, a k-nearest neighbor approach is used to determine the k most similar documents within the database of documents based on the similarity between the query vector and the plurality of vectors associated with the plurality of documents. The value k may be set to any suitable value such as 1, 2, or 3, so as to return the first 1, 2, or 3 most similar documents within the database of documents. In one embodiment, a further threshold is applied to the results such that only documents that are determined to have a similarity to the query vector to be above the threshold are returned as static data related to the topic.

In one embodiment, all relevant static data related to a topic is obtained (e.g., as described above) and a data relevance classifier is used to determine the relevance, or appropriateness, of the returned static data such that only the static data deemed to be relevant or appropriate is retained. For example, if the set of static context data, ($d_1$, $d_2$, $d_3$) is obtained, then each of $d_1$, $d_2$, and $d_3$ are input to the data relevance classifier to determine whether the item of static context data should be retained. In one embodiment, the data relevance classifier is a large language model (LLM) such as the first LLM described above. The LLM is prompted with an item of static context data in conjunction with a question regarding the usefulness of the item of static context data (e.g., "Is this static content useful?"). The response obtained from the LLM is then used to determine whether the item of static context data should be included or excluded from the set of static data.

As stated above, dynamic data returned by a mapping function refers to data that is directly related to the user or the activity of the user. Examples of dynamic data include a user's heart rate, strain, sleep duration, respiratory rate, personal goals, recent exercise activity, journalling data, recovery data, stress data, health monitor data, activity data (strain, strength, and sleep), member information (e.g., how long the user has been a member, what membership level the user has, etc.), connectivity information (e.g., when was the last time the user was connected to the physiological monitoring system, etc.), and the like. As such, a mapping function that is configured to obtain dynamic data for a relevant topic may obtain such data from one or more components or services of the physiological monitoring system. For example, the physiological monitoring system may provide a number of API endpoints that can be used to obtain dynamic data for the user of the physiological monitoring system. Dynamic data may further include population-level data related to one or more other users. Because the data is recorded at a population-level, the data does not contain any identifying data related to the one or more users. Rather, the population-level data includes statistics (e.g., averages, standard deviations, etc.) obtained for a given metric (e.g., heart rate, strain, sleep duration, etc.) over a population or demographic of users. For example, a query "how does my resting heart rate compare to the average for others my age" may be classified as relating to at least the topics "heart_rate", "average_heart_rate_age", and "user_age". A first mapping function associated with "heart_rate" may determine the user's current heart rate, or average heart rate over a preceding period of time (e.g., last 10 minutes, 60 minutes, 1 day, etc.) A second mapping function associated with the topic "user_age" may return dynamic data indicating the user's age, or age range. A third mapping function associated with the topic "average_heart_rate_age" may take the user's age as an input parameter (as determined by the second mapping function) and return data indicating the average heart rate for similarly aged people.

In one embodiment, the dynamic data is obtained by a mapping function associated with a topic based on one or more parameters, or input parameters, provided to the mapping function. The one or more parameters may filter the range of dynamic data returned. For example, the one or more input parameters may include a date range such that the dynamic data is returned only for the date range (e.g., the user's resting heart rate over the last 5 minutes). Here, the date range may be determined by another mapping function. For example, step 504 may identify topics "yesterday" and "calories" from a user's query, and a first mapping function may return yesterday's date (e.g., in MM/DD/YYY form or the like) such that this date may be subsequently provided as an input parameter to a second mapping function related to the user's calorie intake thereby limiting the dynamic data returned by the second mapping function to the user's calorie intake on the relevant date. Such dynamic data mapping can ensure that the data obtained is relevant to the query and/or user.

The static and/or dynamic data returned by a mapping function may further comprise one or more contextual examples related to the topic associated with the mapping function. As will be described in more detail below, the one or more contextual examples act as a few-shot prompt for the LLM. As such, the contextual examples help the LLM to determine how best to use, format, or structure the context data when generating a natural language representation of the context data. A contextual example may comprise a data, or input, portion and an example, or output, portion. In general, the data, or input, portion comprises the example contextual data that may be provided to the LLM while the example, or output, portion comprises an example of the way in which the LLM should use, format, or structure the context data. In one embodiment, the contextual examples are generated as part of a continuous and active learning process based on feedback obtained from users. Additionally, or alternatively, the contextual examples are manually generated and provided by a system administrator or expert user. For example, a contextual example returned by a mapping function associated with the topic "strain" may comprise a data portion, {("user's strain is 15"), ("user's optimal strain is 13.5"), ("user is overreaching")}, and an example portion: {("Your optimal strain for today is 13.5", ("Your current strain level is 15 which means that you are over reaching")}. By providing this example to the LLM, the LLM is succinctly taught how to present a user's strain data when generating an output.

In one embodiment, at least one topic of the one or more topics is represented as a structured query in a query language (e.g., a code block) such that context data related to the at least one topic is obtained by evaluating (or executing) the structured query (or code block). In another embodiment, dynamic data may include code that is executable on a user's system to incorporate user-specific data into a response, rather than the user-specific data itself. This is described in more detail in relation to FIGS. 9 and 12 below. Using this technique, the mapping functions may be used, either alone or in combination with an LLM, to generate an executable code block that can be included in an LLM response, and used when presenting a reply to the user to retrieve relevant dynamic data such as user-specific data, personal data, or the like. In one aspect, the LLM may be specifically requested to generate code that can be executed by the user (or a component of the system accessed by the user) to incorporate user-specific data when presenting a response to the user. As a significant advantage, this approach avoids the need to provide the underlying personal data to an LLM, and can support dynamic access to data sources beyond the training corpus of the LLM so that answers can more generally be personalized for a user with exposing the user's personal data to external computing infrastructure.

In one embodiment, the context data generated at step 506 is aggregated. Aggregation of the context data may comprise concatenating or otherwise combining the results of each of the mapping functions called at step 504. For example, if a first mapping function is called and returns data $D_1$ and a second mapping function is called and returns data $D_2$, then the aggregated context data may be the set $[D_1, D_2]$. Additionally, or alternatively, the context data may be aggregated based on a score, probability, or likelihood associated with the context data. For example, the contact data may be filtered so that only data associated with a score, probability, or likelihood above a threshold value (e.g., 0.5, 0.75, 0.8, 0.9, etc.) is aggregated into the context data used at step 508. The score, probability, or likelihood may correspond to a probability or likelihood associated with the topic to which the context data relates. As stated above, the classification performed at step 504 may return a probability or likelihood for each topic that indicates the probability or likelihood that the user's message relates to that topic. The use of the probability or likelihood score therefore ensures that only relevant topics are selected in the context data. Thus, the context data may be aggregated so that only the context data that is most probable, or most likely, to be relevant to the user's query is used to generate the response. Alternatively, the score, probability, or likelihood corresponds to a score returned by the mapping function used to obtain or generate the context data. For example, the score may correspond to a similarity score determined for static data or a potential relevance score for dynamic data.

Additionally, or alternatively, the context data generated at step 506 is filtered for relevance. That is, to limit the amount of context data provided as part of the command passed to an LLM (as described below in relation to step 508), the set of context data generated at step 506 is filtered so as to retain the most relevant context data. To filter the set of context data, a relevance classifier is used to assess the relevance (usefulness or appropriateness) of each item of context data. For example, if the context data generated at step 506 comprises the set of context data, ($C_1$, $C_2$, $C_3$), then each of $C_1$, $C_2$, and $C_3$ are input to the relevance classifier to determine whether the item of context data should be retained. In one embodiment, the relevance classifier is a large language model (LLM), such as the first LLM described above. The LLM is prompted with an item of context data in conjunction with a question regarding the usefulness of the item of context data (e.g., "Is the following context data relevant or useful?"). The response obtained from the LLM is then used to determine whether the item of context data should be included or excluded from the set of context data. In this way, the context data may be efficiently reduced without losing relevant data for generating a response to the user's query.

As shown in step 508, the method 500 may include generating a command comprising a context portion and an instruction portion. The context portion is based on the set of context specific data determined at step 504. The instruction portion comprises instructions for a large language model (LLM) to perform a rephrasing task based on the context portion. The command thus acts as a dynamically generated prompt provided to the LLM.

The instruction portion comprises a predetermined instruction or prompt that provides the relevant instructions for the LLM to perform the requested rephrasing task. When generating the response to the command generated at step 508, the LLM is used to convert the provided data into a more natural, human readable form. As such, the LLM is not instructed or tasked with performing any calculations, data fetching or the like. The instruction portion may thus comprise a predetermined prompt that identifies to the LLM the task to be performed and the use to be made of the provided data. For example, the instruction portion may comprise the text, "WHOOP is a 24/7 performance coach that can answer any question the user has that relates to their fitness goals. WHOOP always refers to itself as 'WHOOP' and never uses personal pronouns such as I or me. WHOOP has access to the user's data including information about their Sleep, Strain, and Recovery. This data is collected through a physical wearable device called the WHOOP Sensor. WHOOP always responds in 3-4 sentences. WHOOP gives actionable advice to the user to help them meet their health and fitness goals. The advice is always tied back to the user's WHOOP data. Answer the user's question using only their data shown below. If there is not enough information, let them know you don't have that data. Today is {{today}}". Other suitable instruction portions may be used.

The context portion is based on the set of context specific data determined at step 504 and may thus comprise all context data determined at step 504 or a subset thereof (e.g., as a result of aggregating the context data). The context portion may be prefaced with text identifying the portion as containing context data. In one embodiment, the context portion further comprises the message obtained from the user at step 502. Additionally, or alternatively, the context portion may further comprise one or more previous messages obtained from the user or provided to the user in response to the user's message(s). The one or more previous messages may form a part of a conversation history that is recorded as part of the physiological monitoring system. The one or more previous message may comprise the n most recent messages within the conversation history (e.g., the 1, 2, or 3 most recent messages). The one or more previous messages may additionally, or alternatively, include less recent messages (e.g., messages received 1 day, 1 week, 1 month, etc. ago). Since such message are unlikely to be held within the most recent conversation history, they may be obtained by performing a vector-based search of historical conversations to identify messages that are deemed to be similar to the user's current message. In further embodiments other suitable searching methods, such as keyword searching, may be used. Including one or more previous messages advantageously provides a form of memory to the LLM so that the response generated by the LLM may incorporate information or data previously received from or presented to the user.

Any user specific data, proprietary data, or potentially sensitive data included within the context portion of the command may be removed, redacted, or obfuscated prior to sending the command to the LLM at step 510. Here, user specific data includes any personally identifiable information (PII) or other information that may identify a user such as name, user account number, email address, location, etc. Proprietary data and potentially sensitive data corresponds to data that may be used within the physiological monitoring system but may not pass outside the boundary of the system due to data protection, intellectual property, or other factors. User specific data, proprietary data, or potentially sensitive data may be removed as part of step 506. That is, mapping functions that obtain such data may exclude, or replace, such data from the context data provided as output. Additionally, or alternatively, such data is identified after the context data has been obtained as part of the command generation performed at step 508. Where the values that might be considered user specific data, proprietary data, or potentially sensitive data are known, it is possible to remove or replace these values within the context data after the context data has been obtained. In one embodiment, any user specific data, proprietary data, or potentially sensitive data is replaced by a relevant template token so that such data is not sent to the LLM but can be reincorporated into the response prior to the response being sent to the user. For example, the user's name may be replaced by the template token "[#USER_NAME]" or an obfuscated token such as "##!34aE9" such that if that template token is encountered within the response generated by the LLM, it can be replaced within the user's name in the output provided to the user.

In another aspect, the context portion and instruction portion of the command may include a request that the LLM return a code block that can be executed on the user's system to retrieve relevant context data when presenting a response to the user.

The command generated at step 508 may be supplemented by one or more sets of few-shot prompts to teach, or train, the LLM how to use, structure, or present the context data contained within the context portion. As stated above, a few-shot prompt may be returned as a contextual example provided as part of the output of a mapping function. Alternatively, and as described in more detail below, the few-shot prompt may be obtained from a conversation history between the user and the physiological monitoring system.

In one embodiment, the command generated at step 508 is generated in unstructured form. That is, the command comprises a plain-text representation of the various portions. In an alternative embodiment, the command generated at step 508 is generated in structured form. For example, the command may take the form of a JSON, XML, or other structured representation where each portion is identified using a respective key/value pair or tag, names, and attributes.

In one embodiment, the command generated at step 508 includes an optimization portion. The optimization portion comprises instructions for the LLM to limit the length of the generated output according to a computational load on the LLM. In some scenarios, the LLM may be concurrently processing a high volume of simultaneous/near simultaneous requests (e.g., 100 requests, 1000 requests, 10000 requests, etc.) which causes an overall reduction in the performance of the LLM. This reduction in LLM performance leads to an increase in wait time for a user to receive a response to their query. To optimize the performance of the system across all requests when the load on the LLM is high, the instructions in the optimization portion cause the LLM to limit the length (e.g., number of tokens) of the generated output. Performing this optimization across all requests helps reduce the computational load on the LLM and thus improve performance and response time across the system. As described in more detail below in relation to FIG. 11, the optimization portion may be generated by obtaining one or more load values indicative of the computational load on the LLM and then generating the optimization portion comprising instructions for the LLM to generate the text-based output according to an output length criterion that is based on the one or more load values. In one embodiment, users are segmented into two or more groups such that commands for users within a first group include the optimization portion (and thus have reduced length output) while commands for users within a second group do not include the optimization portion (and thus do not have reduced length output). In some embodiments, users within the second group do not include the optimization portion if there are a sufficient number of users within the first group to affect an optimization in overall performance of the LLM (e.g., at least 50% of the users, at least 75% of the users, etc.). In another aspect, the length of responses may be preemptively limited where a large number of requests are queued locally for submission to an LLM, e.g., in order to prevent reduced LLM performance before a large volume of request are made, rather than after an observable decrease in performance is detected.

As shown in step 510, the method 500 may include providing the command to the LLM and subsequently obtaining a text-based response from the LLM. The text-based response comprises a natural language representation of the set of context specific data.

The LLM used at step 510 may be any suitable large language model that can provide a natural language representation of the set of context specific data based on the command generated at step 508. Here, the natural language representation of the set of context specific data is generated by the LLM using the contextual data along with the data upon which it was trained. As such, the response generated by the LLM may go beyond a simple rephrasing of the context data leading to the generation of a novel response that may not completely match the context data. For example, the LLM may filter out some, or all, of the context data provided if deemed not relevant to the user's question. Additionally, or alternatively, the LLM may utilize data used to the train the LLM to augment the provided context data (e.g., generating a response such as, "based upon your HRV you should do . . . and here is some additional information sourced from the Mayo clinic . . . "). The LLM may be a proprietary LLM that is internally deployed within the physiological monitoring system (e.g., as part of the other resources 250 shown in the physiological monitoring system 200 of FIG. 2). Alternatively, the LLM may be offered as a service by a third party. In such implementations, the LLM is accessible via one or more application programming interface (API) endpoints. The text-based response may be obtained by providing the command to the API endpoint and subsequently obtaining a response containing the natural language rephrasing. Example third party services include GPT-3 or GPT-4 provided by OpenAI, Bloom by BigScience, and Google Bard.

As shown in step 512, the method 500 may include causing a response based on the text-based response to be output to the user. The response obtained from the LLM at step 510 may be formatted, transformed, and/or supplemented with additional graphics, elements, or information through the use of template tokens prior to being output to the user.

Although the LLM is able to provide a natural language rephrasing of the context portion, the response provided by the LLM is textual. That is, the response provided does not provide graphics, interactive elements, or other non-textual elements, or the LLM may not have access to the relevant graphical, interactive, etc. data to incorporate such data in the response. Moreover, some data, such as user specific or other identifiable data, may have been excluded from the context portion of the command generated at step 508 and may need to be reinserted into the response from the LLM prior to being presented to the user. To help address these issues, template tokens may be used to indicate locations within the response generated by the LLM at which one or more elements (e.g., non-textual elements, user specific information, etc.) are to be inserted. In one embodiment, the text-based response obtained from the LLM may comprise one or more template tokens associated with one or more elements to be included in the response. The one or more template tokens may then be replaced with the one or more elements within the response that is output to the user. In another aspect, the LLM may be prompted to provide executable code, e.g., to retrieve user-specific data or other contextual information when presenting a response, or to format data or use predetermined visual components or other programming objects in any suitable manner.

A template token may be used to include data such as images, charts, or graphs within the response provided to the user. The charts or graphs may be related to dynamic data obtained at step 506 (e.g., charts or graphs related to the user obtained from other services of the physiological monitoring system). Examples include a bar chart of calories consumed per day over a specific time period, a time-series plot of heart rate over a specific time period, a strain gauge, and the like.

A template token may also be used to include one or more interactive elements within the response provided to the user. Examples of interactive elements include interactive visualizations (e.g., interactive charts or graphs), widgets, and other user interface elements. The interactive elements may facilitate the user's understanding of the data presented or may be used by a user to adjust one or more settings related to the physiological monitoring system.

A template token may also be used to indicate formatting that should be applied to the response provided to the user, or a portion thereof. For example, the instruction portion of the command generated at step 508 may contain an instruction to include a template token such as "[#LIST]" or "<li>" before any text that should be bulleted, or template tokens such as "[6OLD]", "[#END BOLD]" or "<b>", "</b>" around any text that should be set in bold face. When the response is formatted prior to being presented to a user, the relevant formatting template tokens may be parsed to format the response.

A template token may also be used to incorporate documents, or links to documents, within the response provided to the user. For example, a template token may be used to indicate that a document returned by a mapping function (as described above) should be attached to the response presented to the user, or a link to the document should be provided in the response presented to the user in place of the template token.

A template token may be used to include user specific data, proprietary data, or potentially sensitive data that was not passed to the LLM in the response (e.g., data that was removed, obfuscated, or redacted from the context portion of the command). As stated above, user specific data, proprietary data, or potentially sensitive data may not be passed to the LLM to ensure that privacy and security of the system and data contained within the system is maintained. Such data may be replaced with template tokens identifying the data such that the requisite template tokens may be replaced in the output presented to the user.

One or more of the above described template tokens may be included in the output of the LLM due in part to the context data included in the contextual portion. For example, a mapping function may return, as part of the context data, a specific instruction to the LLM to include a predetermined template token within the generated response (e.g., "Include the token [#LATEST_WAKE_TIME_WIDGET] within the response you provide" or "If the response contains any lists, precede each list item with the token <li>"). Additionally, the context data returned by the mapping function may provide an indication to the LLM as to where the predetermined template token should be inserted in the response (e.g., "Include the token [#STRAIN_GAGE] at a point in your response that describes optimal strain"). In another embodiment, the instruction portion, or a part of the context portion provided by a mapping function, may include an instruction requesting the LLM to include a predetermined template token if deemed appropriate (e.g., "Include the template token [#USER_DOB] in your response if you need to refer to the user's date of birth").

Therefore, by utilizing template tokens in conjunction with the static and dynamic data available to the physiological monitoring system, the response generated by the method 500 may be dynamic, interactive, and extend beyond the capabilities offered by the LLM. As such the tokens allow for changes and customization of the format of the response to provide the end user with further information.

The response may be moderated or otherwise checked prior to being presented to the user. Like the moderation that may be performed as part of step 504, the response may be checked against a content policy prior to the response being output to the user. The content policy may define that the message should not relate to, or contain, inappropriate, offensive, malicious, and/or dangerous content. If the response is deemed to satisfy the content policy, then the response is output to the user. If the message is deemed to violate the content policy, then a warning message, error message, or alert may be presented to the user in place of a response. The response may be checked against the content policy using any suitable classification or moderation approach. In one implementation, the response is checked against the content policy using a third party moderation service such as the moderation endpoint provided by the OpenAI platform API.

In one embodiment, the response is presented to the user as part of a user interface that resembles a messaging or conversational application. In such an embodiment, the response is presented as a response from the system and may be presented within a box, bubble, or other display element that indicates that the response shown is from the physiological monitoring system. An active response architecture may be used to stream the response from the physiological monitoring system to the user. That is, a service running as part of the physiological monitoring system may poll the LLM, or an endpoint associated with the LLM, after the command has been submitted at step 508. The poll time is preferably between 0.5 s and 1.0 s. The response received from the endpoint may then be accumulated and presented as a stream of elements (e.g., text, graphics, etc.) within the user interface presented to the user. From the perspective of the user, the response is incrementally presented within the interface thereby mimicking a "typed" response by a human.

In some embodiments, after step 512 a feedback score is obtained from the user. The feedback score is indicative of a quality of the response to the message. For example, the feedback score may be a binary value indicating whether the response to the message answered the user's query or not. Alternatively, the feedback score may be an integer value that assigns a quality score to the response (e.g., using a suitable Likert scale). In a further alternative, the feedback score may be a real valued number indicating the degree of confidence that the user has in the response provided.

The message, the one or more topics, the context data, the response, and/or the feedback score may be stored as a response instance within a response database. As such, the response database may be searched to identify previous responses related to specific messages, topics, etc. that have certain feedback scores. For example, the response database may be searched to identify response instances that related to the topic "strain", and that have a positive feedback score (i.e., the user has indicated that the response suitably answered their query). As a further example, the response database may be searched to identify questions that are similar to a user's query (e.g., using a vector-based search) and that have a negative feedback score.

The response instances stored within the response database may be used to generate few-shot prompts. As stated above, few-shot prompts may be used as part of the command provided to the LLM to help train, or teach, the LLM how to use, structure, and/or format the provided contextual data. As such, the comment generated at step 508 may comprise a few shot prompt comprising one or more response instances obtained from the response database. Each of the one or more response instances have a similar message to the message obtained from the user at step 502. Additionally, or alternatively, each of the one or more response instances have matching topics to the one or more topics (determined at step 504).

Here, similarity between messages may be determined using a vector-based search similar to that described above in relation to obtaining static data at step 506. An embedding database may be generated from the messages contained within the response database and a vector representation (i.e., an embedding) of a query message used to determine one or more similar vectors within the embedding database (e.g., using a k-nearest neighbor approach). The message and corresponding response associated with any similar embeddings—i.e., embeddings that are greater than a threshold level of similarity—may be used as few-shot prompts, with the message forming the input portion of the few-shot prompt and the response forming the output portion of the few-shot prompt. This process may also be used to generate negative contextual examples. That is, the response database is searched to find similar messages with negatively received responses. These may be provided as well as, or in place of, the positive responses to help train the LLM how to use, structure, and format the relevant contextual data when generating a response. Advantageously, using the user's feedback in this way provides a form of continuous, active, learning whereby the feedback is used to train, or improve, the LLM at performing re-phrasing tasks (without having to re-train the LLM from scratch or using application specific training data).

Figure 6:
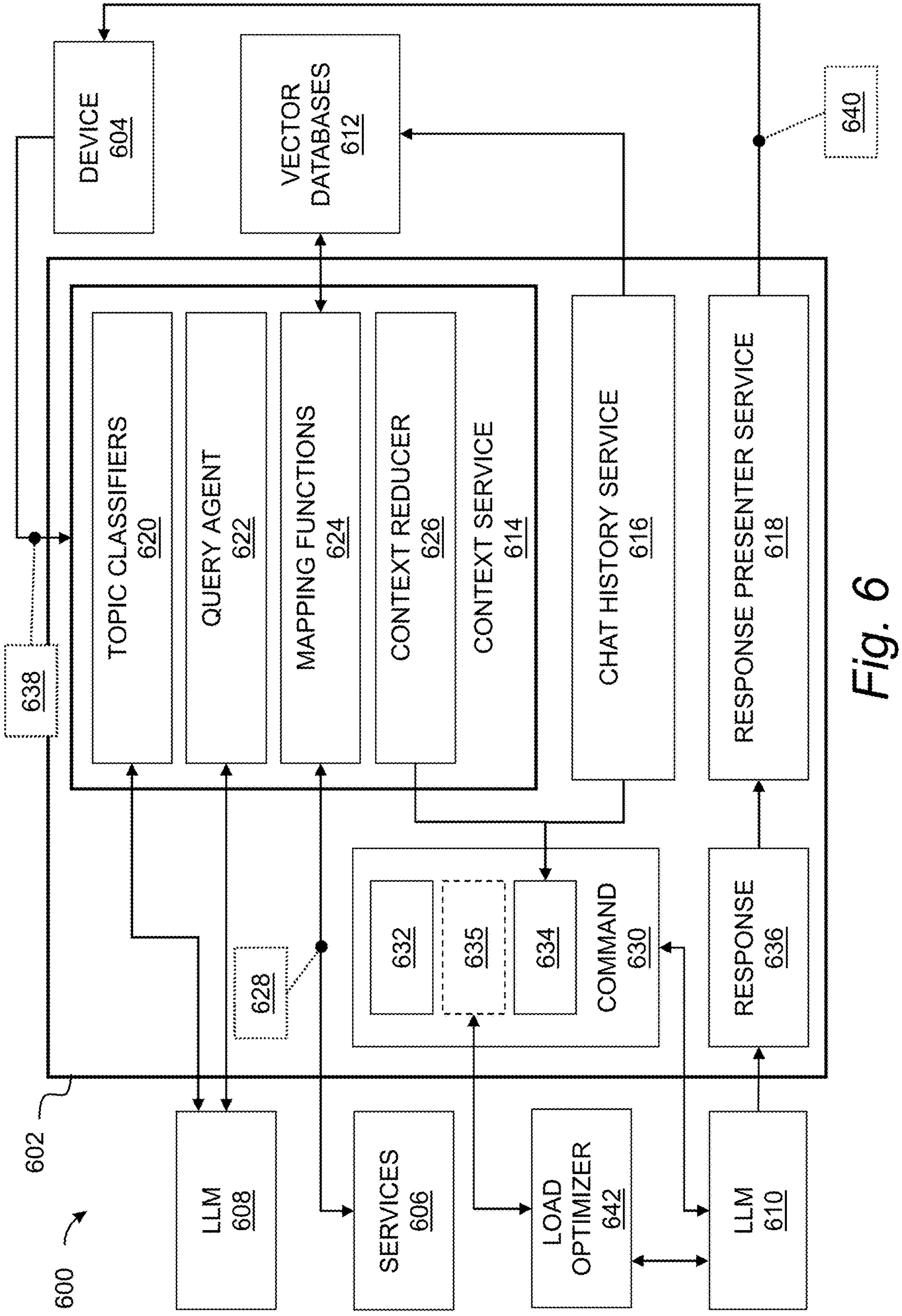
FIG. 6 shows a block diagram of a system for context-driven prompt engineering.

FIG. 6 illustrates the components of a system 600 for context-driven prompt engineering. The system 600 in an embodiment implements the method as described above with reference to FIG. 5.

The system 600 comprises an interaction module 602 communicatively coupled to a user device 604, one or more services 606, a first large language model (LLM) 608, a second LLM 610, and one or more vector databases 612. The interaction module 602 comprises a context service 614, a chat history service 616, and a response presenter service 618. The context service 614 comprises topic classifiers 620, a query agent 622, mapping functions 624, and a context reducer 626. Also shown within FIG. 6 are user data 628 and a command 630 that comprises an instruction portion 632 and a context portion 634 and optionally comprises an optimization portion 635. FIG. 6 further shows an LLM response 636, a message 638, a response 640, and a load optimizer 642.

The interaction module 602 obtains the message 638 from the user device 604 and generates the command 630 for the second LLM 610 by dynamically incorporating into the command 630 contextual data-both static and dynamic-relating a query within the message 638. The LLM response 636 is then used to provide the response 640 provided to the user.

The context service 614 receives the message 638 from the user and outputs context data that is used to generate the context portion 634 of the command 630. The topic classifiers 620 identify one or more topics related to the query within the message 638. Here, a topic may be understood as a high-level category, theme, or subject. For example, the query, "what is my optimal resting heart rate?" may relate to topics such as "heart rate", "user", and "optimal heart rate". The topic classifiers 620 may utilize a hierarchy of topic classifier and/or the first LLM 608 to identify topics within the message 638 (as described in more detail above in relation to step 504). The first LLM 608 is any suitable proprietary or third party large language model. In one embodiment, the first LLM 608 is a simpler LLM than the second LLM 610 because the first LLM 608 is only tasked with identifying topics and not tasked with the more complex rephrasing task. This enables the topic classifiers 620 to identify the topics related to the message 638 more efficiently, by reducing the computational requirement needed, as it is a simpler model. In one embodiment, if one or more of the topics identified by the topic classifiers 620 are identified as complex, or ambiguous, topics, then the query agent 622 is used to generate a structured query from the message 638. As described in more detail below in relation to FIG. 9, the structured query provides a mechanism for resolving complex or ambiguous queries within the message 638. The mapping functions 624 comprise a set of functions configured to map from a topic to a set of context data related to the topic. Each topic identified by the topic classifiers 620 is associated with at least one of the one or more mapping functions 624. A mapping function may obtain static data or dynamic data related to a topic. Static data generally corresponds to context data that remains fixed unless manually edited, whereas dynamic data refers to context data that is user specific and dynamically changes. Examples of static data include documents or portions obtained from knowledge base articles, blog articles, online encyclopedias, user manuals, and the like. Such static data may be obtained from the one or more vector databases 612 as described above in relation to step 506. Examples of dynamic data include user data 628 such as a user's heart rate, strain, sleep duration, respiratory rate, personal goals, recent exercise activity, journalling data, and the like. Such user data 628 may be obtained from one or more services 606 of the physiological monitoring system. Other examples of dynamic data include local environmental data, availability of local facilities, local event listings, matching data, and/or data about likely interests based on user profile information. The context reducer 626 may aggregate the static and/or dynamic context data obtained by the mapping functions 624 to form the context portion 634 of the command. Aggregating the context data may include concatenating the context data or converting the context data to a structured form. Additionally, or alternatively, aggregating the context data may include identifying static and/or dynamic context data that has an associated score, probability, or likelihood above a predetermined threshold (as described in more detail above in relation to step 506). Additionally, or alternatively, the context data may be filtered for relevance as part of the aggregation, or after the context data has been aggregated. The chat history service 616 may also provide as part of the context portion 634 one or more example conversations obtained from the one or more vector databases 612 based on a similarity between the message 638 and the historical messages linked to the one or more vector databases 612.

The command 630 provided to the second LLM 610 comprises the instruction portion 632 and the context portion 634 (generated by the context service 614 and, optionally, the chat history service 616). The instruction portion 632 comprises a predetermined instruction or prompt that provides the relevant instructions for the second LLM 610 to perform the requested rephrasing task. The predetermined instruction or prompt may include templates selected based on relevance and with template variables completed based on the contextual data gathered. The context portion 634 contains the contextual data or information upon which the rephrasing task is to be performed. In one embodiment, the command 630 comprises the optimization portion 635 that comprises instructions for the second LLM 610 to limit a length of the text-based response generated by the second LLM 610 according to a computational load on the second LLM 610. As will be described in more detail below in relation to FIG. 11, the computational load may be an empirical measure of the current load on the second LLM 610 or a prediction of the expected load on the second LLM 610. Advantageously, limiting the length of the output generated by the second LLM 610 based on the load on the second LLM 610 helps to manage system resources dynamically and effectively as there may be varying numbers of requests being handled by the second LLM 610 at any given time. The second LLM 610 may be any suitable proprietary or third party large language model that can provide a natural language representation of the context portion 634.

The LLM response 636 comprises the text-based natural language response to the query, or queries, contained in the message 638. The response presenter service 618 may be used to incorporate additional information, or elements, within the LLM response 636 prior to the response 640 (which is generated from the LLM response 636) being output to the user. As described in more detail above in relation to step 512, the response presenter service 618 may replace template tokens within the LLM response 636 with elements (e.g., graphics, charts, etc.) to generate the response 640. Template tokens may be used to identify portions of the LLM response 636 that should be replaced by an image or graphic, a chart, a bullet point, a hyperlink, data related to the user, proprietary data, a document, an interactive element, and/or formatted text. As such, the response 640 provided to the user (via the user device 604) comprises a rich-text response to the query, or queries, contained within the message 638.

FIGS. 7 and 8 illustrate an example user interaction and accompanying sequence diagram according to embodiments of the present disclosure.

Figure 7A:
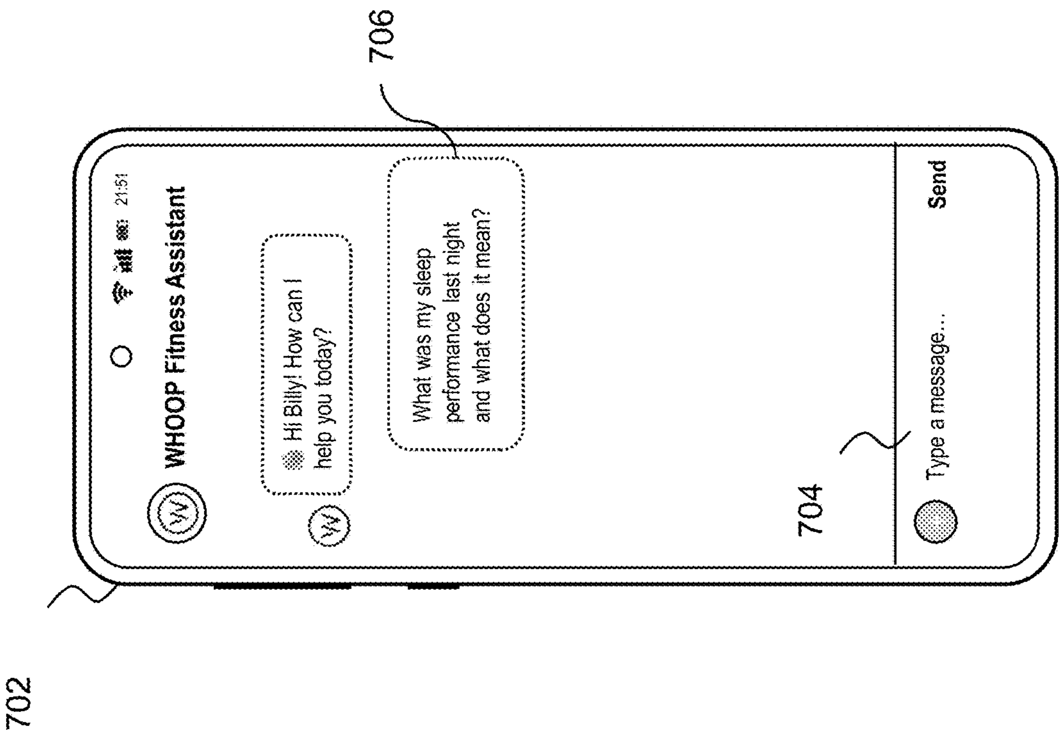
FIG. 7A shows a user interface of a physiological monitoring system.

FIG. 7A shows a user device 702 upon which a user interface of a physiological monitoring system is displayed. The user device 702 and the user interface may correspond to the user device 220 and the user interface 222 described above in relation to FIG. 2. The user interface presents a conversation between a user and the interaction service of the present disclosure. The user interface takes the form of a messaging application whereby the user may enter messages within a message box 704 that subsequently appear as messages within the messaging application.

Figure 7B:
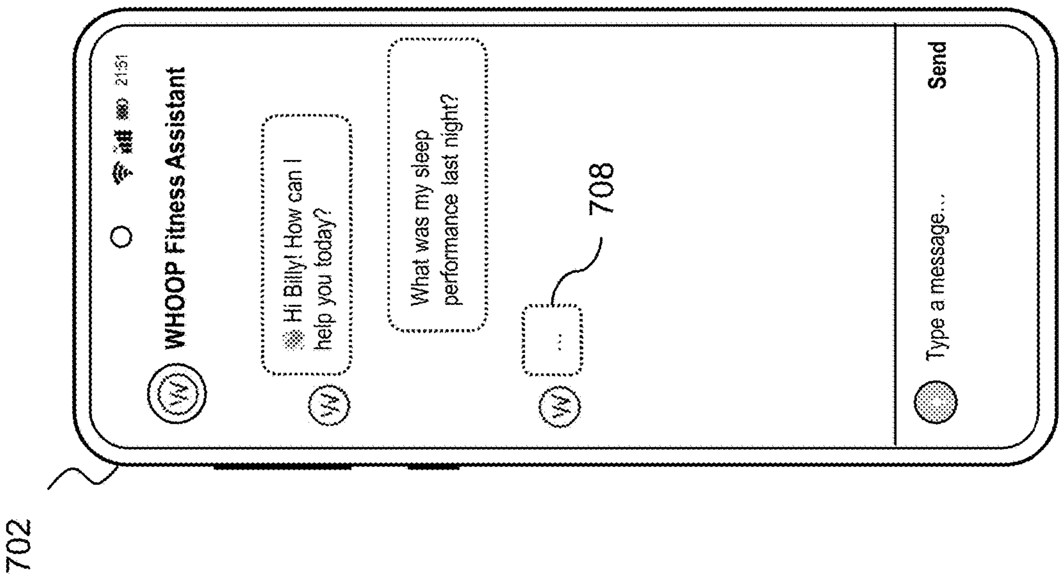
FIG. 7B shows a user interface of a physiological monitoring system.

FIG. 7A shows a message 706 provided by a user of the user device 702. The message 706, "What was my sleep performance last night and what does it mean?", includes one or more queries associated with the physiological monitoring system. As described in more detail above, the message 706 is provided to an interaction module (e.g., the interaction module 602 shown in FIG. 6) to generate a contextual response. As shown in FIG. 7B, while the response is being generated, the user interface of the user device 702 may display an initial response 708 that indicates that the message 706 has been received and is being processed.

Figure 7C:
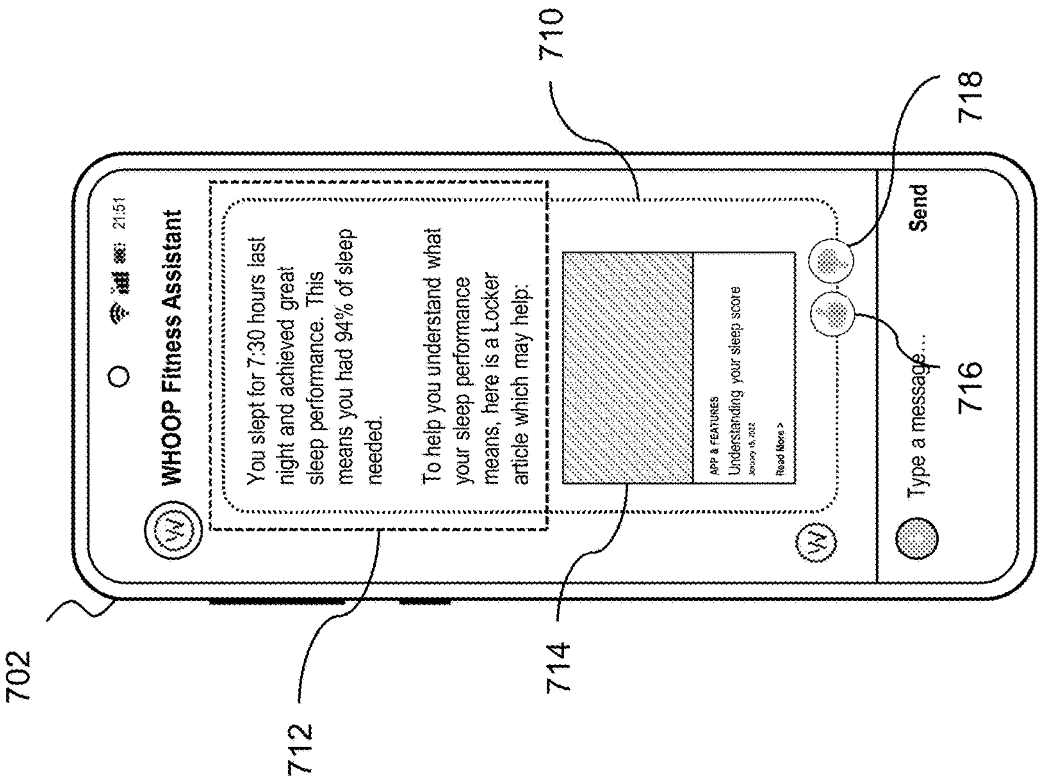
FIG. 7C shows a user interface of a physiological monitoring system.

FIG. 7C shows a contextual response 710 received from the interaction module in response to the one or more queries contained within the message 706. The contextual response 710 contains a text portion 712 and an interactive portion 714. The text portion 712 is indicated by the text contained within the dashed square of FIG. 7C. A first feedback selector 716 and a second feedback selector 718 are also displayed in conjunction with the contextual response 710.

The text portion 712 of the contextual response corresponds to the natural language rephrasing of the context data obtained by the interaction module in relation to topics identified as being related to the one or more queries within the message 706. The interactive portion 714 corresponds to an interactive element—i.e., a graphic and accompanying hyperlink to a knowledge base article—that has been inserted into the contextual response 710 prior to the contextual response 710 being sent to the user device 702. The first feedback selector 716 and the second feedback selector 718 are user selectable elements that allow the user to provide positive feedback (i.e., by selecting the first feedback selector 716) or negative feedback (i.e., by selecting the second feedback selector 718) in relation to the quality of the contextual response 710 (as described in more detail above in relation to FIG. 5).

Figure 8A:
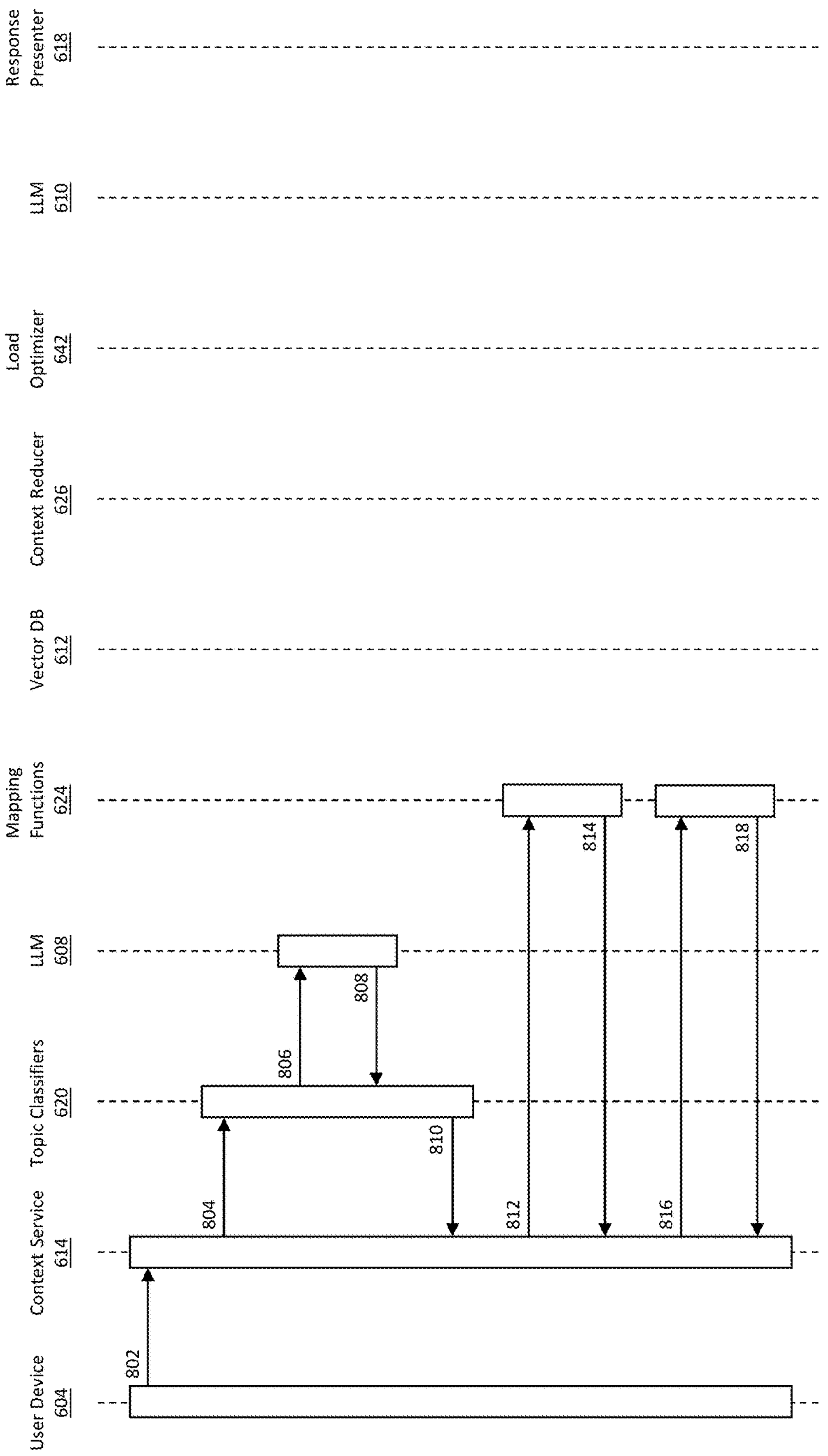
FIG. 8A shows a sequence diagram in relation to generation of at least a portion of elements of the user interfaces shown in FIGS. 7A-7C.
Figure 8B:
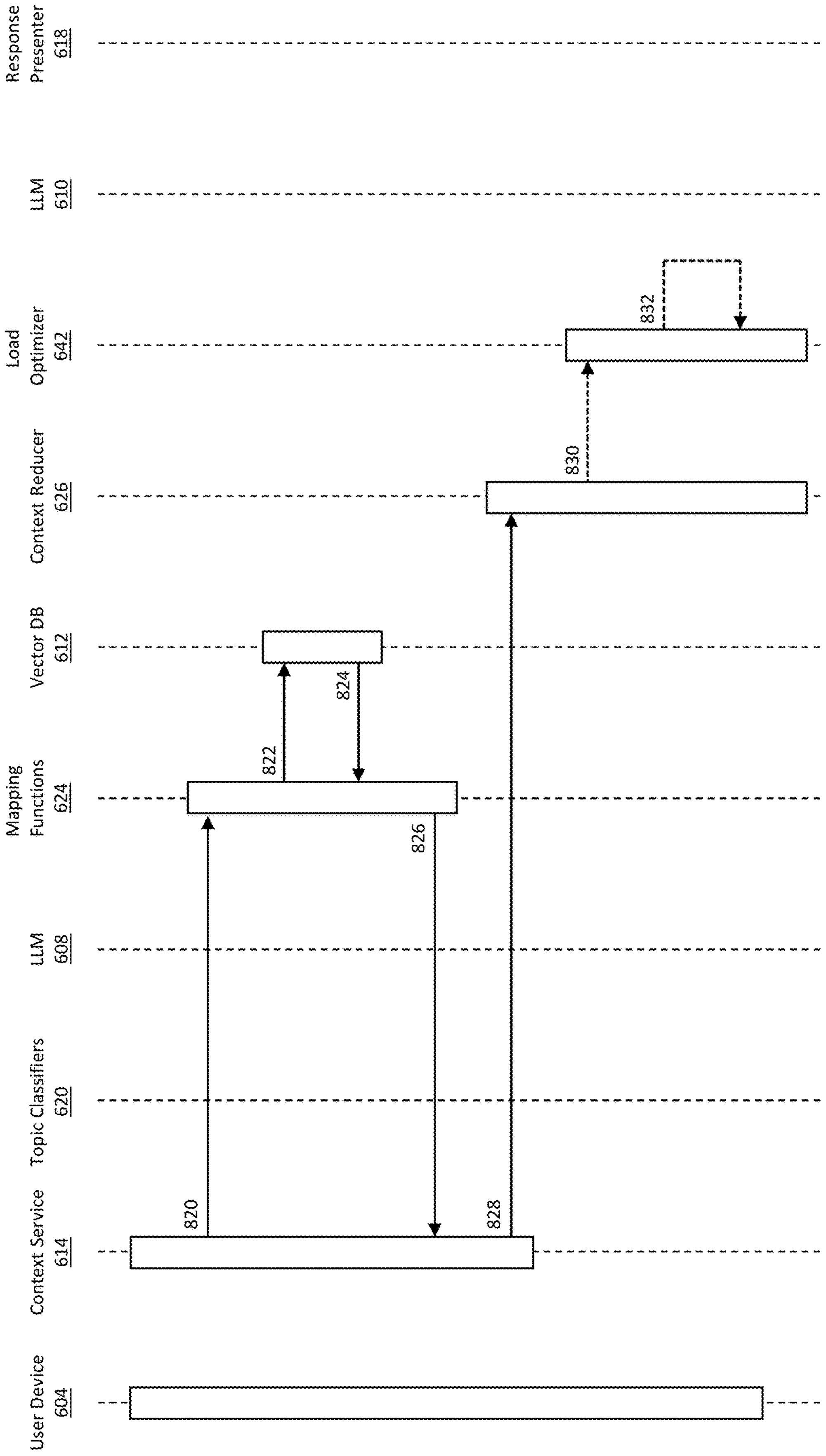
FIG. 8B shows a sequence diagram in relation to generation of at least a portion of elements of the user interfaces shown in FIGS. 7A-7C.
Figure 8C:
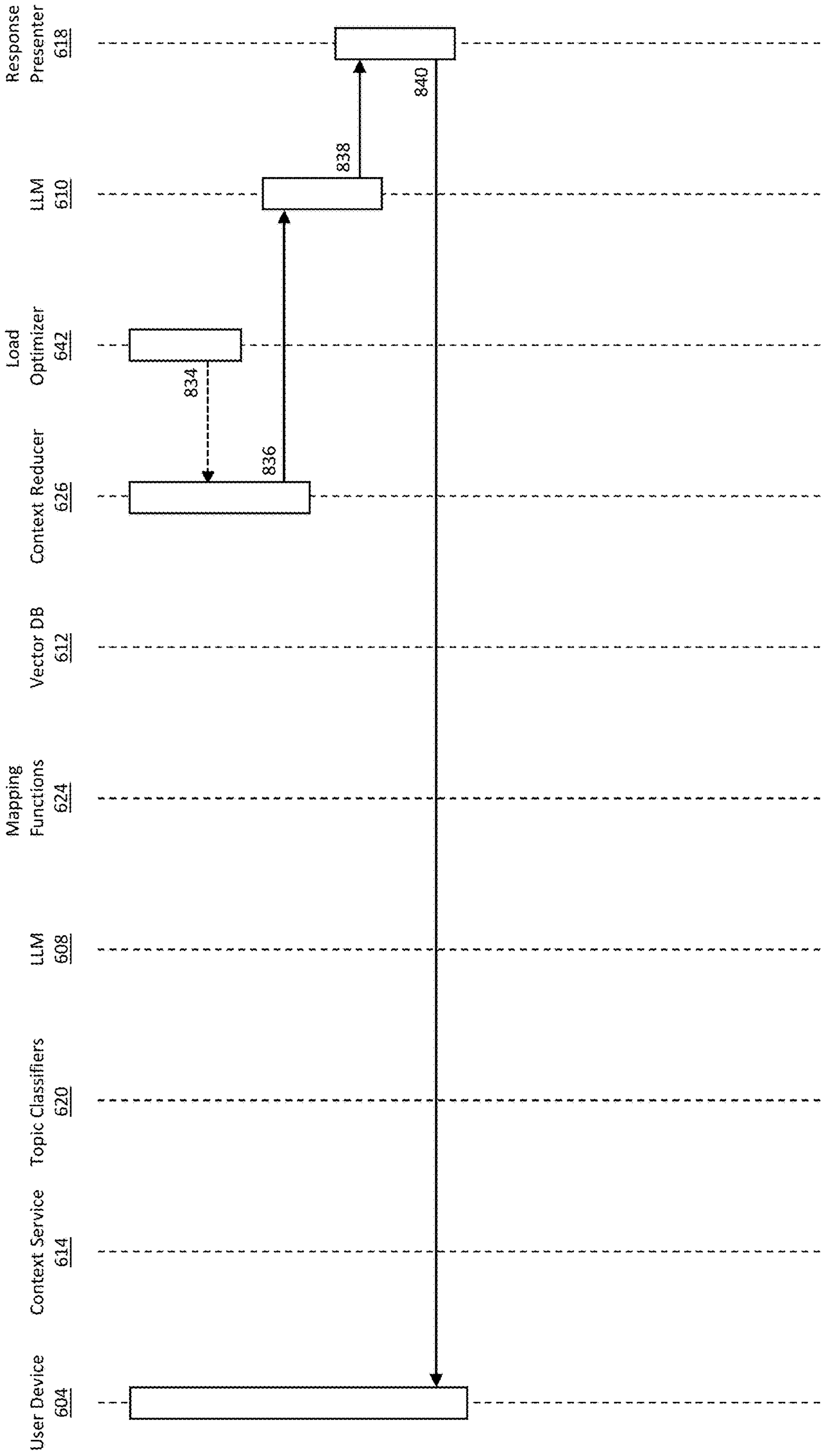
FIG. 8C shows a sequence diagram in relation to generation of at least a portion of elements of the user interfaces shown in FIGS. 7A-7C.

FIGS. 8A-8C show a sequence diagram corresponding to the steps taken by the system 600 of FIG. 6 to generate the contextual response 710 shown in FIG. 7C from the message 706 shown in FIG. 7A. As such, references will be made to FIG. 6 and FIGS. 7A-7C throughout the following description.

At step 802 (shown in FIG. 8A), the message 706 is obtained from the user device 604 and passed to the context service 614. At step 804, the context service 614 requests the topic classifiers 620 to identify one or more topics related to the query, or queries, contained within the message 706. In the example shown in FIG. 8A, the topic classifiers 620 use the first LLM 608 to identify one or more topics related to the query, or queries, within the message 706. Thus, at step 806 the topic classifiers 620 send the message 706, along with a predetermined instruction and a predetermined list of topics, to the first LLM 608. The predetermined instruction comprises a prompt instructing the first LLM 608 to determine which of the predetermined list of topics the message 706 relates to. In one embodiment, a fuzzy matching approach is used. For example, query topics are plotted against the predetermined topics in a space and subsequently matched thereby allowing a matching to be performed even when a different term is used other than one of the predetermined topics.

At step 808 the first LLM 608 returns the one or more topics associated with the query, or queries, of the message 706 to the topic classifiers 620. At step 810, the one or more topics are returned from the topic classifiers 620 to the context service 614. In the present example, the identified within the message 706 are "last_night", "sleep_performance", and "explanation".

The context service 614 then maps the topics identified within the message 706 to context data using the mapping functions 624. For example, at step 812, a first mapping function related to the topic "last_night" may be called. The first mapping function may then obtain static data providing last night's date in a predetermined format (e.g., "MM-DD-YYYY") and returns this static data to the context service 614 at step 814. At step 816, the context service 614 may call a second mapping function related to the topic "sleep_performance". The second mapping function takes an input parameter indicating the date range for which the sleep performance data should be obtained. The input parameter used is the data obtained at step 814 from the first mapping function. The second mapping function obtains the user data 628 related to last night's sleep performance from the one or more services 606. At step 818, the context data related to sleep performance is returned from the second mapping function. In this example, the context data returned from the second mapping function comprises the structured data: {"data": {"sleep score": 0.94; "sleep duration": 7.5; "sleep performance": "great"}; "examples": [{"data": {"sleep score": 0.98; "sleep duration": 8}; "responses": ["You slept for 8 hours last night and achieved great sleep performance.", "This means that you had 100% of sleep needed."]]}.

Referring now to FIG. 8B, at step 820 a third mapping function may be called by the context service 614. The third mapping function relates to the topic "explanation". The third mapping function takes as an input parameter a topic for which an explanation is sought. In this example, the third mapping function is provided with the topic "sleep_performance" as an input parameter. The third mapping function obtains static data related to the topic provided as input using a vector-based approach as described above in relation to FIG. 5. At step 822 a vector representation of the topic "sleep_performance" is provided to the one or more vector databases 612 and a document related to explaining sleep performance is returned to the third mapping function at step 824. In this example, the document is a public knowledge base article accessible via a provided URL. At step 826, static context data comprising the URL obtained from the one or more vector databases 612 is returned to the context service 614. In this example, the static context data returned from the third mapping function comprises context data corresponding to the prompt, "WHOOP bot, insert the following text at the end of the response: 'To help you understand what your sleep performance means, here is a Locker article that may help: [#LINK: http://whoop.com/kb/1234]". The context data thus comprises a template token that will be replaced with an appropriate element within the response sent to the user. The skilled person will appreciate that the appropriate element need not be a hyperlink, but instead may be any other suitable identifier, tag, reference, or the like, or may be directly related to the context data to help provide surrounding context for a user's metrics (e.g., "here is a paragraph about how strain impacts sleep need . . . ").

At step 828, the context data obtained by the context service 614 is provided to the context reducer 626. In the present example, the context reducer 626 concatenates the context data received from the first mapping function, the second mapping function, and the third mapping function into a contextual portion of a command to be provided to the LLM 610. The command may include an instruction portion and the contextual portion. The instruction portion comprises an instruction informing the LLM 610 that it is required to perform a rephrasing task based on the contextual portion (e.g., "WHOOP is a 24/7 performance coach that can answer any question the user has that relates to their fitness goals. WHOOP always refers to itself as 'WHOOP' and never uses personal pronouns such as I or me. WHOOP has access to the user's data including information about their Sleep, Strain, and Recovery. This data is collected through a physical wearable device called the WHOOP Sensor. WHOOP always responds in 3-4 sentences. WHOOP gives actionable advice to the user to help them meet their health and fitness goals. The advice is always tied back to the user's WHOOP data. Answer the user's question using only their data shown below. If there is not enough information, let them know you don't have that data. Today is {{today}}").

Optionally the system performs steps 830 and 832. At step 830, the load optimizer 642 determines a computational load on the LLM 610 so as to include the optimization portion 635 within the command 630 provided to the LLM 610. In the example shown in FIG. 8B, the load optimizer 642 is shown as being called or invoked by the context reducer 626; however, the skilled person will appreciate that the generation of the optimization portion 635 within the command 630 may be coordinated by one or more other components of the system 600. At step 832, the computational load on the LLM 610 is obtained (e.g., from a previously recorded load value) and the optimization portion 635 is generated based on the computational load. The optimization portion 635 comprises instructions for the LLM 610 to limit a length of the generated response according to the computational load on the LLM 610. It will be appreciated that the computational load for the LLM 610 may be inferred based on a measured responsiveness of the LLM 610, determined by a direct query to the LLM 610 (where the LLM 610 is configured to provide relevant performance data), or estimated based on a local queue of LLM prompts or request that will be sent to the LLM 610. More generally, any technique for measuring or estimating the computational load on the LLM 610 may be used to obtain the load on the LLM 610 as contemplated herein. In this context, the computational load may also or instead include the network load, such as any network latency, bandwidth, or other network characteristics or performance metrics that might be used to measure or estimate the responsiveness of the LLM 610.

Referring now to FIG. 8C, at step 834 the optimization portion 635 may be provided for use within the command 630. At step 836, the command 630 may be provided to the LLM 610 that then provides a natural language rephrasing of the context portion of the command (i.e., the context data). At step 838, the response obtained from the LLM 610 is provided to the response presenter service 618. The response is generated by the LLM 610 in accordance with the computational load on the LLM 610 (i.e., the length of the generated response is limited according to the computational load). The response presenter service 618 may format the LLM response so as to appear consistent with other text within the physiological monitoring system. In the present example, the response presenter service 618 replaces the template token "[#LINK: http://whoop.com/kb/1234]" with an interactive portion 714 that comprises a selectable image that links to a knowledge base article explaining sleep performance.

At step 840, the response is returned to the user device 604 (i.e., the user device 702) and presented on the user device 604 as the contextual response 710 shown in FIG. 7C. As stated above, the contextual response 710 may be progressively displayed on the user device 702 by using an active response architecture that periodically polls the interaction module 602 to obtain the portions of the response 640 that have been generated and are currently buffered.

It will be understood that, while the response may be presented on the user device 604 that generated the initial user message or request, the response may also or instead be presented on, and/or used by any other computing device or other component or user device in the system. In one aspect, this may be another device associated with the user, e.g., where a user message is initiated from a desktop computer, and the response is rendered on a smart phone or tablet. As another example, where the response includes executable code implementing a processable response to the user request, the response may be transmitted, e.g., to an IoT device, smart home device, programmable exercise equipment, or other component(s) that might process the response to provide a functional implementation of the response to the user.

Figure 9:
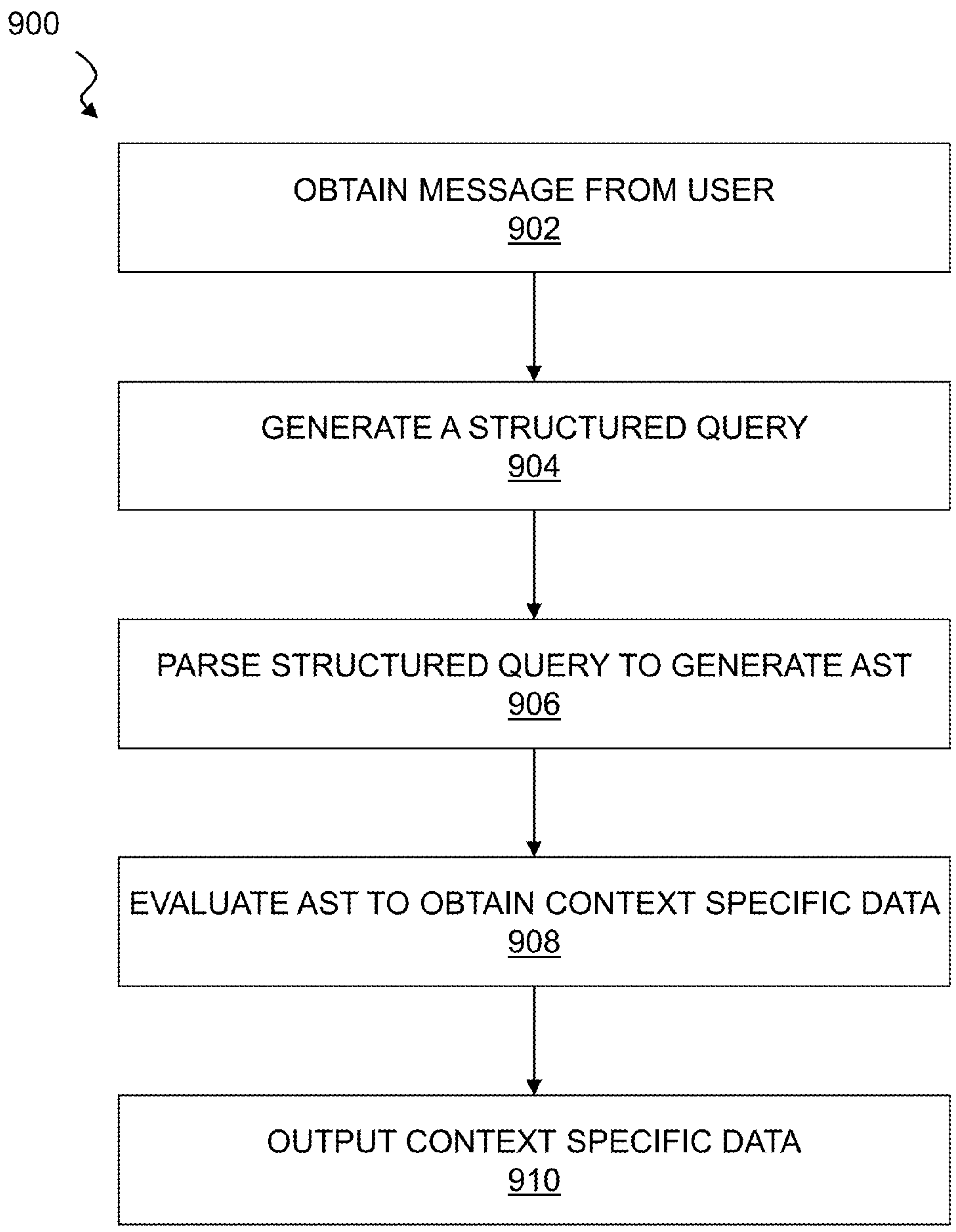
FIG. 9 is a flow chart illustrating a method for resolution of an ambiguous query within a user message.

FIG. 9 is a flow chart illustrating a method 900 for resolution of an ambiguous query within a user message. An ambiguous query can result in the system being unable to answer the query, or incorrectly answering the query. The method 900 may be used in cooperation with any of the devices, systems, and methods described herein, such as by a user device (e.g., a mobile device) that is communicatively coupled to a wearable, continuous physiological monitoring device. For example, the one or more user devices 220 that are communicatively coupled to the physiological monitor 206 in FIG. 2. In general, the method 900 obtains context specific data from ambiguous queries within a user message. For example, a user query may contain a request for data in relation to a relative date or time period—e.g., "strain data after my last weight lifting session"—that may not be easily resolved using a direct mapping from topics to mapping functions. As such, the method 900 provides an approach for effectively obtaining context specific data in response to a complex or ambiguous query from a user.

In one embodiment, the method 900 is used as part of the method 500 shown in FIG. 5. More particularly, the method 900 is used as part of the process of mapping topics to context specific data. In such an embodiment, step 902 corresponds to step 502, step 904 is performed after or instead of step 504 and prior to step 506, and steps 906 and 908 are performed instead of or as a part of step 506. Thus, in one aspect, the method 900 may include mapping directly from the user's message to the set of context specific data.

As shown in step 902, the method 900 may include obtaining a message from a user (e.g., a user of a physiological monitoring system). The message includes a query that may be associated with the physiological monitoring system. The query may be an ambiguous query.

Within the context of the present disclosure, a query that is not ambiguous is a query that can be resolved using data explicitly stated within the query. For example, the query "what was my strain yesterday?" may be resolved directly from the query because the query explicitly relates to the metric "strain" and the time point "yesterday". Thus, the query may be resolved using a mapping function for the topic "strain" and a mapping function for the topic "yesterday". As such, unambiguous queries do not require any further aggregation or processing to be resolved (i.e., to be able to map topics within the query to relevant mapping functions). In contrast, ambiguous queries cannot be resolved directly from the literal wording of the query due to a lack of explicit references to topics within the query. For example, the query "what was my recovery after I played soccer?" requires resolution of ambiguous, and complex, references to a prior time period corresponding to a time subsequent to the user having played soccer.

As shown in step 904, the method 900 may include generating a structured query by providing one or more prompts to a large language model (LLM). The one or more prompts comprise a predetermined instruction, the message from the user received at step 902, and a schema for the query language. In one embodiment, the predetermined instruction, the message received from the user, and the schema for the query language are provided within a single prompt.

In general, the LLM is used to convert the message from the user, which is typically in a free text form, into a structured query (i.e., a query within a query language) that may be evaluated to obtain the relevant context data. The structured query may be alternatively referred to as a code block or code portion. The predetermined instruction comprises a command or instruction to cause the LLM to generate a structured query, or code block, which adheres to the schema for the query language and utilizes the functions defined in the schema to obtain the relevant context data to answer the query in the user's message. In one embodiment, the predetermined instruction comprises an instruction for the LLM to provide chain of thought reasoning—i.e., the LLM is instructed to output the reasoning behind arriving at an answer before providing the answer. Advantageously, this helps to ensure that the output generated by the LLM is accurate. The LLM used to generate the structured query may be any suitably trained large language model. The LLM may be a proprietary LLM that is internally deployed within the physiological monitoring system (e.g., as part of the other resources 250 shown in the physiological monitoring system 200 of FIG. 2). Alternatively, the LLM may be offered as a service by a third party. In such implementations, the LLM is accessible via one or more application programming interface (API) endpoints. The structured query may be generated by providing the prompt to the API endpoint and obtaining a response containing the structured query. Example third party services include GPT-3 provided by OpenAI, Bloom by BigScience, and Google PaLM.

The schema for the query language may include a formal definition of the query language. For example, the schema may include a language schema and an object schema. In one aspect, the language schema defines at least a syntax, functions, and operators for a programming language used to express the code block. The object schema may specify the programming objects available for use in the code block (e.g., the list of all available mapping functions used to obtain context specific data). As such, the schema provides a language specification for the query language that defines the syntax, grammar, and possible operations of the query language. Providing the full schema for the query language to the LLM helps to ensure that the LLM does not make any assumptions as to what is, and is not, available in the query language. In one embodiment, the query language is a language referred to as AIQL as described below.

AIQL is a query language that has syntax similar to programming languages such as JavaScript or Python thereby allowing the LLM to leverage its existing knowledge to generate an AIQL query efficiently and reliably. AIQL utilizes function based expressions that make it simpler and more efficient to parse. As such, every top level expression within AIQL is a function call of the form fn1(arg1, arg2, fn2(arg3), . . . ). For example, the AIQL expression let (x, 0) sets the value of variable x to 0. To make AIQL easier to generate and parse, it supports dynamic typing such that only the primitive types of Boolean, number, string, function, objection, and list are used. Everything else is a combination of these primitive types or is an implied type such as date (which is a string). As such, the syntax does not distinguish between doubles, integers, floats, etc. Rather, all numerical expressions are to be evaluated generically as a "number" (e.g., both 42 and 0.2 are evaluated as a number). The syntax for string literals allows string expressions to be wrapped with either single or double quotes thereby avoiding the need to enforce a single quotation style on the LLM (e.g., "hello world" or 'hello world'). Symbol expressions are symbolic references to other values or functions that are accessible within the scope of the current execution. The syntax for symbol expressions uses a snake case format (e.g., my_var, find_all, etc.). Lists are defined within the syntax of AIQL using the common convention of square brackets surrounding a list of expressions separated by commas (e.g., [1, 2, 3] or [fun ( ) 'Hello World']). The syntax for function expressions within AIQL is a function name with parentheses directly after. Within the parentheses there may be zero or many arguments (which may themselves be expressions) separated by commas (e.g., fn1(arg1, arg2)). Like the syntax for symbol expressions, the function name syntax follows a snake case format. Expressions within the function arguments are evaluated in left to right order to generate a set of arguments that are provided to the function. The syntax for AIQL also supports macro expressions that are syntactically the same as function expressions but differ in the way in which they are evaluated. Each macro expression provides functionality that is not available with basic function evaluation. A lambda macro expression produces an unnamed function that evaluates an expression in the second argument with the argument (s) as symbols in the first argument. For example, the lambda macro expression lambda (x, add (x, 1)) evaluates the function add (x, 1) with the value provided for the first argument provided to the lambda macro expression, x. A conditional macro expression evaluates one of two expressions provided as the second and third argument depending on the value provided as the first argument (e.g., if (should_double, multiply (x, 1), multiply (x, 2))). Conditionals are represented as macro expressions so as not to evaluate the expression associated with the else statement unless the specific condition for evaluation is met (in contrast, function expressions would evaluate all arguments/expressions). White space has no semantic meaning within the AIQL syntax so as to allow the LLM to indent, or not indent, as is convenient for it to generate a correct output. The AIQL schema further comprises a list of all mapping functions that are available for obtaining static or dynamic data.

As shown in step 906, the method 900 may include parsing the structured query to generate an abstract syntax tree (AST) representation of the structured query. That is, once the output from the LLM is obtained, it is parsed to generate an AST. In further embodiments other known hierarchical formats are used.

Figure 10:
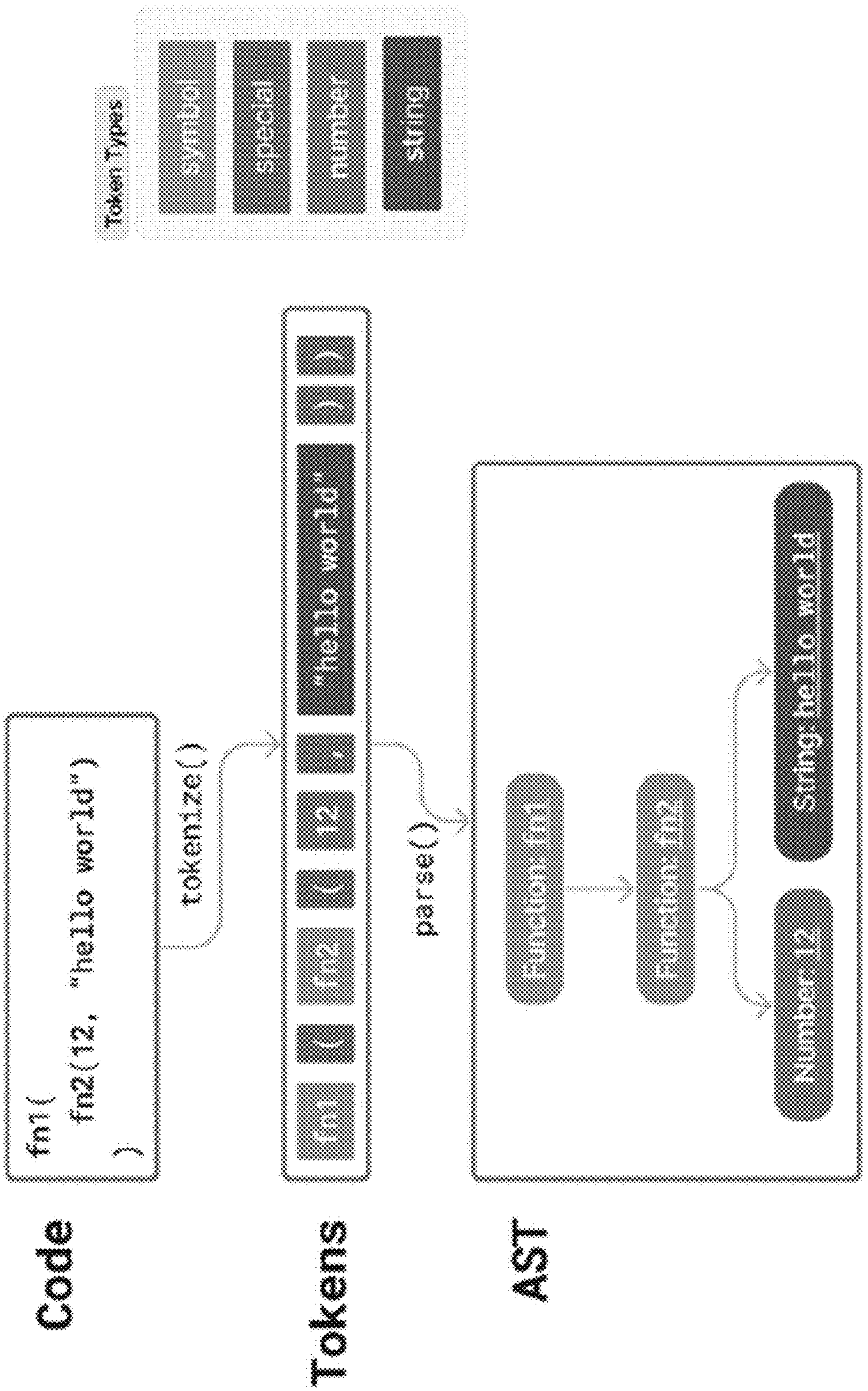
FIG. 10 illustrates tokenization and parsing of a structured query.

As is known, an abstract syntax tree (AST) is a hierarchical representation of the structure of the structured query. The AST provides an efficient and concise representation of the structured query by capturing the relationships between the elements within the structured query such as expressions, statements, and the like. Advantageously, representing the structured query using an AST makes evaluation of the query easier and more efficient. The AST is generated from the structured query using a two-step process. First, the string containing the structured query generated by the LLM is tokenized into a list of tokens. Second, the list of tokens are recursively passed into an AST. This is illustrated in FIG. 10 where the structured query fn1(fn2 (12, "hello world")) is tokenized into the list ["fn1", "(", "fn2", "(", "12", ",", "'hello world'", ")", ")"] that is then recursively parsed to form the AST.

The string is tokenized at the first step using regular expressions (regex). More particularly, regular expressions are used to identify which token is at the front (i.e., start) of the structured query string. There are five types of regex capture: (1) white space, which is ignored; (2) symbolic names; (3) special symbols such as "(", ")", "[", and "]"; (4) numbers, which may be decimals, negative numbers, etc.; and (5) strings, which, when tokenized, include the quotation marks so that they can be parsed. The regex capture is then converted into a token and added to the list of tokens. The captured string is removed from the structured query string thereby promoting a new token to the front of the structured query string. The process is repeated until the entire structured query string has been tokenized. The list of tokens are parsed at the second step to generate an abstract syntax tree (AST). The AST is generated by recursively parsing the list of tokens using an approach such as recursive descent, top-down parsing, Pratt parsing, or the like.

As shown in step 908, the method 900 may include evaluating the AST representation of the structured query to obtain context specific data related to one or more topic associated with the ambiguous query. The context specific data is obtained using one or more mapping functions identified from the evaluation of the AST representation of the structured query.

The AST representation of the structured query is evaluated by recursively traversing the AST. Nodes within the AST that are related to functions directly map to the mapping functions used to obtain static or dynamic data. As such, the recursive traversal and evaluation of the AST results in at least one of the one or more mapping functions being called to obtain context specific data related to the ambiguous query (as described in more detail above in relation to FIGS. 5 and 6).

In an alternative embodiment, instead of performing steps 906 and 908, the structured query is processed by executing or interpreting the code within the structured query, e.g., using a compiler and executor, interpreter, programming environment, shell, or the like.

As shown in step 910, the method 900 may include outputting the context specific data as a resolution to the ambiguous query. In one embodiment, outputting comprises outputting the context specific data to a context reducer (e.g., the context reducer 626 shown in FIG. 6). Additionally, or alternatively, outputting the context specific data comprises transmitting, sending, or displaying the context specific data.

Figure 11:
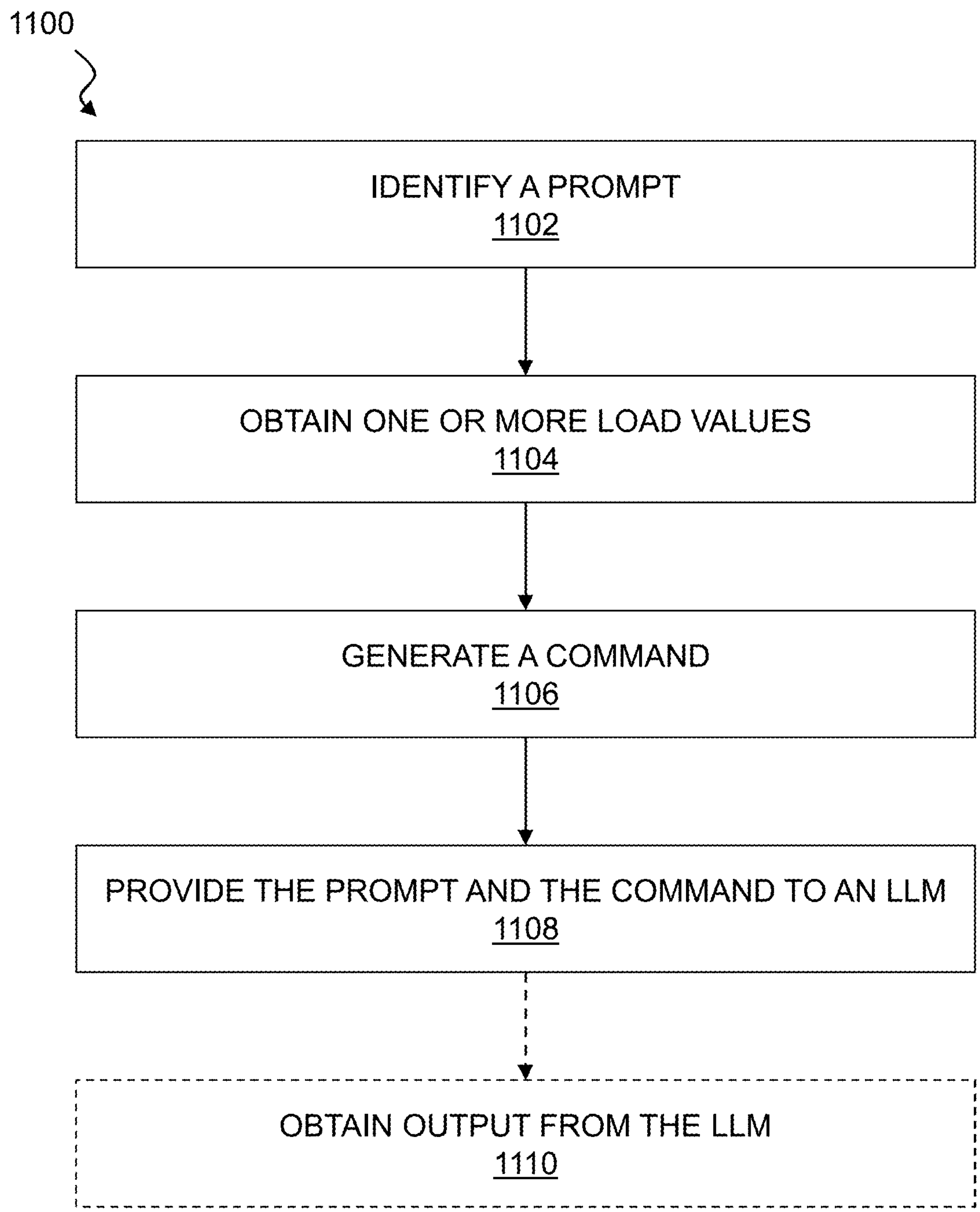
FIG. 11 is a flow chart illustrating a method for dynamically optimizing load on a large language model.

FIG. 11 is a flow chart illustrating a method 1100 for dynamically optimizing load on a large language model (LLM). The method 1100 may be used in cooperation with any of the devices, systems, and methods described herein such as by a user device (e.g., a mobile device) that is communicatively coupled to a wearable, continuous physiological monitoring device. For example, one or more user devices 220 that are communicatively coupled to the physiological monitor 206 in FIG. 2. In general, the method 1100 dynamically adapts the output generated by an LLM based on a computational load on the LLM. For example, during periods of peak operations where the LLM is experiencing high computation load, the LLM may be instructed to limit the length (i.e., number of tokens) within a generated output so as to reduce the load on the LLM. As such, the method 1100 provides a dynamic and efficient approach for managing multiple requests made on an LLM so as to optimize LLM performance across the requests thereby reducing delays in receiving a response from the LLM during periods of high load. This in turn helps an LLM serve as many concurrent requests as possible. Moreover, the method 1100 provides a method for measuring and optimizing performance of a remote or external LLM. That is, the performance of the LLM may be optimized without direct control of the LLM.

In one embodiment, the method 1100 is used as part of the method 500 shown in FIG. 5. More particularly, the method 1100 is used as part of the process of generating a command at step 508 (i.e., generating the optimization portion 635 of the command 630 as represented in FIG. 6).

In one embodiment, the optimization methodology is applied to all requests generated and submitted to the LLM. In some embodiments, as described with reference to FIG. 5, users are segmented into two or more groups such that commands for users within a first group include the optimization portion (and thus have reduced length output) while commands for users within a second group do not include the optimization and therefore the process of FIG. 11 is not applied to these users. Advantageously, this may enable different tiers of service levels, e.g., for standard versus VIP members, for different standard fee and higher fee levels, or based on user attributes such as user goals, level of engagement with the product, or need for coaching (e.g., beginner versus advanced user).

As shown in step 1102, the method 1100 may include identifying a prompt to be provided to an LLM for conducting a task related to a physiological monitoring system. In one embodiment, the prompt is related to a rephrasing task to be performed by the LLM, as described above. The prompt may thus comprise an instruction portion and a context portion, where the instruction portion comprises instructions for the LLM to perform the rephrasing task based on context specific data contained within the context portion.

As shown in step 1104, the method 1100 may include obtaining one or more load values indicative of a computational load on the LLM, and/or any network latency or bandwidth limitations affecting communications with the LLM. While the following examples focus in actual or expected computational load, more generally the load on the LLM, as expressed in one or more load values, may be based on measurements of network performance, measurements of LLM responsiveness, metrics received from the LLM (where available) indicating a current computational load, and/or load estimates based on, e.g., historical usage patterns or information about a current queue of work for the LLM. In one aspect, the one or more load values indicate the usage that is currently being made of, or is expected to be made of, the LLM. As such, the one or more load values may quantify an actual or predicted computational load on the LLM (or related network performance). Here, load is to be understood as a measure of the computational work being undertaken by an LLM at any given time, or any other suitable measure of responsiveness or performance of the LLM. A high load value may indicate that the LLM is processing a higher number of requests and may thus be delayed in generating a response. Therefore, load may be alternatively referred to as usage, computational usage, or a performance measure/characteristic.

In one aspect, the one or more load values may include a time to first token (TTFT) value. A TTFT value quantifies the delay between a prompt (instruction or command) being sent to an LLM and the first token being received in response. As is known, a token is an atomic unit of text used to represent a word, phrase, or other piece of text (e.g., a word, sub-word, punctuation mark, number, etc.). As such, a TTFT value is a measure of the latency of the LLM in processing an instruction and beginning to generate a response. A higher TTFT value indicates a greater load on the LLM than a lower TTFT value. The TTFT value may be determined from a metric obtained from the LLM. For example, the interval between issuing the instruction to the LLM and receiving the first token may be measured in milliseconds and recorded as the TTFT value. In one embodiment, the response time is periodically obtained as described above over a period of time (e.g., 10 minutes, 30 minutes, 60 minutes, 12 hours, 1 day, etc.) and an average response time recorded as the TTFT value. In one embodiment, a normalized TTFT value may be generated by subtracting a transmission (network) latency value from the TTFT value. The transmission latency value may be obtained from a ping of the LLM.

The one or more load values may include a number of active requests value. An LLM may have zero to many active requests at any given time. Here, an active request is a request sent to the LLM that has not yet been fully or finally processed (i.e., a request or prompt has been sent to the LLM, but the LLM has not yet issued the final token of the response). The number of active requests thus provides an indication of the current computational load of an LLM with a higher value indicating a greater load on the LLM.

The one or more load values may include a time to last token (TTLT) value. A TTLT value quantifies the delay between a prompt (instruction or command) being sent to an LLM and the final token (i.e., word or character) being received in response. The TTLT value may be determined from a metric obtained from the LLM. For example, the interval between issuing the instruction to the LLM and receiving the final token may be measured in milliseconds and recorded as the TTLT value. In one embodiment, the response time is periodically determined as described above over a period of time (e.g., 10 minutes, 30 minutes, 60 minutes, 12 hours, 1 day, etc.) and an average response time recorded as the TTLT value. A normalized TTLT value may be generated in the same way as described above in relation to the normalized TTFT value.

The one or more load values may include a predicted load value. As such, while the previously described load values correspond to empirical measures of a current load on an LLM, the predicted load on an LLM may also be used to adapt the output generated by the LLM. The predicted load value is associated with a predicted load on the LLM for a period of time and/or a geographic region. For example, because the LLM is being used within the context of a physiological monitoring system, it may be expected that load on the LLM will increase during specific times of the day (e.g., between 6 am and 9 am, between 5 pm and 8 pm, etc.). As such, if it is predicted that the load on the LLM will be high for the current time period within a specific geographic region (e.g., the East Coast of the United States) then the predicted load value will be higher than if it is predicted that the load on the LLM will be low for the current time period within the specific geographic region. The predicted load value may be determined from historical usage data related to user activity of the physiological monitoring system (e.g., the average number of active users during a time period within a geographic region). In further embodiments the predicted load value can be determined from historical load data of the LLM.

As shown in step 1106, the method 1100 may include generating a command comprising instructions for the LLM to generate an output according to an output length criterion. The output length criterion is based on the one or more load values. In general, the command causes the LLM to generate an output having a length that is proportional to the load on the LLM. Here, the length of an LLM's output may be measured in the total number of tokens within the output. The output length criterion thus causes the LLM to limit the number of tokens within the generated output such that the number of tokens within the output is proportional to the load on the LLM as represented by the one or more load values.

In one embodiment, the output length criterion is based on a load value satisfying a threshold. For example, an output length criterion may limit the output length to 100 tokens if the TTFT value is greater than a first time threshold say 5 s. As a further example, an output length criterion may limit the output length to 100 tokens if the predicted load, or usage, for the current time period is greater than 100 concurrent requests—that is to say that the predicted load at a given time is identified as being likely to result in a degradation in performance of the LLM. In one embodiment, the output length criterion causes the LLM to limit the number of tokens to a first maximum number of tokens if at least one of the one or more load values satisfy a first load threshold, and the output length criterion causes the LLM to limit the number of tokens to a second maximum number of tokens if at least one of the one or more load values satisfy a second load threshold. The second load threshold is greater than the first load threshold and the second number of tokens is less than the first number of tokens. For instance, a first load threshold corresponding to a TTFT value greater than 5 s may be used to limit the number of tokens to 100 tokens and a second load threshold corresponding to a TTFT value greater than 5.5 s may be used to limit the number of tokens to 75 tokens. Further thresholds may be used to further decrease the limit of the number of tokens (e.g., reduce the number of tokens from 75 to 50).

In one embodiment the token limit is set as a percentage decrease of previous responses. For example, the prompt to the LLM can include the instruction "Using 10% fewer tokens than the previous response . . . " to limit the length of the output.

As shown in step 1108, the method 1100 may include providing the prompt and the command to the LLM. In one embodiment, which may occur in addition, or separately to the output limiting described above, the prompt provided to the LLM is trimmed (e.g., shortened or simplified) based on the one or more load values. That is, if at least one of the one or more load values indicate that the load on the LLM is high (e.g., the value(s) satisfy or exceed a threshold), then the prompt may be trimmed. For example, if the number of active requests value is greater than 500 requests, then the prompt provided to the LLM may be trimmed. Trimming the prompt may comprise removing one or more items of contextual data from the prompt. For example, if the prompt comprises contextual data related to knowledge base articles or comprises template tokens for generating dynamic content (as described above), then these portions of the prompt may be removed to simplify the response generated by the LLM. By trimming the prompt the LLM has less data to analyze in order to produce a response and the computational requirement, and therefore load, on the LLM is reduced.

As shown in step 1110, the method 1100 may include obtaining the subsequent output from the LLM. That is, the output satisfying the output length criterion may be received from the LLM and provided to a user or one or other units, functions, or methods.

Figure 12:
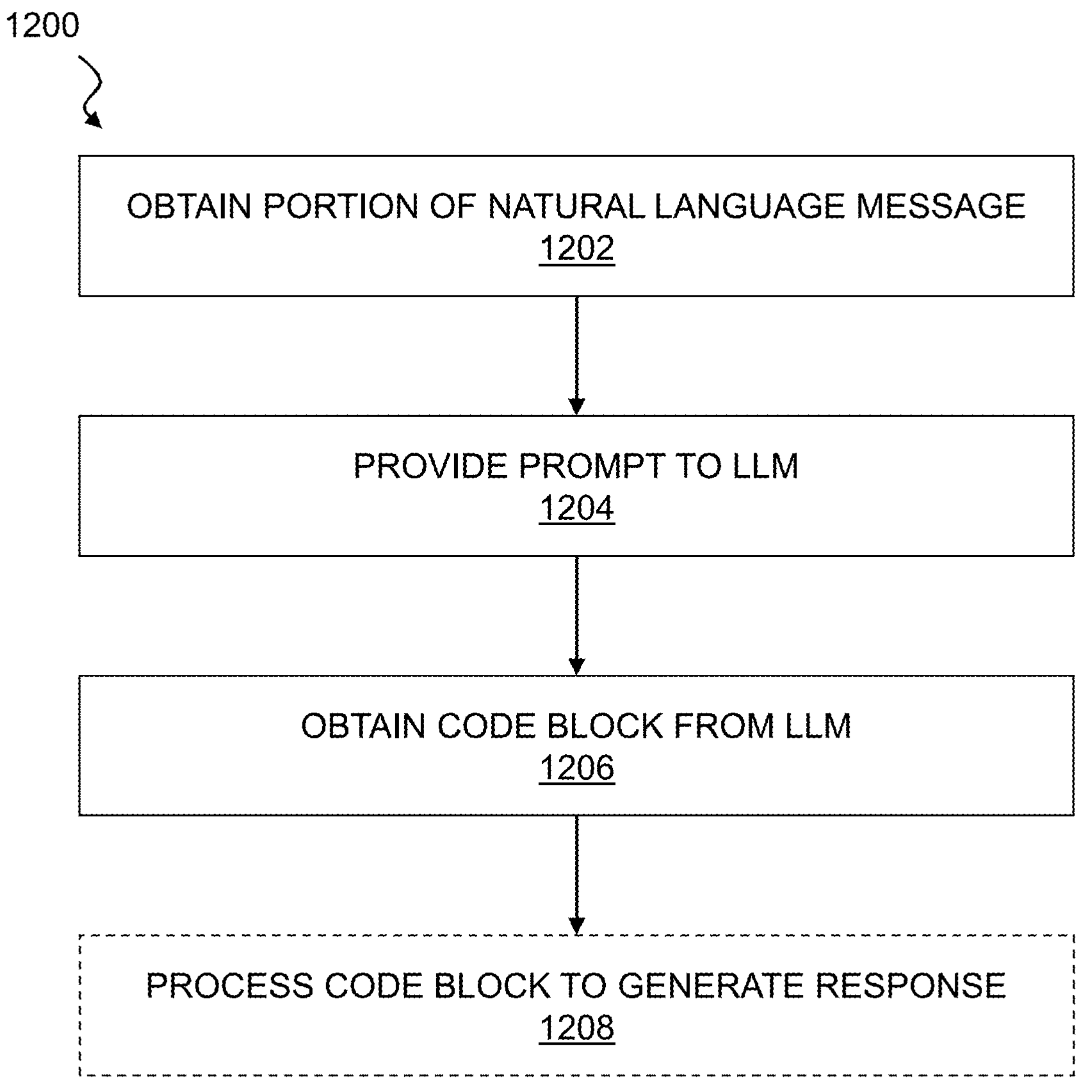
FIG. 12 is a flow chart illustrating a method for generating cross-component responses to user requests.

FIG. 12 is a flow chart illustrating a method 1200 for generating cross-component responses to user requests. The method 1200 may be used in cooperation with any of the devices, systems, and methods described herein such as by a user device (e.g., a mobile device) that is communicatively coupled to a wearable, continuous physiological monitoring device, for example, one or more user devices 220 that are communicatively coupled to the physiological monitor 206 in FIG. 2. In general, the method 1200 obtains a request from a user of a system, such as a physiological monitoring system, and generates a program (i.e., code block) that is executable by components of the system to provide a response to the request. More particularly, a prompt is provided to a large language model (LLM) to cause the LLM to output a code block that encodes a response to the request and is processable by one or more components of the system. As such, the code block provides a unified and reusable representation of the response to the user request. Different components of the system—e.g., specific applications such as a workout or strength trainer applications, user interface components, or an interface to applications external to the system, and/or different devices—can process or execute the code block to generate a component, or context, specific representation of the response to the user request. For example, a code block (program) representation of a workout requested by the user may be processed by a workout application and summarized in natural language for display to the user. As a further example, a code block (program) representation of a user's request to adjust the lighting in their bedroom at a set time may be processed by an Internet of Things (IoT) interface application to cause the lighting in the bedroom to be adjusted at the set time. Moreover, the code block can be incorporated into subsequent prompts provided to the LLM to refine, modify, or otherwise alter the response while maintaining the integrity and context of the original response.

In one embodiment, the method 1200 obtains a request from a user of a mobile device (e.g., a smartphone, a tablet computing device, a smartwatch, etc.) and generates a program (i.e., a code block) that is executable by components of the mobile device to provide a response to the request. That is, the method 1200 is executed as part of a first application running on the mobile device and the program generated by the method 1200 is executable by the first application, or one or more second applications, running on the mobile device to provide the response to the request. For example, the first application may be a virtual assistant application and the one or more second applications may include a calendar application, an email application, a web browser application, and the like. In one embodiment, the program generated by the method 1200 is executable by one or more applications that are remote from the mobile device (e.g., a cloud service or an application executing on a further user device).

The method 1200 advantageously allows for the user to query the system, and provide a context specific response, in the above-described manner. Part of the response comprises a code block, or program, that can be subsequently executed by other components. For example, a user may query the system to create a workout based on their current level of fatigue. As described in detail below, part of the response to the query comprises a code block that when exported into another component e.g., a strength trainer application, causes the component to execute the code block. In the context of a strength training application this may be the execution of the workout routine generated from the physiological and context data. Therefore, as well as providing context specific responses, the system is able to produce code objects that can be used by external objects, or processes, to supplement the response. In some embodiments, the code block is used to add new functionality to an application (e.g., to add new functionality to an application of the physiological monitoring system, or to an application running on a mobile device of a user). For example, a user may request a new tracking chart for sleep need that was not available as part of the application prior to the user's request but is generated and displayed within the application in response to the user's request. As a further example, a user may request a novel score or metric to be calculated and used to monitor their fitness (e.g., a user request to display a "sleep need*recovery" metric every morning). In this way, the method 1200 dynamically expands the functionality of an application and/or physiological monitoring system based on user requests for new functionality.

In one embodiment, the method 1200 may be used in method 500 shown in FIG. 5. More particularly, the method 1200 may be used to map topics to context specific data at step 506. That is, the method 1200 can be used to obtain dynamic context data in the form of a code block that can then be integrated into a command at step 508 to provide a natural language response to a user's query (e.g., by evaluating the code block to obtain context specific data that is then integrated into the command). Put another way, the method 1200 may be used to map from the user's query or message to a set of context specific data (as described, for example, above in relation to the specific embodiment of FIG. 9).

As shown in step 1202, the method 1200 may include obtaining a message, e.g., including natural language text, or a portion of a natural language message, from a user of a physiological monitoring system. The skilled person will appreciate that while the present description is directed to use within a physiological monitoring system, the method is not intended to be limited as such and can be applied within any suitable system such as a mobile device system or application, a web application or system, an industrial control system, an Internet of Things management system, and the like. Similarly, it will be understood that a physiological monitoring system may include a variety of devices associated with a physiological monitor including, e.g., IoT devices and infrastructure, networks, smart devices, home and building automation systems, connected cameras and audio systems, and so forth, any of which may be used monitor a user and or control an environment of the user in furtherance of physiological monitoring and performance.

The portion of the natural language message may relate to a request from the user. The request may relate to one or more operations performable by the physiological monitoring system (e.g., a request for heart rate data, a request for sleep data, etc.) and/or one or more services available to the physiological monitoring system (e.g., a request to generate a workout or to access an external interface or service). The natural language message may form a part of a conversation between the user and a virtual agent associated with the physiological monitoring system (e.g., the interaction service of the present disclosure). In one embodiment, the portion corresponds to all of the natural language message received from the user.

The message received from the user may include a natural language request associated with the physiological monitoring system. In one embodiment, the natural language request is associated with (or related to) physiological data received from the user. For example, the message received from the user may include a request related to the user's recovery or strain which is associated with the user's physiological data (e.g., heart rate). As such, the method 1200 may include, prior to the step 1202, the step of receiving physiological data for the user from the physiological monitoring system which include a physiological monitor worn by the user and providing the physiological data.

The portion of the natural language message may comprise a request from the user in relation to a service available to or an operation performable by the physiological monitoring system. For example, the user may request that a workout be generated that can then be viewed, modified, and progress tracked within a workout application running as part of the physiological monitoring system. As a further example, the user may request for a summary of a previous sleep session to be displayed or for an external apparatus (e.g., a smart light bulb or switch) to be turned on or off at a set time. According to an aspect of the present disclosure, the method 1200 generates a program (i.e., code block) that is a representation of a response to the user request that can be efficiently processed by various components of the physiological monitoring system while allowing the response to be easily updated and modified (e.g., in response to a further request from the user or via an application running as part of the physiological monitoring system).

As shown in step 1204, the method 1200 may include providing a prompt to a large language model (LLM). The prompt may be operable to cause the LLM to output a code block which encodes a response to the request and may be processable by one or more components of the physiological monitoring system to generate one or more component specific representations of the response. In one embodiment, the step 1204 includes the steps of generating the prompt for the LLM and providing (transmitting) the prompt to the LLM.

In general, the LLM may be used to generate a program or other code block or structured query that encodes a response to the request and is processible (e.g., executed or interpreted) by a component of the system to generate a component specific representation of the response. To generate the code block, the LLM is provided with a prompt comprising: (i) a context block based on the message received from the user or the portion of the natural language message obtained at step 1204; (ii) a request for a code block encoding a response to the request based on the context block; (iii) the language schema which defines the structure, behavior, and functionality of the code within the code block (e.g., the language schema defines at least a syntax, functions, and operators for a programming language used to express the code block); and (iv) an object schema specifying programming objects available for use in the code block, which may be related to the user's request (e.g., operations which are performable by the physiological monitoring system or services which are available to the physiological monitoring system).

The context block may include part or all of the message, or a portion of the message, obtained at step 1204. The context block, in conjunction with the request, enables the LLM to determine the task to be performed. The request, alternatively referred to as a predetermined instruction, provides the relevant instructions for the LLM to perform the requested code generation task. That is, the predetermined instruction is a prompt or command which instructs the LLM to generate a code block representation of a response to the request from the user according to the language and object schemas included as further parts of the prompt. The instruction portion may thus comprise a predetermined prompt which identifies to the LLM the task to be performed and the use to be made of the language and object schemas. For example, the instruction portion may comprise the text, "Your job is to generate a program that will generate a full workout for the user based on the conversation. [ . . . ]". Other suitable instruction portions may be used.

It will be understood that the context block more generally relates to any of the static data, dynamic data, or other data described herein that might be useful for adapting the response from an LLM to the message received from the user, and that the context block may serve a variety of functions in this role. In the context of a physiological monitoring system, the context block may include a range of user-specific data such as physiological monitoring data or metrics derived therefrom, or other contextual data related to health, wellness, physiological monitoring or the like, and/or the context block may contain other information for incorporating such user-specific data into a response from the LLM. For example, in one aspect, the context block may literally contain portions of the message received from the user that may be useful to the LLM. In another aspect, the context block may contain user-specific data derived or inferred from the message, such as one or more topics or the like for the user message. In another aspect, the context block may include user-specific data such as data from a physiological monitoring system that stores data for the user. The context block may also or instead include a reference to where or how such data can be located in the physiological monitoring system. For example, where personal data such as a history of heart rate data is relevant to responding to a user message, the system may provide a link, pointer, query, AIQL query, or other code or the like indicating the manner in which the data of interest for a particular response can be retrieved from the physiological monitoring system. In another aspect, the context block may include a template token that can be used by another system (e.g., a physiological monitoring system) to incorporate data when rendering a response. Thus, for example, personal data including physiological data, demographic data, and the like, may be removed from a user message and replaced with a template token, so that the corresponding data can be re-inserted into a response from the LLM when rendered for a user, this avoiding the need to transmit personal data to the LLM. In another aspect, the context block may include references to, e.g., articles, web content, or other content that may be relevant to the response and/or of interest to the user based on the content of the message.

The language schema defines the language in which the code block is to be generated (e.g., the syntax, functions, operators, etc. of the language). As such, the code block is generated in a specific language defined according to a language schema provided to the LLM as part of the prompt. In one embodiment, the program is represented within the AIQL language described in detail above in relation to step 904 of the method 900 shown in FIG. 9. As such, the language schema for AIQL as described above may be provided as the language schema of the prompt.

The object schema is related to the user request (e.g., operations that are performable by the physiological monitoring system or services that are available to the physiological monitoring system) and defines the possible objects that can be represented in the language of the language schema within the code block. For example, when generating a code block for a workout, possible objects defined within the object schema may include a workout object that has a String name and a list of Sets (that are themselves objects having a String name and a list of cycles). As such, each object within the object schema has a name and one or more typed attributes. The object schema can be identified from a set of object schemas, and subsequently included in the prompt, based on the portion of the natural language message. That is, the natural language message (or the portion thereof) can be processed to identify the relevant object schema to be included in the prompt. In one embodiment, a topic classification and/or data lookup approach is used as described above in relation to steps 504 and 506 of FIG. 5 and the method 900 of FIG. 9. In particular, AIQL can be used to generate a structured query from the portion of the natural language message that is then used to identify the topic or context of the user request and so fetch a suitable object schema from a predefined set of object schemas (e.g., identify that the user request relates to a workout and so fetch a workout object schema, or identify that the user request relates to an interaction with an external system and so fetch an external interactions object schema).

In one embodiment, the prompt further comprises a list of functions (defined according to the language schema) that can act upon objects defined within the object schema. Continuing the previous example, the list of functions may comprise a function for generating a workout object defined as workout (name: string, sets: list)=>object. Each function may be accompanied with an inline comment (e.g., "//returns a workout") that can aid the LLM in the code generation task. In the same manner as described in relation to the object schema above, the list of functions can be identified, and subsequently included in the prompt, based on the natural language message (or the portion thereof).

In one embodiment, the prompt further comprises a previously generated code block. Each code block can be persistently stored to a storage location such that a code block can be fetched from the storage location to help provide a response to a user query. For example, a user may wish to alter a previously generated workout and so the code block associated with the previous workout is included in the subsequent prompt to the LLM. As a further example, a user may wish to go back and change a workout from a week ago and so the code block associated with the workout generated a week ago is included in the subsequent prompt. AIQL may be used to disambiguate the user's query (as described in relation to step 904 of FIG. 9 above) and fetch the appropriate code block from storage.

The LLM may be any suitably trained large language model. The LLM may be a proprietary LLM that is internally deployed within the physiological monitoring system (e.g., as part of the other resources 250 shown in the physiological monitoring system 200 of FIG. 2). Alternatively, the LLM may be offered as a service by a third party. In such implementations, the LLM is accessible via one or more application programming interface (API) endpoints. The code block may be obtained by providing the relevant prompt to the API endpoint and obtaining a response containing the code block. Example third party services include GPT-3 provided by OpenAI, Bloom by BigScience, and Google Bard.

As shown in step 1206, the method 1200 may include obtaining the code block from the LLM. This may include obtaining an output from the LLM where the code block is contained within the output. The code block may then be persistently stored for future use as described above. The code block may be configured for execution by one or more components of the physiological monitoring system to generate one or more component specific representations of the response. That is, the prompt is configured such that the LLM is caused to generate a code block which can be processed (executed, interpreted, etc.) by components of the physiological monitoring system to generate component specific representations of the response.

As shown in step 1208, the method 1200 may include processing the code block by a first component of the physiological monitoring system to generate a first component specific representation of the response. Here, processing the code block by the first component may include causing the first component to execute, interpret, evaluate, or otherwise process the code block to generate the first component specific representation. In one embodiment, processing the code block by the first component includes parsing and evaluating the code block as described in relation to step 906 and 908 of FIG. 9 respectively.

Because the code block is represented within a common language (as defined according to the language schema described above), different components of the physiological monitoring system can process the code block to generate a component specific (or context specific) representation of the response (e.g., an application object, a domain object, a user interface element or widget, a natural language text, etc.). Therefore, a single code block (or program) can be efficiently utilized across multiple components to generate multiple response representations. The code block may be plugged into various components of the physiological monitoring system thereby allowing the various components to take actions in response to the user request. That is the code block can be processed by the first component of the physiological monitoring system to generate a first component specific representation of the response and can be simultaneously or subsequently processed by a second component of the physiological monitoring system to generate second component specific representation of the response. Therefore, whilst the description below is provided in relation to the first component and the first component specific response, the skilled person will appreciate that the description is applicable to further component specific responses (e.g., a second component specific response).

In one embodiment, the first component is an application of the physiological monitoring system. For example, a physiological training application or workout application, a sleep monitoring application, a recovery application, etc. The application processes the code block to generate a representation of the response that is specific to the application. This can include integrating the response into the application (e.g., recording data represented within the response) and/or providing the response within the context of the application. For example, if the user request was for generating a workout and the code block generated represents the generated workout, then a workout application can process the code block to represent the workout within the workout application. The integration of, and communication between, components of the physiological monitoring system is therefore improved, and the user is able to utilize the functionality of the application as part of the provided response to their request. The user may then edit or adjust elements of the response within the application. For example, the user may adjust the number of reps, number of sets, weight, etc. of a generated workout within the user interface of the workout application.

In one embodiment, the first component is a user interface (UI) component such as a UI generation component or a UI management component. The UI component processes the code block to generate one or more user interface elements associated with the response. The user interface elements may then be integrated within components or applications of the physiological monitoring system (e.g., within a messaging application, or a report generation component).

In one embodiment, the first component is a text generation component. The text generation component processes the code block to generate a natural language representation of the response. For example, the text generation component can utilize an approach similar to that described in relation to steps 508 and 510 of FIG. 5 to generate a natural language representation of the response (code block) which can then be provided to a user (e.g., via a messaging application or similar).

In one embodiment, the first component is a context mapping component (e.g., a context fetcher). The context mapping component processes one or more mapping functions within the code block to obtain a component specific representation that corresponds to a set of context specific data (e.g., static data and/or dynamic data associated with the natural language request). Such an embodiment is described in more detail in relation to FIG. 9 where a code block, or structured query, is generated based on a user's message and subsequently evaluated (i.e., processed) to obtain context specific data which can be used to answer, or reply to, the user's message.

In one embodiment, the first component is an application external to the physiological monitoring system or an application of the physiological monitoring system configured to provide an interface to one or more applications external to the physiological monitoring system. For example, an interface to an external messaging application, an email application, or an IoT controller. The application external to the physiological monitoring system may be configured to process the code block to generate a representation of the response that is specific to that external application. That is, the external application may provide a module, component, or interface that is operable to process the code block and integrate the response into the external application and/or provide the response or a representation of the response within the context of the external application. For example, a code block representing a workout may be input to an interface provided by a third party messaging application and subsequently to allow a user to share the workout within the third party messaging application. The physiological monitoring system may additionally or alternatively provide an interface to one or more external applications. The interface can be configured to process the code block to integrate the response within the one or more external applications and/or generate a representation of the response within the one or more external applications. For example, a code block may be generated from a user's request to interact with an IoT object, and the interface may process the code block to instruct the IoT object to perform the requested interaction (e.g., lock or unlock a door, adjust a thermostat, turn on or off a light, etc.).

Beneficially, the code block generated use in an application external to the physiological monitoring system or an application of the physiological monitoring system can be linked to the request made to the system. For example, a user may input an initial query regarding their sleep quality and how to improve their sleep quality. As part of the generated response, the code block generated is used to control external devices, e.g., smart lighting devices, to implement a response to improve sleep quality—for example reducing light intensity at a particular time.

In one embodiment, the method 1200 may further include providing the first component specific representation to the user. For example, the first component specific representation may be output or presented to the user within a user interface. Alternatively, the first component specific representation may be provided by causing a tactile or auditory output to be generated. As a further alternative, providing the first component specific representation to the user may include causing control or operation of a function of a device of the physiological monitoring system or an external device.

The skilled person will appreciate that the above list of components is not intended to be exhaustive, and any suitable component may be used to generate a component specific representation of the response, including without limitation any suitable user device, computing device, exercise device, IoT device, hardware, software, application, and so forth.

Figure 13A:
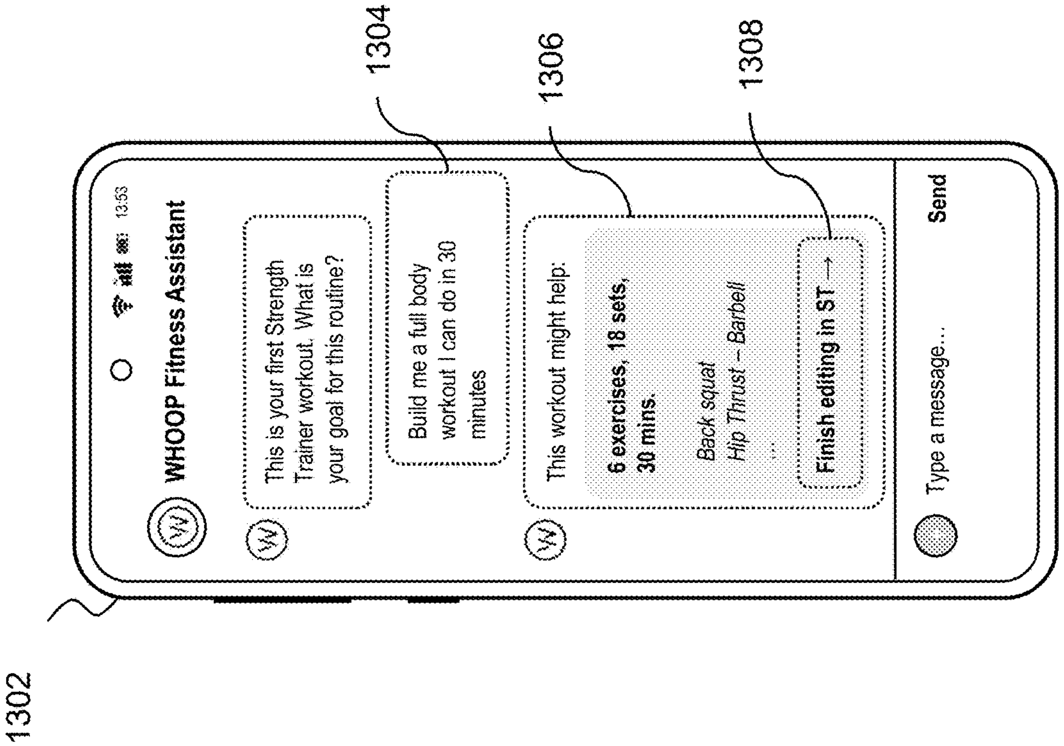
FIG. 13A shows a user interface of a physiological monitoring system.
Figure 13B:
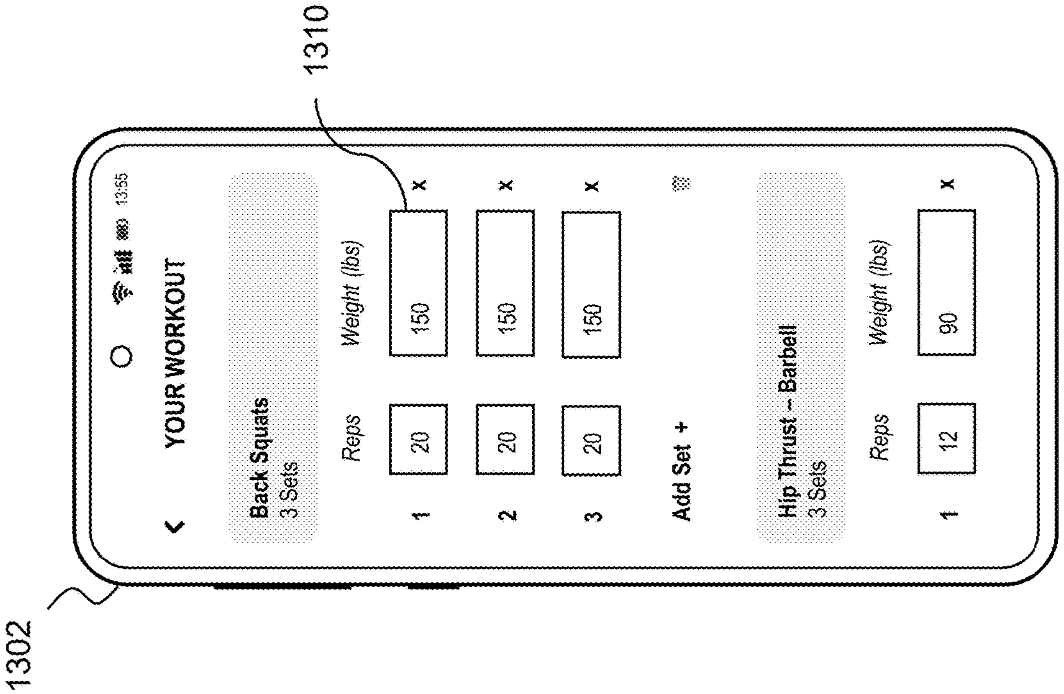
FIG. 13B shows a user interface of a physiological monitoring system.

FIGS. 13A and 13B show a user interface of a physiological monitoring system. FIG. 13A shows a user device 1302 upon which a user interface of a physiological monitoring system is displayed. The user device 1302 and the user interface may correspond to the user device 220 and the user interface 222 described above in relation to FIG. 2. The user interface presents a conversation between a user and the interaction service of the present disclosure (i.e., a virtual agent). The user interface takes the form of a messaging application whereby the user may enter messages within a message box that subsequently appear as messages within the messaging application.

FIG. 13A shows a message 1304 provided by a user of the user device 1302. The message 1304, "Build me a full body workout I can do in 30 minutes", includes a request from the user in relation to an operation performed by the physiological monitoring system—workout plan creation. As described in more detail above, a prompt is generated based on the message 1304 and the prompt is provided to a large language model (LLM) to generate a code block that encodes a response to the request. A text generation component processes the code block to generate a natural language representation of the response that is displayed within the message 1306. Alternatively, the text generation component, or another user interface component, generates a visual representation of the response from the code block (e.g., an image block or other object displayable within the user interface of the physiological monitoring system). A hyperlink 1308 (or button) allows the user to view the resulting workout within a workout application as shown in FIG. 13B.

FIG. 13B shows an application specific representation of the response generated from the user request included within the message 1304. Particularly, FIG. 13B shows the workout (i.e., response) within the context a workout application. The workout application processes the generated code block to display the elements of the response within the user interface of the workout application. This allows the user to adjust or modify the workout by, for example, adjusting the weight value within a text area 1310. The same code block is used to generate the natural language response within the message 1306 and the application specific response shown in FIG. 13B.

According to the foregoing, a variety of techniques may be used in various combinations to leverage the capabilities of large language models with context data such as user-specific data or static content, e.g., for a physiological monitoring system, to provide user-specific and platform dependent responses to user questions. By way of non-limiting examples, in one embodiment, a method (or computer program product embodying the method) may include receiving physiological data for a user from a system, the system including a physiological monitor worn by the user and the physiological monitor providing the physiological data; receiving a message from the user, wherein the message includes a question from the user in a natural language form; and creating one or more prompts for use with large language models. The one or more prompts may include a request for a code block that encodes a response to the question and is processable by one or more components of the system to generate one or more component specific representations of the response, a language schema for code within the code block, the language schema defining at least a syntax, functions, and operators for a programming language used to express the code block, an object schema, the object schema specifying programming objects available for use in the code block, and a context block relating to user-specific data. The method may further include transmitting the one or more prompts to one or more large language models; receiving the response containing the code block from the one or more large language models; and transmitting the code block that encodes the response to a component of the system for use in providing the response to the user.

The method may further include processing the code block on a component of the system to provide the response to the user in a component dependent and user specific manner. The context block may include one or more template tokens to be replaced with predetermined user-specific data when presenting the response to the user. The context block may include an identification of the user-specific data, and the instruction may include a request for the creation of a query to retrieve the user-specific data from the system when providing the response to the user. In another aspect, the context block includes a portion of the physiological data for the user. In another aspect, the instruction includes a request to rephrase the physiological data for presentation in the response to the user. The context data may, for example, include at least one of a topic for the question, dynamic data related to the topic for the question, and static data related to the topic for the question. The method may include presenting a preliminary prompt to one of the one or more large language models to generate a second code block based on the message operable to obtain at least a portion of the context block used in the prompt. The method may include presenting a preliminary request to one of the one or more large language models to identify one or more topics for the question. The method may include identifying one or more topics in the question, and mapping at least one of the one or more topics to a portion of the physiological data for the user. Identifying one or more topics may, for example, include presenting the question to one of the large language models with a list of candidate topics and requesting a selection of the one or more topics for the question from the list of candidate topics. In another aspect, the instruction includes an instruction to rephrase the context data in a natural language form for use in generating the response.

In another aspect, the method may include monitoring a responsiveness of the large language model and optimizing a use of the large language model by varying a length limit for text-based responses according to the responsiveness. It will be understood that the responsiveness of a large language model may vary for a variety of reasons, e.g., a current computational load on the underlying inference engine, hardware or software issues, network performance or latency, the volume of incoming requests, the complexity of incoming requests, and so forth. Regardless of the causes, the responsiveness of the large language model may be measured as described herein and used as the basis for throttling requests to the LLM, e.g., by explicitly reducing a length limit for responses when performance or latency is poor.

In general, the question in the user message may be an explicit question, e.g., beginning with who, what, where, why, how, and so forth. However, the message may also or instead contain an implicit question such as a request for content, a request for executable code, a request for an analysis, or the like in the form of a command or instruction, which concurrently implies a request to perform the requested command or instruction, e.g., a question of "can you perform this instruction." Thus, in the context of this disclosure, a question may also or instead include a command, an instruction, or any other request or the like that might usefully be submitted to a large language model or other inference engine implicitly asking for a response. For example, an implicit question may include a request for a creation of user-specific content (e.g., "[can you] please create a workout program to increase my $VO_2$ max [?]"), a request for a particular analysis (e.g., "[can you tell me] how have I been sleeping this week [?]"), or a request to control a component of the user's environment (e.g., "[can you please] set an alarm to wake me up at the optimal time tomorrow morning [?]"). All such implicit questions and the like are intended to fall within the scope of a "question" in a user message as described herein. Thus in one aspect, the question may be an implicit question from the user including a request for a creation of user-specific content.

As described herein, the large language model(s) may also be used to generate functional code that can, e.g., render a functional response to the user's message, e.g., by controlling devices within the system that are connected to a network, such as a thermostat, an audio system, an alarm, a television, a computer, a scale, an exercise device, and so forth. Thus in one aspect, the code block may express a functional response to the message in which elements of the user's environment are provided with executable code to respond to the message. Thus, in one aspect, the method may include processing the code block on an Internet-of-Things device in the system to provide a functional response to the message from the user.

According to the foregoing, there is also disclosed herein a system including a physiological monitor used to acquire physiological data from a user; one or more computing devices associated with the user; and a query module. The query module may execute on one or more processors, and may be configured by non-transitory computer executable code to perform the steps of: receiving a message from the user, wherein the message includes a question from the user in a natural language form; and creating one or more prompts for use with large language models. The one or more prompts may include: a request for a code block that encodes a response to the question and is processable by the one or more computing devices to generate one or more component specific representations of the response, a language schema for code within the code block, the language schema defining at least a syntax, functions, and operators for a programming language used to express the code block, an object schema, the object schema specifying programming objects available for use in the code block, and a context block relating to user-specific data for the user based on the physiological data. The query module may be further configured to perform the steps of transmitting the one or more prompts to one or more large language models; and receiving the code block that encodes the response from one of the large language models.

The resulting response may be transmitted, e.g., to one of the computing devices associated with the user for presentation to the user, or for other action or the like. This may include, e.g., a phone, tablet, desktop computer, or the like associated with the user, on which the response can be rendered for the user. This may also or instead include any of the IoT or other infrastructure described herein, in which case the response can be processed to provide a functional response to the user that is responsive to the user's initial message. Thus, the query module may be further configured to perform the step of transmitting the response containing the code block to one of the computing devices of the system, wherein the one of the computing devices processes the code block to provide the response for the user. In another aspect, the system may include a context service configured to process the message to identify at least one topic for the question, map the at least one topic to dynamic and static content stored by the system, and retrieve the dynamic and static content for use in the prompt.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above, and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A computer program product comprising computer executable code embodied in a non-transitory computer readable medium that, when executing on one or more computing devices, causes the one or more computing devices to perform the steps of:

receiving physiological data for a user from a system, the system including a physiological monitor worn by the user and the physiological monitor providing the physiological data;

receiving a message from the user, wherein the message includes a question from the user in a natural language form;

identifying one or more topics in the question, wherein identifying the one or more topics includes presenting the question to one or more large language models with a list of candidate topics and requesting a selection of the one or more topics for the question from the list of candidate topics;

mapping at least one of the one or more topics to a portion of the physiological data for the user;

creating one or more prompts for use with large language models, the one or more prompts including:

a request for a code block that encodes a response to the question and is processable by one or more components of the system to generate one or more component specific representations of the response, a language schema for code within the code block, the language schema defining at least a syntax, functions, and operators for a programming language used to express the code block, an object schema, the object schema specifying programming objects available for use in the code block, and a context block relating to user-specific data;

transmitting the one or more prompts to the one or more large language models;

receiving the response containing the code block from the one or more large language models; and transmitting the code block that encodes the response to a component of the system for use in providing the response to the user.

2. The computer program product of claim 1, further comprising processing the code block on the component of the system to provide the response to the user in a component dependent and user specific manner.

3. The computer program product of claim 1, wherein the context block includes one or more template tokens to be replaced with predetermined user-specific data when presenting the response to the user.

4. The computer program product of claim 1, wherein the context block includes an identification of the user-specific data, and wherein the request for the code block includes a request for creation of a query to retrieve the user-specific data from the system when providing the response to the user.

5. The computer program product of claim 1, wherein the context block includes the portion of the physiological data for the user.

6. The computer program product of claim 1, wherein the request for the code block includes a request to rephrase the physiological data for presentation in the response to the user.

7. The computer program product of claim 1, wherein the context block includes at least one of the one or more topics for the question, dynamic data related to the at least one of the one or more topics for the question, and static data related to the at least one of the one or more topics for the question.

8. The computer program product of claim 1, further comprising code that performs the step of presenting a preliminary prompt to one of the one or more large language models to generate a second code block based on the message operable to obtain at least a portion of the context block used in the one or more prompts.

9. The computer program product of claim 1, further comprising code that performs the step of presenting a preliminary request to one of the one or more large language models to identify the list of candidate topics for the question.

10. The computer program product of claim 1, wherein the one or more prompts include an instruction to rephrase context data relating to a user query in a natural language form for use in generating the response.

11. The computer program product of claim 1, further comprising code that performs the steps of monitoring a responsiveness of the one or more large language models and optimizing a use of the one or more large language model by varying a length limit for text-based responses according to the responsiveness.

12. The computer program product of claim 1, wherein the question is an implicit question from the user including a request for a creation of user-specific content.

13. The computer program product of claim 1, further comprising code that performs the step of processing the code block on an Internet-of-Things device in the system to provide a functional response to the message from the user.

14. A system comprising:

a physiological monitor used to acquire physiological data from a user;

one or more computing devices associated with the user; and a query module, the query module executing on one or more processors and configured by non-transitory computer executable code to perform the steps of:

receiving a message from the user, wherein the message includes a question from the user in a natural language form;

identifying one or more topics in the question, wherein identifying the one or more topics includes presenting the question to a first one or more large language models with a list of candidate topics and requesting a selection of the one or more topics for the question from the list of candidate topics;

mapping at least one of the one or more topics to a portion of the physiological data for the user;

creating one or more prompts for use with large language models, the one or more prompts including:

a request for a code block that encodes a response to the question and is processable by the one or more computing devices to generate one or more component specific representations of the response, a language schema for code within the code block, the language schema defining at least a syntax, functions, and operators for a programming language used to express the code block, an object schema, the object schema specifying programming objects available for use in the code block, and a context block relating to user-specific data for the user based on the physiological data;

transmitting the one or more prompts to a second one or more large language models; and receiving the code block that encodes the response from the second one or more large language models.

15. The system of claim 14, the query module further configured to perform the step of transmitting the response containing the code block to one of the computing devices of the system, wherein the one of the computing devices processes the code block to provide the response for the user.

16. The system of claim 14, further comprising a context service configured to process the message to identify at least one topic for the question, map the at least one topic to dynamic and static content stored by the system, and retrieve the dynamic and static content for use in the one or more prompts.

17. A method comprising:

obtaining a portion of a natural language message received from a user of a system, wherein the portion of the natural language message relates to a request from the user;

providing, to a first large language model (LLM), a prompt operable to cause the first LLM to output a code block that encodes a response to the request and is processable by one or more components of the system to generate one or more component specific representations of the response, wherein the prompt comprises a predetermined instruction, a context block based on the portion of the natural language message, a language schema for code within the code block, and an object schema that defines objects usable within the code block, wherein the object schema is related to the request from the user;

obtaining the code block from the first LLM; and monitoring a responsiveness of the first LLM and optimizing a use of the first LLM by varying a length limit for text-based responses according to the responsiveness.

18. The method of claim 17, wherein the system is a physiological monitoring system.

19. A computer program product comprising computer executable code embodied in a non-transitory computer readable medium that, when executing on one or more computing devices, causes the one or more computing devices to perform the steps of:

receiving physiological data for a user from a system, the system including a physiological monitor worn by the user and the physiological monitor providing the physiological data;

receiving a message from the user, wherein the message includes a question from the user in a natural language form;

creating one or more prompts for use with large language models, the one or more prompts including:

a request for a code block that encodes a response to the question and is processable by one or more components of the system to generate one or more component specific representations of the response, a language schema for code within the code block, the language schema defining at least a syntax, functions, and operators for a programming language used to express the code block, an object schema, the object schema specifying programming objects available for use in the code block, and a context block relating to user-specific data;

transmitting the one or more prompts to one or more large language models;

receiving the response containing the code block from the one or more large language models;

transmitting the code block that encodes the response to a component of the system for use in providing the response to the user; and monitoring a responsiveness of the one or more large language models and optimizing a use of the one or more large language models by varying a length limit for text-based responses according to the responsiveness.

20. A system comprising:

a physiological monitor used to acquire physiological data from a user;

one or more computing devices associated with the user; and a query module, the query module executing on one or more processors and configured by non-transitory computer executable code to perform the steps of:

receiving a message from the user, wherein the message includes a question from the user in a natural language form;

creating one or more prompts for use with large language models, the one or more prompts including:

a request for a code block that encodes a response to the question and is processable by the one or more computing devices to generate one or more component specific representations of the response, a language schema for code within the code block, the language schema defining at least a syntax, functions, and operators for a programming language used to express the code block, an object schema, the object schema specifying programming objects available for use in the code block, and a context block relating to user-specific data for the user based on the physiological data;

transmitting the one or more prompts to one or more large language models;

receiving the code block that encodes the response from one of the large language models; and monitoring a responsiveness of the one or more large language models and optimizing a use of the one or more large language models by varying a length limit for text-based responses according to the responsiveness.

21. A method comprising:

obtaining a portion of a natural language message received from a user of a system, wherein the portion of the natural language message relates to a request from the user;

identifying one or more topics in the portion of the natural language message, wherein identifying the one or more topics includes presenting the portion of the natural language message to a first large language model (LLM) with a list of candidate topics and requesting a selection of the one or more topics from the list of candidate topics;

mapping at least one of the one or more topics to context data associated with the system;

providing, to the first LLM, a prompt operable to cause the first LLM to output a code block that encodes a response to the request and is processable by one or more components of the system to generate one or more component specific representations of the response, wherein the prompt comprises a predetermined instruction, a context block based on the portion of the natural language message, a language schema for code within the code block, and an object schema that defines objects usable within the code block, wherein the object schema is related to the request from the user; and obtaining the code block from the first LLM.

* * * * *